(12) United States Patent
Tupper et al.

(10) Patent No.: US 7,338,636 B2
(45) Date of Patent: Mar. 4, 2008

(54) MANIPULATING MICRON SCALE ITEMS

(75) Inventors: Malinda M. Tupper, Cambridge, MA (US); Michael J. Cima, Winchester, MA (US); Marjorie E. Chopinaud, Feytiat (FR)

(73) Assignee: Massachusetts Institute of Technology, Cambridge, MA (US)

( * ) Notice: Subject to any disclaimer, the term of this patent is extended or adjusted under 35 U.S.C. 154(b) by 888 days.

(21) Appl. No.: 10/770,347

(22) Filed: Feb. 2, 2004

(65) Prior Publication Data
US 2004/0259377 A1 Dec. 23, 2004

Related U.S. Application Data

(62) Division of application No. 09/976,835, filed on Oct. 12, 2001, now Pat. No. 6,686,207.

(51) Int. Cl.
*B01L 3/02* (2006.01)
*G01N 1/00* (2006.01)

(52) U.S. Cl. .......................... 422/63; 422/99; 422/100; 422/101

(58) Field of Classification Search ................ 422/100, 422/101, 99, 68.1, 63; 436/174, 177; 204/164
See application file for complete search history.

(56) References Cited

U.S. PATENT DOCUMENTS

| | | | |
|---|---|---|---|
| 4,487,836 A | 12/1984 | Takayanagi et al. | |
| 4,948,515 A | 8/1990 | Okumura | |
| 5,355,577 A | 10/1994 | Cohn | |
| 5,415,784 A | 5/1995 | Akutsu et al. | |
| 5,669,973 A | 9/1997 | Pletcher | |
| 5,699,649 A | 12/1997 | Abrams et al. | |
| 5,714,007 A | 2/1998 | Pletcher et al. | |
| 5,788,814 A | 8/1998 | Sun et al. | |
| 5,846,595 A | 12/1998 | Sun et al. | |
| 5,858,099 A | 1/1999 | Sun et al. | |

(Continued)

OTHER PUBLICATIONS

Boehringer, K., Goldberg, K., Cohn, M., Howe, R. and Pisano, A., "Parallel Microassembly with Electrostatic Force Fields," Proceedings of the 1998 IEEE International Conference on Robotics and Automation, Leuven, Belgium, May 1998: pp. 1204-1211.

(Continued)

*Primary Examiner*—Brian R. Gordon
(74) *Attorney, Agent, or Firm*—Steven J. Weissburg

(57) ABSTRACT

Micron scale dielectric items are manipulated by methods and apparatus taking advantage of spatially non-uniform field. Such fields give rise to a force on dielectric items, directing them generally toward regions of more concentrated field. The electrode may be elongated, either unitary, with a generally planar counter electrode, or dual, such as parallel pins, loops or plates. If dual, particles are generally attracted to regions of high field concentration, including tips, edges and spaces between electrode conductors. Items can be granular, threadlike, or sheets, and microelectronic parts and other shapes. Items can also be collected directly into a recess of a pharmaceutical material delivery microchip, with a conductive membrane of the microchip acting as a manipulating electrode. Items are attracted without regard to their surface charge, or the polarity of the field, which can be AC or DC. Charging, or knowing the charge of items to be manipulated is not necessary. The amount of material collected can be precisely controlled by varying parameters of collection, such as distance between the electrode and the items, distance between dual conductors, size (diameter, length) of the conductors, any dielectric sheathing thereof, and voltage. Elongated electrodes can be used to manipulate items into and from recesses, such as wells of microtitre trays, microchips, and semiconductor chips.

23 Claims, 42 Drawing Sheets

U.S. PATENT DOCUMENTS

| | | | |
|---|---|---|---|
| 5,960,609 A | 10/1999 | Abrams et al. |
| 5,983,135 A | 11/1999 | Avrahami |
| 5,988,432 A | 11/1999 | Sun |
| 6,004,752 A | 12/1999 | Loewy et al. |
| 6,007,630 A | 12/1999 | Pletcher et al. |
| 6,045,753 A | 4/2000 | Loewy et al. |
| 6,063,194 A | 5/2000 | Poliniak et al. |
| 6,074,688 A | 6/2000 | Pletcher et al. |
| 6,096,368 A | 8/2000 | Sun |
| 6,096,554 A | 8/2000 | Tajima |
| 6,126,803 A | 10/2000 | Halm et al. |
| 6,146,685 A | 11/2000 | Chrai |
| 6,149,774 A | 11/2000 | Sun et al. |
| 6,176,977 B1 | 1/2001 | Taylor et al. |
| 6,350,417 B1 | 2/2002 | Lau et al. |
| 6,482,327 B1 | 11/2002 | Mori et al. |
| 6,485,624 B1 | 11/2002 | Pfefferle et al. |
| 6,491,797 B1 | 12/2002 | Locke et al. |
| 6,503,402 B2 | 1/2003 | Jensen |
| 2001/0020588 A1 | 9/2001 | Adourian et al. |
| 2001/0023852 A1 | 9/2001 | Kato et al. |
| 2002/0008069 A1 | 1/2002 | Kato et al. |
| 2002/0098131 A1 | 7/2002 | Taylor et al. |
| 2002/0134664 A1 | 9/2002 | Taylor et al. |
| 2002/0134665 A1 | 9/2002 | Taylor et al. |
| 2003/0062265 A1 | 4/2003 | King et al. |

OTHER PUBLICATIONS

Hughes, M. "AC Electrokinetics: Applications for Nanotechnology," draft submitted to Seventh Foresight Conference on Molecular Nanotechnology, which took place Oct. 15-17, 1999, not known if actually published at approximately that time. First located by the inventors on Aug. 23, 2001 at http://www.foresight.org/Conferences/MNT7/Papers/Hughes/. The Conference outline, which lists the submitted papers, was found at http://www.foresight.org/Conferences/MNT7/.

Stix, G., "Pour Me Another" Scientific American, Mar. 2001, p. 20.

Parallel pins

Parallel Pins

Parallel pins with insulator

Parallel loops loops loops

DC collection                    Disc and ring

DC collection, disc and ring

DC collection, disc and plate

DC Collection, disc and plate

MANIPULATING MICRON SCALE ITEMS

This is a divisional of co-assigned U.S. application, U.S. Ser. No. 09/976,835, filed on Oct. 12, 2001 now U.S. Pat. No. 6,686,207, and claims the benefit of that earlier application. The entire disclosure of that application is hereby incorporated fully herein, by reference.

GOVERNMENT RIGHTS

The United States Government has certain rights in this invention pursuant to the Army Research Office Award # DAAH04-95-1-0104, Multidisciplinary Research in Smart Composites, awarded on Mar. 1, 1995.

The inventions disclosed herein will be understood with regard to the following description, appended claims and accompanying drawings, where:

DETAILED DESCRIPTION

Figure 1A:
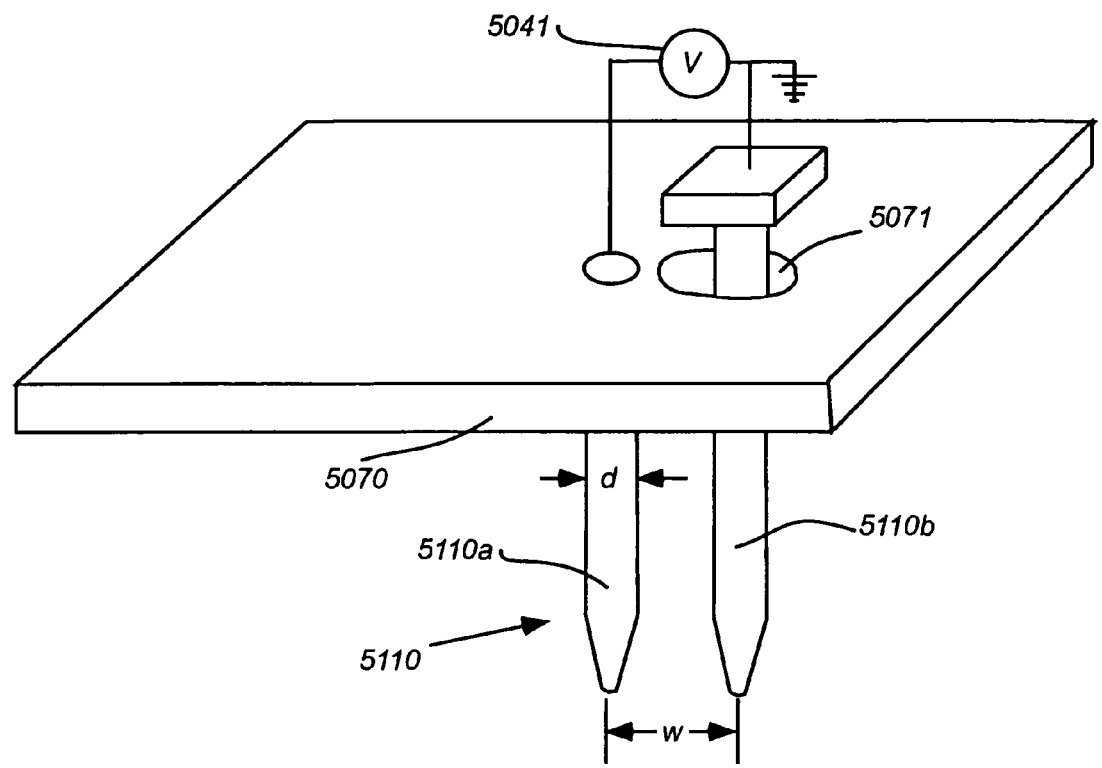
FIG. 1A is a schematic perspective rendition showing an apparatus for manipulating micron scale items, having a pair of elongated pin-like electrodes.

There are many applications that require precise dispensing of very small quantities of dry particulate materials. High throughput testing of pigments, phosphors, and pharmaceutical compounds require rapid, precise dispensing of these powders. Small, accurate doses of active drug powders must be formed into tablets, or disposed into other drug delivery devices such as inhalers, transdermal patches, or implantable drug-delivery devices. Such powder may have a nominal grain size of between 1 and 800 microns, with typical doses desired to be manipulated being in a range of between 0.1 micrograms and 20 milligrams.

These substances may be dispensed by first dispersing the material in a liquid carrier, then using a liquid pipette to dispense a known volume of the suspension. Dispensing in liquid presents a multitude of problems for many applications. The liquid may alter the surface or the polymorphic form of the material, changing its characteristics. Such changes may drastically alter the effect of an active drug or reagent. The particles may also clog the tip of a pipette, preventing proper dispensing. Liquid dispensing also requires that the liquid subsequently be removed.

So-called, "dry" pipettes exist, but their accuracy is limited to ±1 milligrams. Most pharmaceutical applications require much greater accuracy, and these dry pipettes are still subject to clogging. Therefore, other methods are needed to achieve necessary accuracy, efficacy, and high throughput for these applications.

Some methods employed in combinatorial materials synthesis and development use multi-well "microtitre" trays to simultaneously carry out multiple small-scale reactions. It is beneficial to be able to provide very small amounts of dry powder into each well of the microtitre tray, so that each well may be used for a separate test. For instance, it may be necessary to dispense as little as a single particle, or up to 100 milligrams into a well of approximately 1.0 milliliter. Various additives may then be added to the individual wells to carry out the desired reactions.

Similarly, microchips are composed of a plurality (sometimes up to thousands) of reservoirs, each of which contain a precisely measured amount of a pharmaceutical material. Pharmaceutical material delivery "microchips" are described in (J. Santini, M. Cima, and R. Langer, U.S. Pat. No. 5,797,898), which is incorporated fully herein by reference. Such microchips may be biocompatible and implantable, or used for non-in vivo applications, in which case they need not be implantable. As used herein, "microchips" refers to such devices. These microchips are small (~1.0 cm×1.0 cm×330 micron) silicon wafers containing multiple wells that may be filled with an active drug or other pharmaceutical material to be delivered or manipulated. The top of each well is covered with a thin electrically conductive membrane, which may be removed by applying a potential between the membrane and a cathode located on the chip. The wells may be filled by microinjection of a liquid, inkjet printing, or spin coating methods. In cases where the desired substance to be released is a dry powder, the substance is dissolved or dispersed in a liquid carrier and injected into the wells, then freeze dried to remove the liquid. There are many instances, however, where it would be desirable to directly fill the wells with dried powders. This would allow a higher amount of material to be deposited in each well, and prevent any changes in efficacy or polymorphic form that may be caused by lyophilizing the powder.

Some combinatorial chemical synthesis methods require that small amounts of polymer beads, called "resin," or dry powdered reagents, be placed in each well of a microtitre plate to carry out solid-phase reactions. The polymer beads are typically on the order of 30 to 600 microns (~0.12 to 950 micrograms). If powdered material is introduced into a well that contains a bead by first dispersing the power into a liquid, the liquid may preclude some possible reactions for the beads. If a pipette is used, the beads may clog the tip thereof. Thus, there is a need for a method and apparatus to transport such beads, and powder materials for interaction therewith.

Surprisingly, a similar need exists in the unrelated area of micro-electronic component assembly. Microelectronic devices require precise placement of very small, shaped components onto a target. Surface mount devices are typically assembled onto chips by an automated pick and place operation. Pick and place methods generally apply positive pressure in some way to the component, to place it on the target chip. Some small components, or components made of a deformable material, may be damaged by this process. Additionally, when very precise location is required, the vibration of these mechanical systems and uncontrolled electrostatic charge that may build up on the dielectric surfaces can cause misplacement of the components. Thus, a new process that does not use positive pressure, and that eliminates or minimizes vibration would be very useful for very small components. Presently, parts on the order of 100-300 microns are being used, with the size expected to be smaller in the near future.

Collecting Apparatus Parallel Pins

An apparatus that has been used to collect, manipulate, and deposit microgram quantities of micron scale items (defined below) is shown schematically with reference to FIG. 1A. This apparatus has a manipulating electrode 5110 of two parallel pins 5110a and 5110b, each having a diameter d and spaced a distance w apart. The electrode 5110 protrudes from an electrode support 5070. As shown schematically in FIG. 1B, a quantity of particles 5100 are provided in a volume forming a particle bed that is retained in a well 5116 of a particle support 5114, having a surface 5117. The particle support is electrically isolated. For instance, glass beads on the order of between 70 to 100 μm diameter have been collected as well as larger, 600 μm diameter. Also, ~2-10 micron, sodium fluorescein particles, and ~50-500 micron aspirin particles, have been collected with this type of apparatus. An AC bias may be applied by a voltage source 5041 between the two electrode pins by connecting one pin 5110a to the AC power source 5041, and the other 5110b to electrical ground.

Figure 1B:
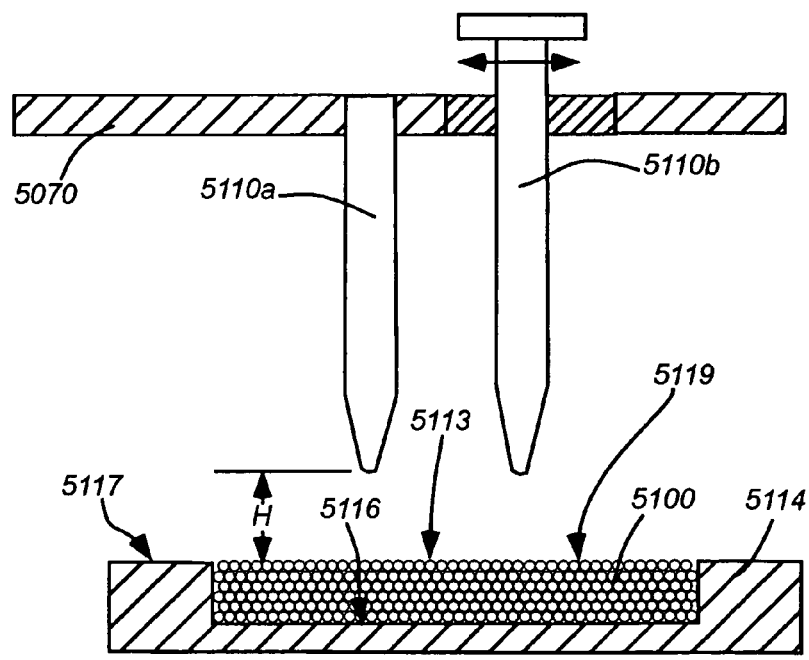
FIG. 1B is a schematic elevation section showing the apparatus of FIG. 1A, along with a particle bed, before any power is applied to the electrode.
Figure 1C:
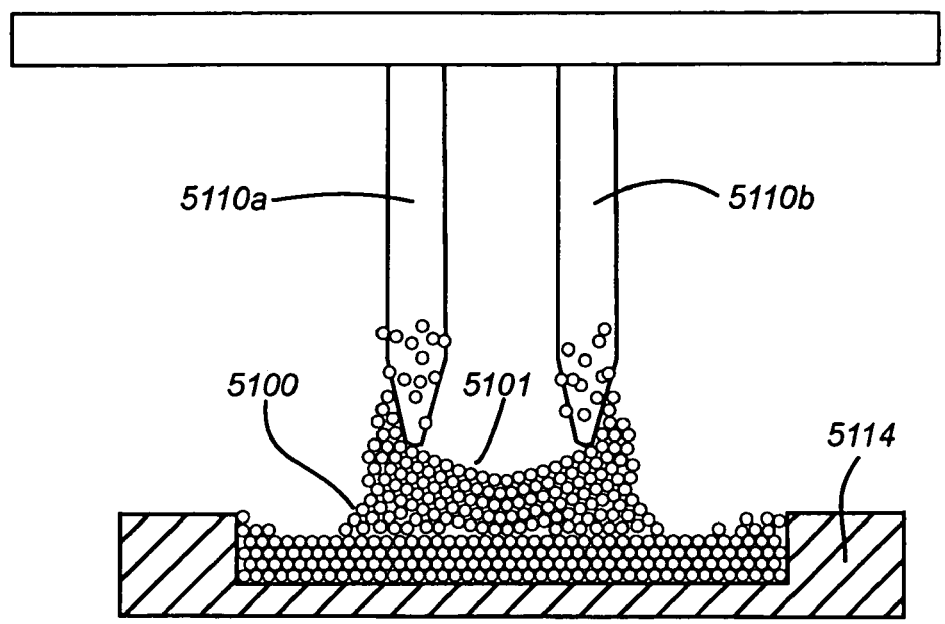
FIG. 1C is a schematic elevation section showing the apparatus of FIG. 1A, after power is applied to the electrode.

As shown in FIG. 1B, the electrode pins are placed at a separation H from the particle bed surface 5119. Subsequently, an AC voltage V is applied. FIG. 1C shows the situation after the voltage has been applied. An electric field arises so that, as shown schematically in FIG. 1C, the particles 5100 are initially attracted to the pin tips. As more particles 5100 are collected they form "strings" 5101 between the two pins 5110a and 5110b and the body of the particle bed. (The underlying mechanism of attraction is discussed below.)

Figure 1D:
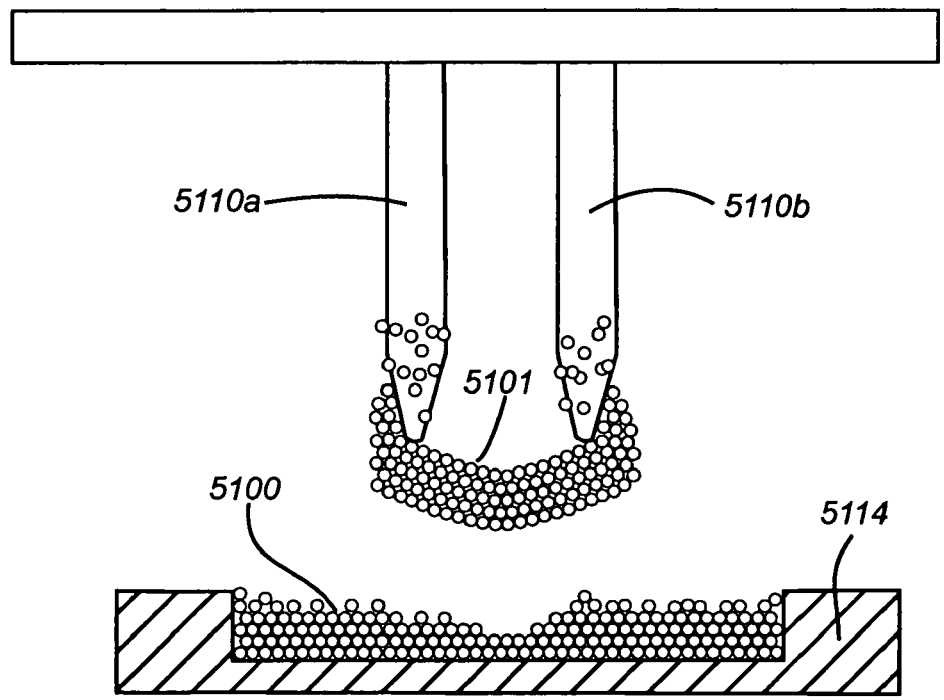
FIG. 1D is a schematic elevation section showing the apparatus of FIG. 1A, after power is applied to the electrode and the electrode is drawn away from the particle bed.
Figure 44:
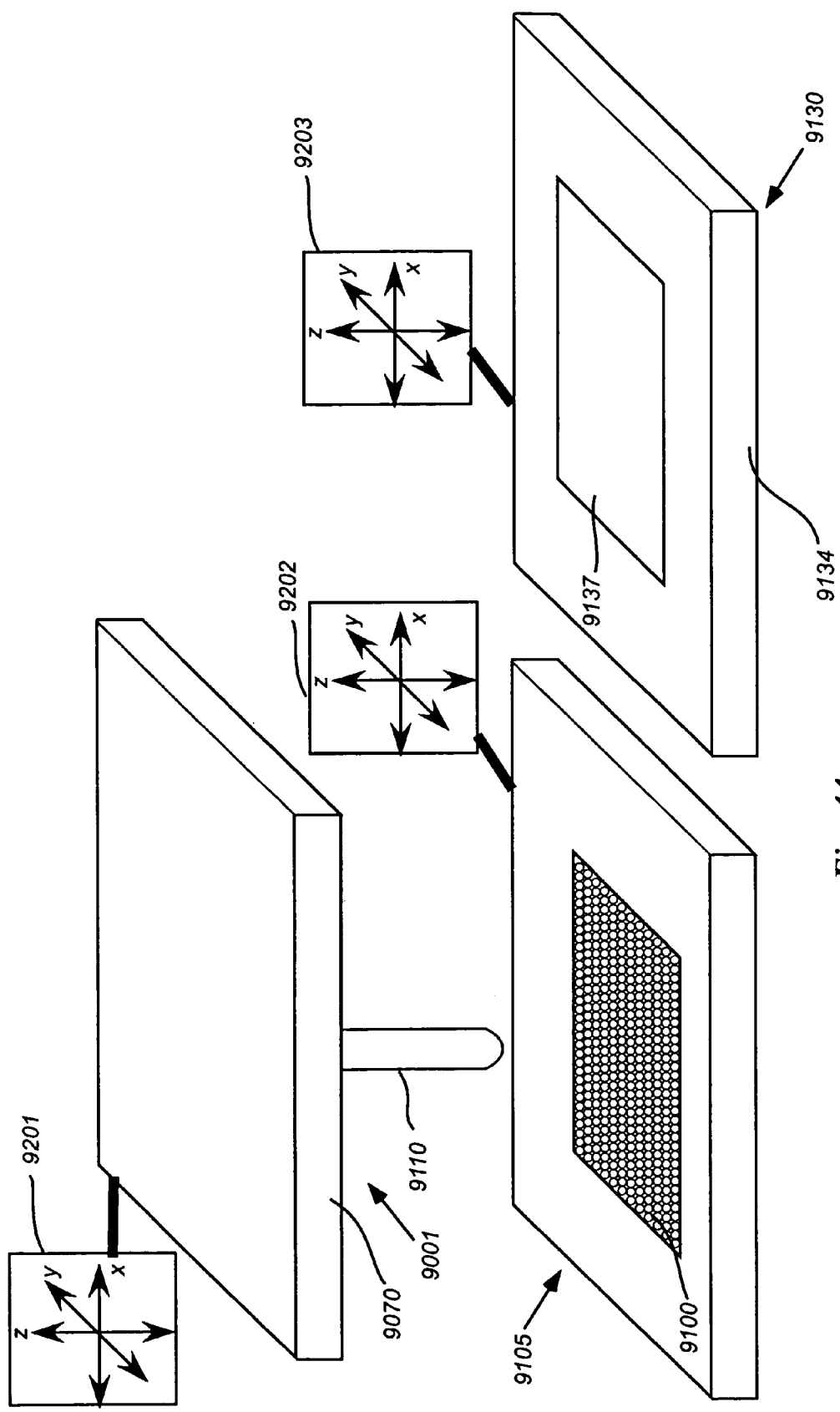
FIG. 44 shows, schematically, a collecting module, with a generic manipulating electrode, collecting generic items from a supply, to be transported to a generic target, where each of the collecting module, item supply module and target are provided with an x-y-z transport module to position each relative to the environment, and to the other modules.

Eventually (within a relatively short time, on the order of less than a few seconds) no additional particles are drawn toward the pins. As shown in FIG. 1D, the two pin electrode 5110 is then drawn away from the item support 5114, for instance by a standard vertical stage, not shown, which moves either the electrode support, or the particle support, or both. (Alternatively, the electrode can be moved horizontally relative to the particle support, or, vice versa.) (FIG. 44 shows, schematically, a collecting module 9001, with a generic manipulating electrode 9110, collecting generic items 9100 from a supply 9103 of a supply module 9105, to be transported to a target region 9137 of a generic target 9130 module. Each of the collecting module 9001 and item supply module 9105 are provided with an x-y-z transport module 9201, 9202, 9203, respectively, to position each relative to the environment, and to the other. These x-y-z transport modules are shown schematically by boxes. Any suitable device is intended. Any of the collecting electrodes discussed herein can be so transported, relative to any supply of items discussed herein, to first attract them, and then to disengage attracted items from the remaining, non-retained items.)

The particle strings 5101 remain in place relative to and between the electrodes 5110a and 5110b as they are raised away from the powder bed support 5114. Eventually, the pins are so far away from the particles remaining at the support, that the remaining particles are not attracted sufficiently to the electrode 5110 to overcome the force of gravity, and they remain in place, resting on the particle support 5114. Thus, a quantity of particles becomes separated from the particle bed 5113. Thus, the electrode 5110 can be used to collect a quantity of micron scale items 5100.

The electrodes 5110a and 5110b may then be moved over a recipient target, such as the well of a microtitre plate, a microchip reservoir, etc., as discussed in more detail below, where the items 5100 are deposited. A convenient way to deposit the items 5100 is to remove the applied potential, as discussed below.

Figure 1E:
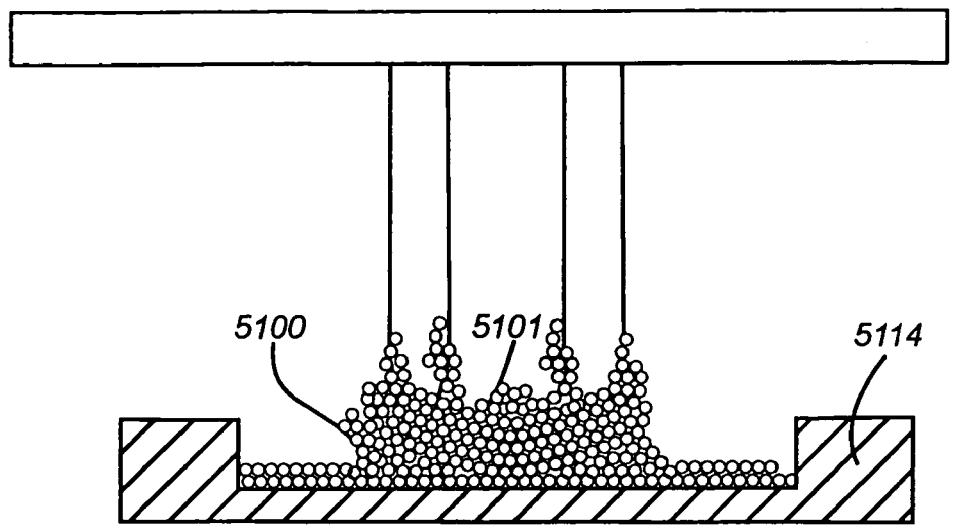
FIG. 1E is a schematic elevation section showing the apparatus of FIG. 1A, after power is applied to the electrode, where the initial separation H is negative and the electrode tips are submerged below the particle bed surface.
Figure 2A:
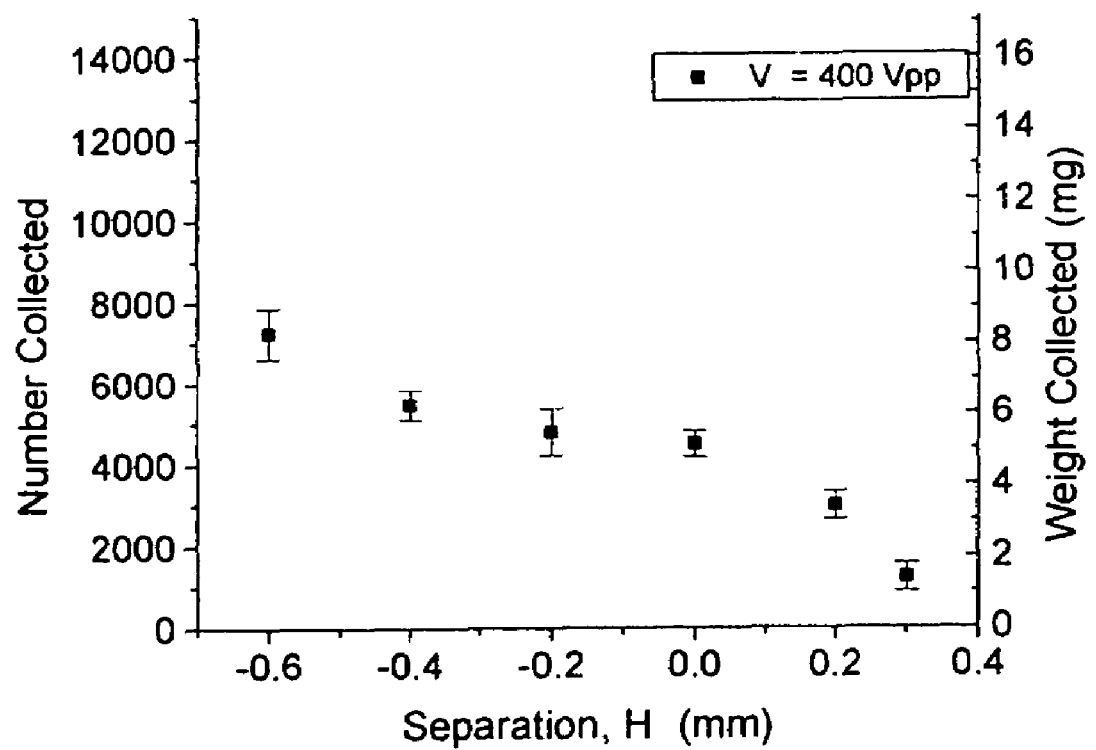
FIG. 2A is a graphical representation of the relationship between amount of material collected and separation H when the voltage is applied, for a fixed voltage of 400 Vpp, for a two pin electrode such as shown in FIG. 1A.

Various parameters of operation can be altered. For instance, the height H of the electrode 5110 above the particle bed surface 5119 at the time that the voltage source is turned on, can be altered. The height H can be positive (above the surface), as shown in FIG. 1B, zero (touching the surface) or negative (submerged below the surface) as shown in FIG. 1E. For the parallel pin geometry shown in FIGS. 1A, 1B, 1C, 1D and 1E, the amount of particles collected relates to the separation H, at the time the voltage is applied. In general, the amount collected is larger, for smaller positive H, and larger still for negative H, as shown graphically in FIG. 2A. Depending on the geometry, dielectric properties of the particles, voltage, etc., there is a maximum H, beyond which no particles are collected at all. With the various configurations described herein, collection has been achieved with an initial separation H of even as great as 400-500 microns.

Figure 2B:
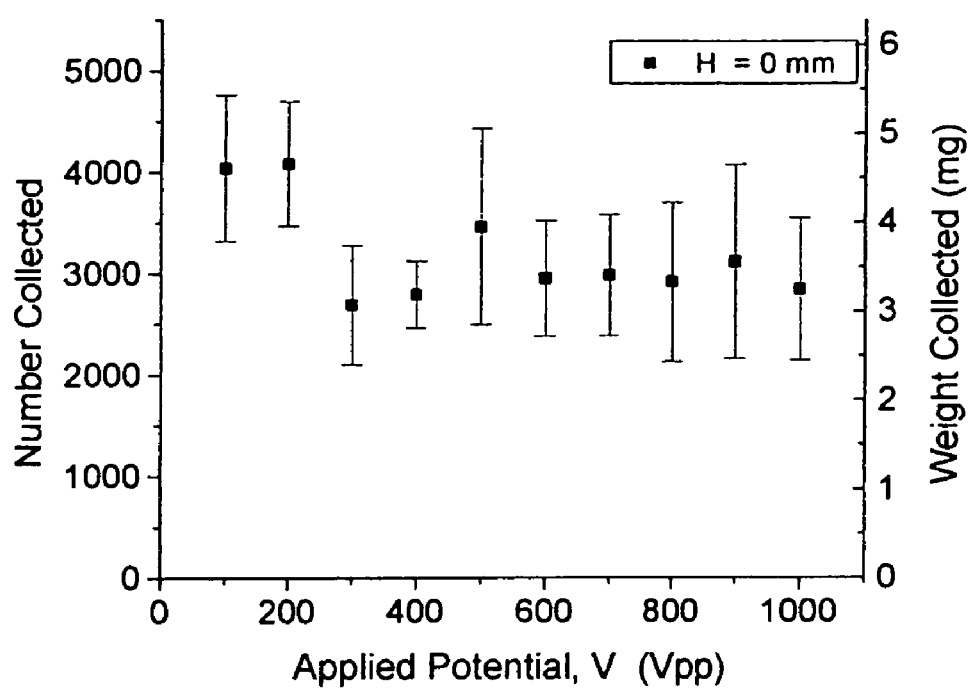
FIG. 2B is a graphical representation of the relationship between amount of material collected and voltage V, for a separation H=0, frequency of 50 Hz, for a two pin electrode such as shown in FIG. 1A, having a diameter of 2.5 mm.

Another parameter that can be varied is the applied voltage V, or, more particularly, the peak-to-peak difference, when AC operation is practiced. The amount of material collected for this two pin configuration, varies somewhat with the applied voltage, as shown by FIG. 2B. The variation is essentially linear, or only slightly greater than linear. Thus, other things being equal, an operator would likely opt to use the lowest voltage that provides acceptable results.

Another parameter that can be varied that has an appreciable effect on the amount of particles that are collected is the spacing w between the pins 5110a and 5110b of an electrode pair 5110. In a typical case, as the spacing increases, the field strength decreases and the field becomes less localized in the region between the pins, so that fewer particles are collected. Above a certain maximum spacing, the strings break, and no particles are collected. The spacing of an electrode pair can be fixed, and different pairs, with varying spacing may be used. Alternatively, as shown schematically in FIG. 1A, one of the pins 5110b can be located in a slot 5071, or other suitable fixture, with an adjustable locking mechanism (not shown), such as a set screw, vernier, or movable sleeve, so that for different collection runs, the spacing w can be altered by moving the pin 5110b to a different location within the slot 5071. Theoretically, if arcing can be prevented, it is believed that for very small separations (on the order of the diameter of a particle) the amount of material may increase with increased spacing w, until a maximum is reached, beyond which the amount decreases, as discussed above. However, in practice, it has been found that arcing arises at very small spacing w, and so no particles can be collected at all, for even small voltages.

Figure 3A:
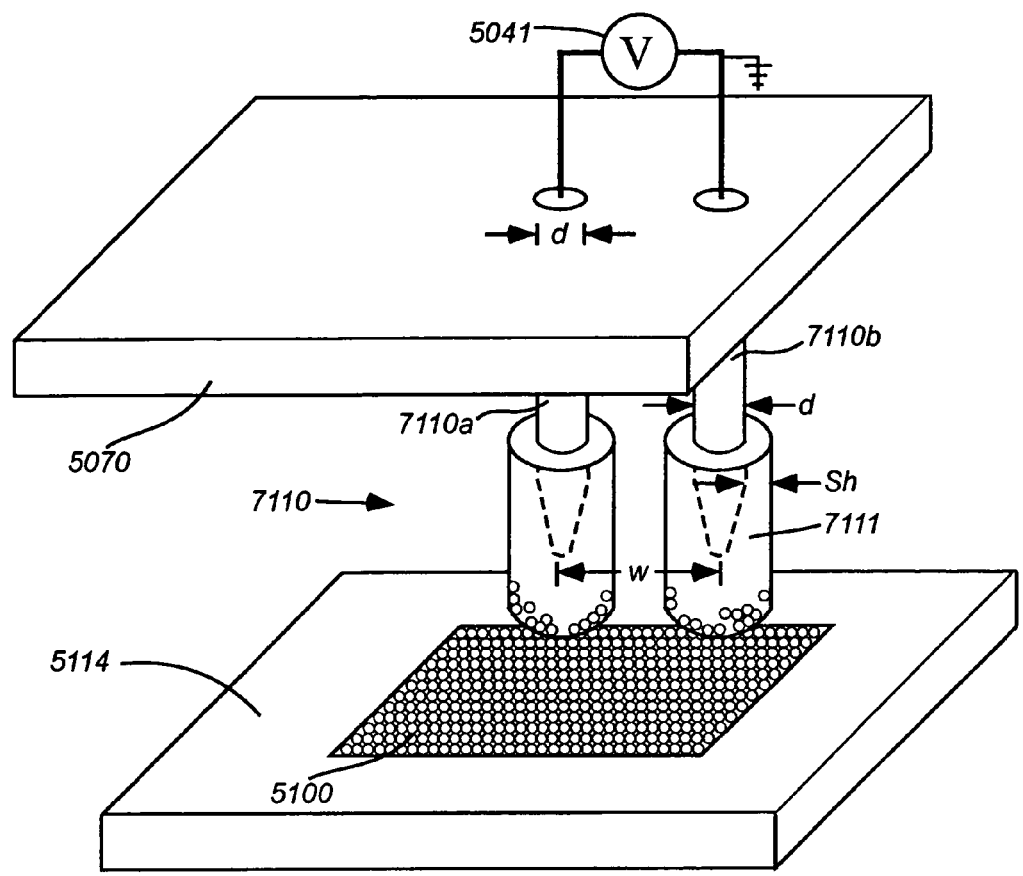
FIG. 3A shows, schematically in a perspective view, a two pin electrode, similar to that shown in FIG. 1A, with a dielectric sheathing around each of the pins.
Figure 3B:
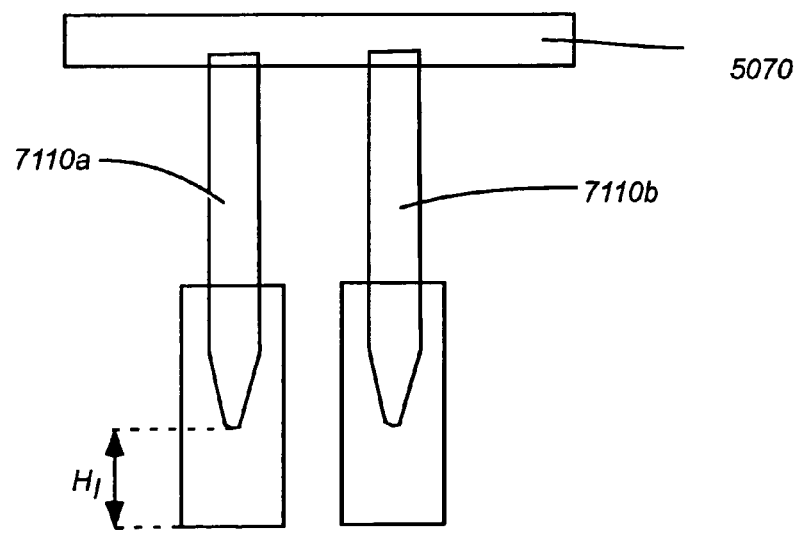
FIG. 3B shown, schematically, in a side view, the sheathed two pin electrode shown in FIG. 3A.
Figure 4:
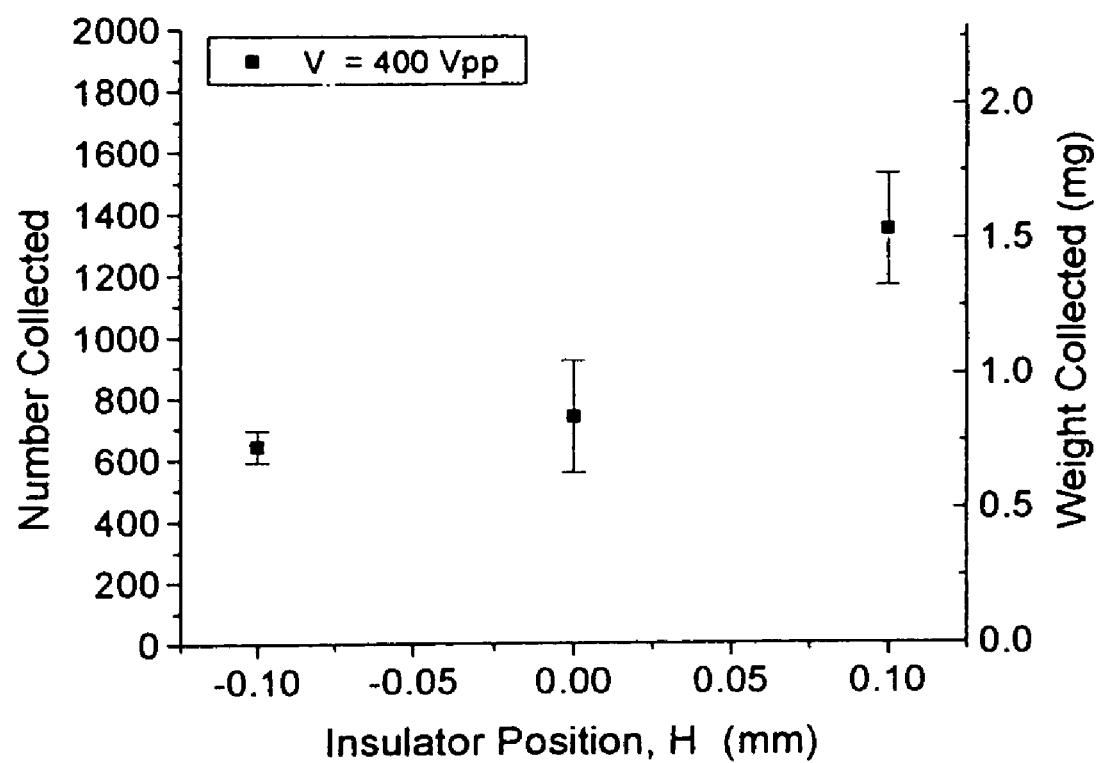
FIG. 4 shows graphically, the relation between weight of material collected and dielectric covering position, for pins having a separation w=2.5 mm, V=400 Vpp, where $H_I$ is the location of the pin tips relative to the ends of the covering, such that for $H_I>0$, the tips of the pins are exposed.

As shown in FIG. 3A, It is also possible to alter the amount of particles collected by providing the wire pins 7110a and 7110b with a dielectric covering 7111, such as a coating, or a sheathing, for instance similar to insulated electrical wire. In general, covering the wire pins with dielectric coating decreases the amount of material collected, other things being equal. FIG. 4 shows graphically, the relation between weight of material collected and dielectric covering position, for pins having a separation w=2.5 mm, V=400 Vpp, where $H_I$ is the location of the pin tips relative to the ends of the covering, such that for $H_I>0$, the tips of the pins are exposed. (FIG. 3A and 3B (side elevation) show $H_I<0$.) To some extent, the decrease will depend on the length of the pin that is sheathed, the thickness sh of the sheathing and the diameter d of the pins.

Several general considerations apply to systems for manipulating small amounts of micron scale items. First, the manipulating device must attract such items to it. Second, the items must be retained on the manipulating device during transportation of the items, or relative motion between the manipulating device and the item support. Third, the items must be removable from the manipulating device. At some point, it is important to know with the desired degree of precision how much material is being manipulated. An ideal situation would be to attract a precise quantity of material to a manipulating device, to have all of it adhere to the device as it is transported, and then to remove all of the material from the manipulating device. However, this is not absolutely required. For instance, if the amount of material that is attracted and retained is known to be within a certain range, with some precision, and the amount can be measured upon final deposit with great precision, this would be adequate for many applications. Similarly, if some, but not all of the material that is attracted to the device is retained, but all of it may be measured, and then all of it removed from the device, this too would be adequate for many applications.

It is also possible for there to be various ways in which the material is retained on the transporting device. It may be retained, for instance, by maintaining a certain voltage. The powder may also be retained without any voltage being applied, for instance, by adhesion forces, only.

Similarly, there are various ways to remove the material from the transporting device. A voltage may be removed, which in some cases causes all of the material to be removed. In other cases, (typically, only if the electrode has a dielectric covering) the polarity of the applied voltage is reversed, which repels certain charged material (with a like polarity) from the manipulating device. In other cases, some agency is applied to draw the material from the transporting device. For instance, the device can be submerged into a liquid, which washes the material from the device. Or, the device can be brought into proximity with a target that has a specific voltage, or a surface charge that also draws the material to it, away from the transporting device. Further, the transporting device, and retained material, can be brought under the influence of another electric field, which applies a force to the retained material, removing it from the transporting device, and directing it toward a target. Combinations of the foregoing can also be applied to insure complete removal of the material from the transporting device.

Various methods and apparatus for drawing material to a transporting device, retaining the material and transporting it, and then releasing it, are explained below.

Forces on Dielectric Bodies

Additional apparatus and methods are described below. At this point, a brief theoretical discussion of the forces exerted on a dielectric body is helpful. Without being limited to a particular theory, it is believed that the apparatus described in the foregoing section draws particles to it by virtue of a gradient in electric field and the resulting forces that are created on dielectric bodies.

A dipole is induced in a dielectric material in the presence of an electric field. By "dielectric" material, it is meant generally, a non-conductor of direct electric current, which is quantified by having a conductivity less than approximately $10^{-9}$ $(\Omega \cdot cm)^{-1}$. The electric field between two flat parallel plates that are oppositely charged, or that have a uniform potential difference, is spatially uniform (except, of course, at its edges), with field lines extending perpendicularly to each plate and parallel to each other, from one plate to the other. Such a field has a zero spatial gradient throughout most of its extent. The net polarization of a dielectric body in such a field will tend to be parallel to the electric field lines, with the net dipole moment of the body directly opposite to the electric field vector. Therefore the force on the positive charge of the dipole will be equal to the magnitude of the force on the negative charge, and in a uniform field there will be no net force on the body. Such a dielectric body will experience a net force in a uniform electric field only if the body has a net static surface charge. In this case there will be a Coulombic force on the body in the direction of the field (for a positive surface charge) and proportional to the net surface charge. The motion of a charged body in a uniform DC field is referred to as "electrophoresis." Known techniques in the field of particle manipulation typically exploit such Coulombic force to manipulate granular dielectric material. Electrophoretic processes of this nature require precisely controlled charging of the particles prior to manipulation in order to achieve a specified surface charge. Such processes also require very precise control of the surrounding environment throughout the process, as slight changes in the relative humidity have a significant effect on the surface charge.

The polarization of a dielectric body in the case of a spatially non-uniform electric field will also be parallel and opposite to the electric field lines, and the body will develop a net dipole with equal positive and negative charge separated by a certain distance. However, in contrast to the uniform field case, in a non-uniform field, the total magnitude of the electric force on the positive charge will be different than the force on the negative charge because of the spatial variation of the field. Therefore the body will experience a net dielectrophoretic force proportional to the product of the spatial gradient of the field and the net dipole moment of the body.

This dipole moment is also proportional to the magnitude of the applied field, so that the total dielectrophoretic force is a function of the gradient of the square of the electric field. This force is independent of any surface charge present on the dielectric body, and as described below is a function only of the magnitude and shape of the electric field, the size of the body, and the difference in polarizability between the body and the surrounding medium.

Figure 5A:
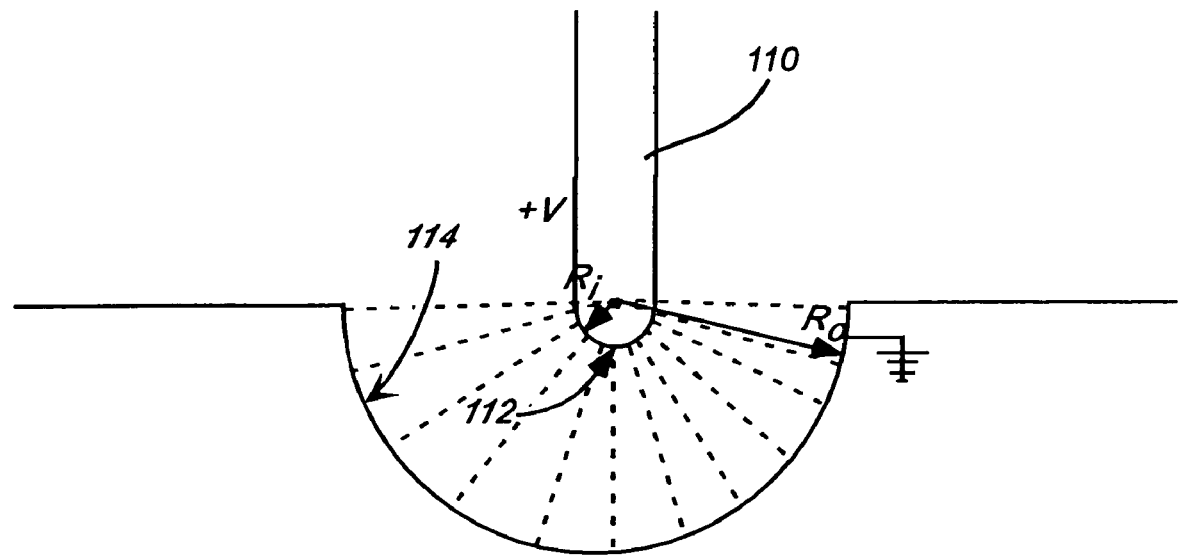
FIG. 5A is a schematic representation in plan view of an elongated electrode, and the lines of an electric field generated thereby for an idealized spherical geometry.

An example of a spatially non-uniform field is shown schematically in FIG. 5A. An elongated electrode 110, with a spherical tip 112, aligned concentrically with a spatially extended electrode, such as a semi-circular plate 114 that extends around the tip of the elongated electrode 110, gives rise to a spatially non-uniform field, with field lines that converge upon the tip 112 of the elongated electrode, and diverge toward the plate 114, perpendicular to the surface. The field lines shown are idealized, and are not calculated. Similarly, in three dimensions, a cylindrical rod with hemi-spherical tip, surrounded by a hemi-spherical extended plate would generate a field characterized by lines that emanate from the center of the tip, toward the surface of the spherical plate. Dielectrophoretic force is discussed generally in (R. Pethig, G. Markx, "Applications of Dielectrophoresis in Biotechnology," Tibtech 15 (1997): 426-432), which is incorporated fully herein by references.

A non-uniform field may be generated by two or more electrodes, where the distance between any two facing surfaces of the electrodes is large compared to the extent of either facing surface, in any one dimension. The surfaces can be flat or non-flat. Such fields can also be generated by an electrode and a surface charge, as will be discussed in greater detail below. A non-uniform field is also generated at the edges of facing flat plates, which otherwise have a generally uniform field therebetween. The non-uniform field can be exploited to manipulate items, as discussed below, and the presence of a uniform field between the plates does not preclude such exploitation. Even more generally, a spatially non-uniform field is generated near an electrode surface that either has a small spatial extent, or a small radius of curvature, in at least one dimension, compared to the spacing between the electrode and a counter electrode. Thus items are subjected to a non-uniform field created either by a sharp edge (small radius of curvature in one dimension), a hemispherical tip (such as the elongated electrode tip 112 shown in FIG. 5A),) (small radius of curvature in two dimensions), or a "point like electrode", (such as 210, shown in FIG. 5D, discussed below which has a small facing surface compared to the spacing to the counter electrode 216). Any of these geometries for generating a non-uniform field can be exploited to manipulate dielectric items, as discussed below.

When many dielectric bodies are simultaneously subjected to an electric field, they become polarized by the field. Once polarized, the particles will tend to move together due to the interaction of their dipole moments. This polarization force causes a particle which is attracted to the collecting electrode to pull a chain of polarized particles with it, creating strings of particles along the field lines.

Dielectric bodies also experience surface adhesion forces due to van der Waals interactions and hydrogen bonding. Van der Waals forces are exerted between any two objects, such as the dielectric particles described here, as well as between the particles and other objects such as the substrate holding the particles before collection, the collecting electrode, and target substrate. These forces scale inversely with separation, and generally tend to become more important for small separations and small particle sizes. Capillary forces that cause the particles to adhere to surfaces occur when water condenses on these surfaces, for example at the particle necks. These forces are generally more important for hydrophilic surfaces and higher relative humidity.

Dielectrophoretic Force Calculation

Figure 5B:
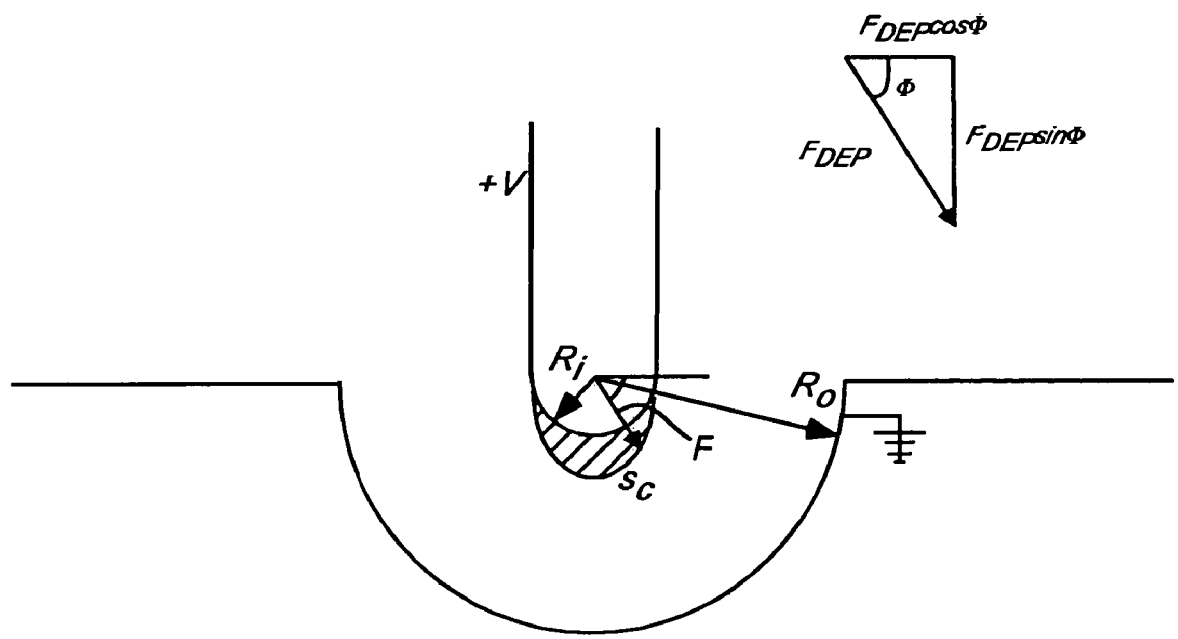
FIG. 5B is a schematic representation showing the maximum volume from which material can be collected for a given voltage, assuming that this volume is filled with material to be collected at the time voltage is applied.
Figure 5C:
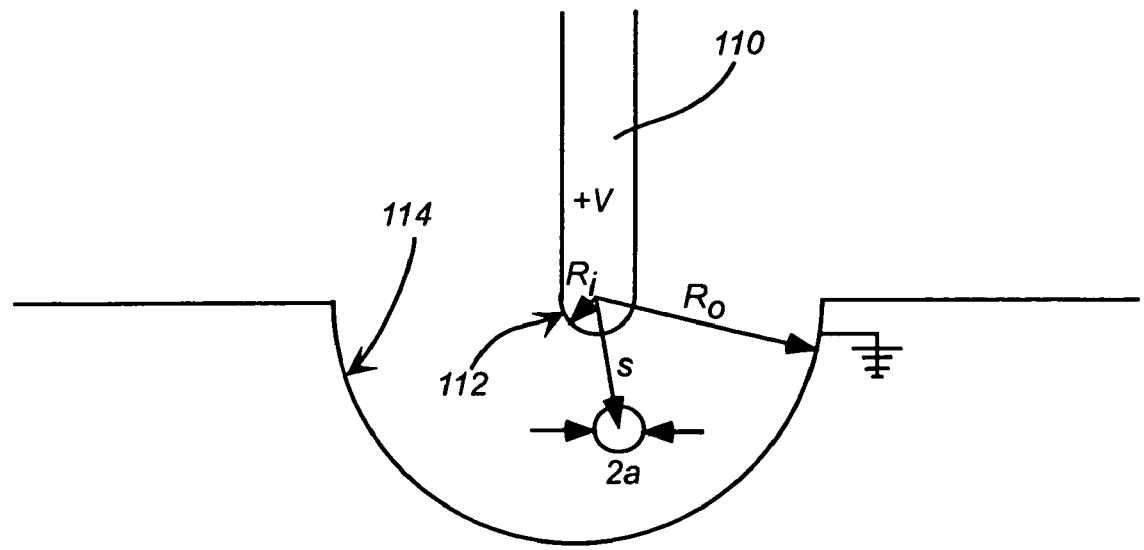
FIG. 5C is a schematic representation in plan view of an elongated electrode with an idealized spherical geometry and a particle to be manipulated by the electrode.

FIG. 5C shows an idealized apparatus configuration essentially identical to that shown in FIG. 5A. A generally cylindrical electrode 110, with a spherical end 112, having a radius $R_i$ is presented with a positive voltage V, and is spaced a distance $R_o$, from a grounded, shaped particle support electrode body 114, having a semicircular surface 116, with a radius $R_o$.

With reference to FIG. 5C, the dielectrophoretic force, $F_{DEP}$, on a spherical particle 100 of radius a located a distance s from the electrode 110 is given by:

$$F_{DEP} = 2\pi\epsilon_1 a^3 K \nabla(E^2), \tag{1}$$

where $\epsilon_1$ is the permittivity of the surrounding medium, (between the manipulating electrode 110 and the support electrode 114) and $\epsilon_2$ (below) is the permittivity of the particle 100. (Pethig, cited above.) The constant K is given by:

$$K = \frac{\varepsilon_2 - \varepsilon_1}{\varepsilon_2 + \varepsilon_1}. \tag{2}$$

(Hence, if the permittivity of the particle is greater than that of the medium, the force is positive, and if vice versa, it is negative.) The gradient of the square of the electric field magnitude (dot product of the field), $\nabla(E^2)$, for the idealized geometry of FIG. 5C, is given by:

$$\nabla(E^2) = \frac{2R_o^2 R_i^2 V^2}{s^5 (R_o - R_i)^2}. \tag{3}$$

(This expression is for a three dimensional geometry, with an axis of rotational symmetry along the long axis of the elongated manipulating electrode 110.) (R. Pethig, G. Markx, "Applications of Dielectrophoresis in Biotechnology," Tibtech 15 (1997): 426-432.)

Collecting

Figure 5D:
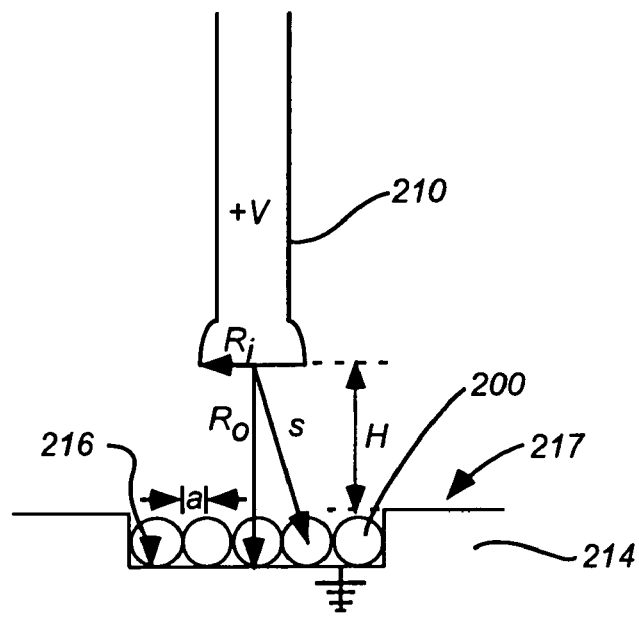
FIG. 5D is a schematic representation in plan view of an elongated electrode and a number of particles to be manipulated, supported in a recess of a spatially extended electrode.

A simplified geometry that is useful for explanation and proof of concept is shown schematically in FIG. 5D. A generally cylindrical, elongated manipulating electrode 210 with an enlarged end 211, has a radius $R_i$ and is spaced a distance $R_o$ from a grounded particle support electrode 214, which has a flat surface 216 that forms a well in a larger surface 217. Spheres 200 having radius a are spaced a distance s from the surface of the manipulating electrode 210. This actual situation can be roughly modeled with the idealized one shown in FIG. 5C, assuming for approximation that the origin of the radius s is within a spherical end portion of the elongated electrode 210.

For a=50 micron silica (glass) spheres, Equation 3, along with the parameters summarized in table 1, provides a rough estimate of the dielectrophoretic force on the spheres 200. The resulting value is approximately 7 μN.

TABLE 1

| Parameter | Value |
| --- | --- |
| a (m) | 5e−5 |
| $\epsilon_1$ (F/m) | 8.86e−12 |
| $\epsilon_2$ (F/m) | 3.37e−11 |
| K | 0.584 |
| $R_o$ (m) | 0.0022 |
| $R_i$ (m) | 0.001 |
| s (m) | 0.00025 |
| V (V) | 500 |

The apparatus shown is used to lift particles against the force of gravity. The dielectrophoretic force must be larger than the gravitational force, to lift the sphere. The gravitational force, $F_G$, acting on a sphere of radius a and density ρ, is given by:

$$F_G = \frac{4}{3}\pi a^3 \rho g. \tag{4}$$

The gravitational force calculated using the parameters listed in Table 2 (below) is 0.012 μN, which is much less than the estimated dielectrophoretic force. This confirms that the dielectrophoretic force is large enough to cause 100 micron diameter silica spheres at a distance of 200 micron from the manipulating electrode, to be lifted from a support and collected at the electrode 110. This agrees with observations.

TABLE 2

| Parameter | Value |
| --- | --- |
| A (m) | 5e−5 |
| ρ (kg/m³) | 2.18e3 |
| G (m/s²) | 9.81 |

Collection Zone

To determine the effect of varying the applied voltage, V, the idealized spherical geometry was used to determine a critical distance $s_c$ such that for $s \leq s_c$, $F_{DEP}\sin\phi \geq F_G$, and particles may be held against gravity, where φ is the angle from horizontal to the $F_{DEP}$ vector, as shown in the force diagram of FIG. 5B. The following is a simplified discussion used only to illustrate the scale of the capture region. It neglects the affects of the particles themselves on the field, as well as friction, adhesion, etc., between particles. Thus the total collection volume, CV, is given by equation 5, and is shown schematically in FIG. 5B. This is the total volume that may be filled up with spherical particles that will be collected. Particles that are initially outside this region will not be collected, as the dielectrophoretic force is too weak to overcome gravity.

$$CV = \left(\frac{2}{3}\right)\pi(s_c^3 - R_i^3) \tag{5}$$

If the packing density of the collected spheres within this volume is ~60%, then the total mass collected will be given by Equation 6, where ρ is the density of the spheres.

$$\text{Mass} = 0.60 \times CV \times \rho \tag{6}$$

Combining Expressions 1, 2, 3, 4, 5 and 6 results in an expression that relates the mass that would be collected to voltage, V as follows.

$$\text{Mass} = 0.40 \times \rho \times \pi \left[\left(\frac{6\varepsilon_1 R_o^2 R_i^2 V^2}{\rho g (R_o^2 - R_i^2)}\right)^{\frac{3}{5}} - R_i^3\right] \tag{7}$$

Figure 6:
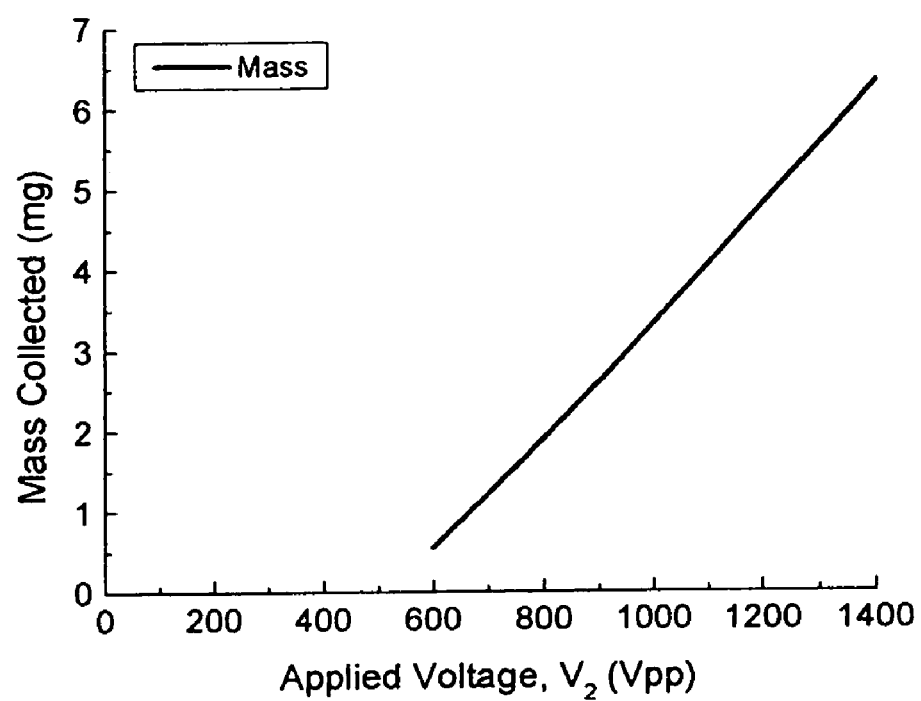
FIG. 6 shows graphically the relation between maximum mass of material collected, and voltage, for an electrode set up such as is shown in FIG. 5C.

The maximum weight that may be collected, if the entire collection volume is filled, can thus be calculated as a function of applied voltage. The results of such a calculation, using Eq. 7, are shown graphically in FIG. 6.

Over the voltage range of 600-1400 volts, for which $(R_i+a)<s_c$ $(\phi=0)<(R_o-a)$, the amount collected only varies from approximately 1 to 8 mg. This suggests that to significantly change the amount of powder collected, the designer would choose to change the size or shape of the electrode rather than relying on changing the voltage. This accords with experience. However, within an order of magnitude, variations can be achieved by changing the voltage for this type of electrode configuration.

Thus, whether a given particle, or item, will be attracted to and then picked up by a given electrode depends on a number of factors. In the first instance, if the distance between the item and the manipulating electrode is less than $s_c$, the item will be attracted, and picked up. If the distance is greater than $s_c$, the item still might be close enough to be pulled toward the electrode, along the surface of the other items, or the support surface upon which the items rest, but that is very difficult to predict.

The critical distance depends on the applied voltage, the shape of the manipulating electrode, 110, and its tip, the shape of the support electrode 114, the mass of a representative item to be collected, the size of such an item, and the permittivities of the items and the surrounding medium. The operator is typically interested in the total mass of material to be collected, not its distance from the electrode. The mass of material picked up depends on the critical distance, the density of the items, their size, and also the packing density of the particular collection of items.

Because the amount of material picked up depends on the packing density of the material, it is typically helpful to control, or to know that density. One way to accomplish this is to provide the particles at a uniform density, for instance, their tap density. This will help to provide a uniform packing density throughout the powder bed, giving the best reproducibility.

Figure 1F:
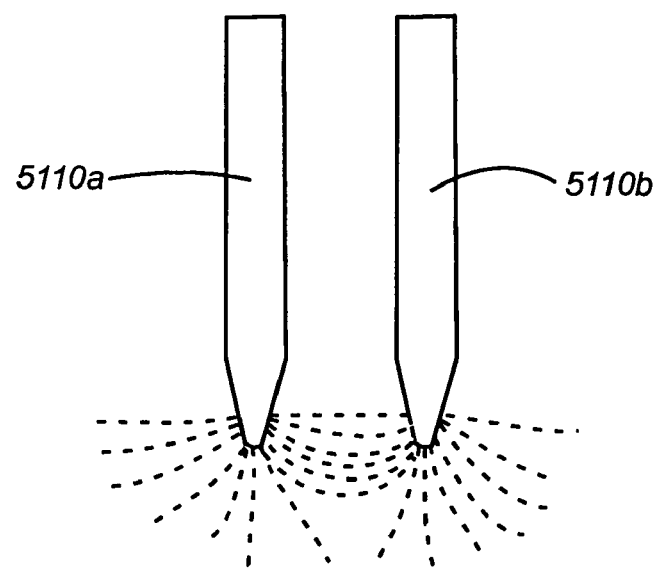
FIG. 1F shows schematically electric field lines that would be generated by a parallel pin electrode such as shown in FIG. 1A.

Every electrode shape, and field configuration gives rise to its own critical distance, and critical volume. For instance, the parallel pin electrode configuration, shown in FIG. 1A, has a different critical volume than does the single pin and spatially extended plate electrode of FIG. 5B. With the parallel pin electrode, the field lines extend between the pins, directly, and surround each, diverging away from the pins. A schematic representation of the field lines generated by such a configuration is shown in FIG. 1F. The shape of the field is different if the pins are spaced further apart. At some maximum spacing, the dielectrophoretic force at the midpoint between the pins is too weak to hold the particles against gravity, and particles can not be collected.

Without being limited to a particular theory, the maximum spacing is believed to be on the order of the distance from the terminal end of the pins to any ground beyond the particle bed, such as a portion of the support 5114, shown in FIG. 1B, or whatever hardware is beneath it, depending on where a ground potential exists. It is believed that this is because, at that spacing, the presence of the ground beyond the particles begins to have an influence on the field, which is on the order of the influence played by the other pin electrode. This significantly changes the shape of the field, such that particles are no longer retained between the pins.

Field and Gradient of Square of Field

Expression 1 above indicates that a dielectrophoretic force will be proportional to the gradient of the square of the magnitude of the electric field in which a dielectric particle resides. This force then depends to a large extent on the geometry of the manipulating electrode. Significantly, it will not depend on the polarity of the electric field. Also significantly, it will not depend on the surface charge of the item to be manipulated within the field. In general, the gradient of the field squared will be higher near to sharp portions of the electrodes that give rise to the field, for instance, the tips of the pins 5110a and 5110b of FIG. 1A. Thus, it would be expected for particles to be drawn to such sharp regions. This accords with observations. See, for instance, FIG. 1C, showing particles attracted to the tips of the pins.

Manipulated Items Need not be Charged

For dielectrophoretic phenomena to be exploited it is not required that the object to be manipulated be charged. Inspection of expression 1 reveals that the charge of the item to be manipulated does not contribute to dielectrophoretic force. It is required that the manipulated item be composed of a dielectric material. The foregoing should not be confused with an understanding that the surface charge of the item to be manipulated will have no effect on how the item behaves under all circumstances. For instance, if the applied electric field has a DC component, the surface charge may give rise to an electrophoretic force that will contribute to the total force on the item. However, that will not affect the dielectrophoretic force itself.

Dielectrophoretic Force insensitive to Polarity of Field

The electric field that exists between the elongated electrode 110 and the plate 114 can be DC (constant) or AC (alternating). It is important to note that the dielectrophoretic force, given by Expression 1, goes as the gradient of the square of the field, $\nabla(E^2)$. The magnitude of the force does not depend on the polarity of the field. The direction of the force also does not depend on the polarity of the field. Thus, AC voltages can be used to activate the manipulating electrode. This has advantages, as discussed below. The magnitude of the force will be largest where $E^2$ changes (spatially) the most rapidly. Without being limited to a particular theory, it is believed that this is near to sharp portions of the manipulating electrode 110.

As discussed below, an invention disclosed herein can be used to manipulate micro-electronic components. One benefit of using the disclosed invention for manipulating micro-electronic parts is that they need not be charged. Charging some such items could damage them. Further, for such a use, it is also beneficial to use an AC field, because the components are less prone to being harmed or affected by such an AC field, although they might be by a DC field of a similar magnitude.

Retention of Items on the Manipulating Device

Both charged and uncharged particles may be retained on the electrode against the force of gravity by the dielectrophoretic force resulting from the applied voltage. A DC voltage, or a DC component to the AC voltage may cause an additional Coulombic force to retain the items if they have a substantial surface charge opposite in polarity to the applied DC voltage. When the voltage is removed, particles may be retained on the electrode by van der Waals adhesion forces, as well as capillary forces due to condensed water on the surfaces or at the particle necks. The relative magnitude of the dielectrophoretic force, Coulombic force, adhesion forces, and the gravitational force will depend largely on the size and dielectric characteristics of the items, as well as the relative humidity of the surrounding environment. In general, high humidity will act to reduce Coulombic forces. Also, surface adhesion forces and Coulombic forces will tend to be more dominant relative to gravity for smaller particle sizes. This means that larger particles will be more likely to fall as soon as the applied voltage is removed, whereas additional means may be necessary to remove smaller particles.

Reproducibility of Dielectrophoretic Phenomena

When collecting very small amounts of very small size particles, particularly in connection with pharmaceutical doses, it is important that the equipment have highly reproducible behavior. Collecting small items using the dielectrophoretic effect is highly reproducible, because the factors that govern it are very stable in normally encountered situations.

For instance, the permitivity $\epsilon$ of the medium surrounding the electrode and that of the item being manipulated are very stable, and relatively insensitive to any typical environmental parameters that vary somewhat over the normal time period of a manufacturing run, such as, primarily, humidity, and, perhaps to a lesser extent, temperature. The density of the particles being manipulated is constant, and the packing density of the particles and the electric field can be made very stable. The other parameters (radius a of the particle, on average, and the geometrical features of the elongated electrode and support surface) are constants. Thus, the average amount collected for a given powder and set of operating conditions can be established with great precision. As discussed above, the amount collected can be controlled by selecting the various factors that establish the collection zone, such as: the configuration of the elongated electrode, the applied voltage, and the distance of the elongated electrode tip from the particle surface. These are constant, or highly reproducible.

Some known methods and apparatus manipulate items that are charged. Those methods require uniformly and reproducibly charging the items to be manipulated, so that the process is itself reproducible, and the amount collected or deposited can be tightly controlled. However, the charge upon small items is hard to control in some circumstances, and is typically sensitive to the humidity of the environment in which the manipulation takes place.

It has been found that in some circumstances, using an invention as disclosed herein, such as in FIG. 1A (pins) or 7A (loops, discussed below), when it is more humid than a maximum humidity, it is difficult to collect certain types of particles. When the manipulating electrode is moved away from the particle bed more than a certain distance, the particles fall from the electrode and are not retained. Without being limited to a particular theory, it is believed that above such a humidity, adsorbed moisture at the necks between particles gives rise to an adhesion force that is large enough to prevent them from being pulled apart by the dielectrophoretic force. For instance, for silica spheres of approximately 70-100 microns, a relative humidity of above about 60-70% and at the most, about 80% impedes particle retention and collection. However, below that humidity, particle collection is reproducible, and essentially unaffected by humidity.

In partial summary of the foregoing, an invention disclosed herein uses manipulating electrodes that are elongated, or protruded from an electrode support. This shape gives rise to a markedly non-uniform field, which generates dielectrophoretic forces if applied to a dielectric material. Such dielectric items are attracted to regions of concentrated field, particularly the electrode, if a voltage is applied thereto. The applied voltage may be DC, or, AC. The items to be manipulated need not be charged, and, in fact, even if they are charged, dielectrophoretic forces dominate any charge-based forces. The items may be transported to a recipient target and deposited, either by removal of the applied voltage, or through the application of a force that pulls the particles off of the electrode. This may be the capillary force of a liquid contained in the wells of the recipient substrate, a dielectrophoretic force generated by electrodes on the substrate, or, a Coulombic force generated by a surface charge distribution on the target. Or, for charged items, a Coulombic force generated by an electrode or surface charge distribution opposite in polarity to the charge on the items to be deposited.

Shape of Manipulating Electrode Elongated Electrode

It is important that the manipulating electrode gives rise to a spatially non-uniform field and provides the opportunity to take advantage of a dielectrophoretic force. An elongated, or protruding electrode, with a relatively sharp point, and a counter electrode that is generally planar, is one shape combination that does so. In general, without being limited to a particular theory, it is believed that such a field will arise with an electrode having two conducting elements such that the spatial extent of any facing surfaces in any one dimension is small, compared with the distance between them. (Facing flat plates do not fit within the foregoing generalization, but they also generate a non-uniform field at their edges, which can be exploited, as discussed below. Thus, it is expressly not a requirement that there not be any regions of uniform field.)

Furthermore, if items are to be attracted preferentially to one of the conducting elements, the conducting element to which items are to be attracted should be small, in any one dimension, compared to the dimensions of the other electrode. An elongated electrode and a counter electrode that is extended in two dimensions perpendicular to the dimension of elongation of the elongated electrode satisfy these criteria. Other electrode configurations do also, as described below. Some are elongated, and some are not. An elongated electrode has certain other advantages, independent of the field that it generates. For instance, it can manipulate items into, or that reside in, recesses.

The parallel pins embodiment shown in FIG. 1B also gives rise to a spatially non-uniform field. First, consider an individual pin, and any other conductor that is spatially extended in two dimensions and spaced from the pin within a distance that its influence can be felt. The surface of the pin that may face the extended conductor is very small in extent, much smaller than the usual millimeter-scale spacing between the pin and any such extended conductor. Therefore this gives rise to a spatially non-uniform field. For instance, considering the conductive plate 5114, the facing surfaces of the pin tip and the plate give rise to a non-uniform field because the facing surface of the pin is so small compared to the facing surface of the plate, as compared to the size in any one dimension of the pin end surface. Next, considering the two pins together, these two give rise to a spatially non-uniform field because the facing surfaces of the pins, essentially two thin rectangles along their lengths, have a small dimension (circumferentially), as compared to the distance between them (approximately w). Thus, they do not look like facing flat plates, and give rise to a spatially non-uniform field.

If the electrodes are very close to each other, then the parallel thin lines may act as parallel plates, and could generate a substantially uniform field within the small region directly between the facing surfaces.

Parallel Loops Elongated Electrode

Figure 7A:
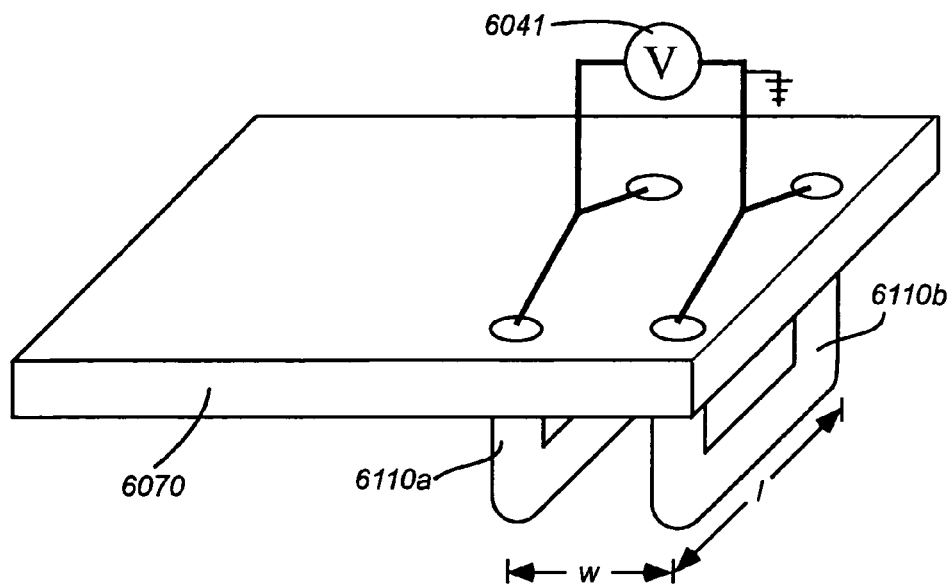
FIG. 7A shows schematically, in a perspective view, another elongated electrode, consisting of two elongated wire loops.
Figure 7B:
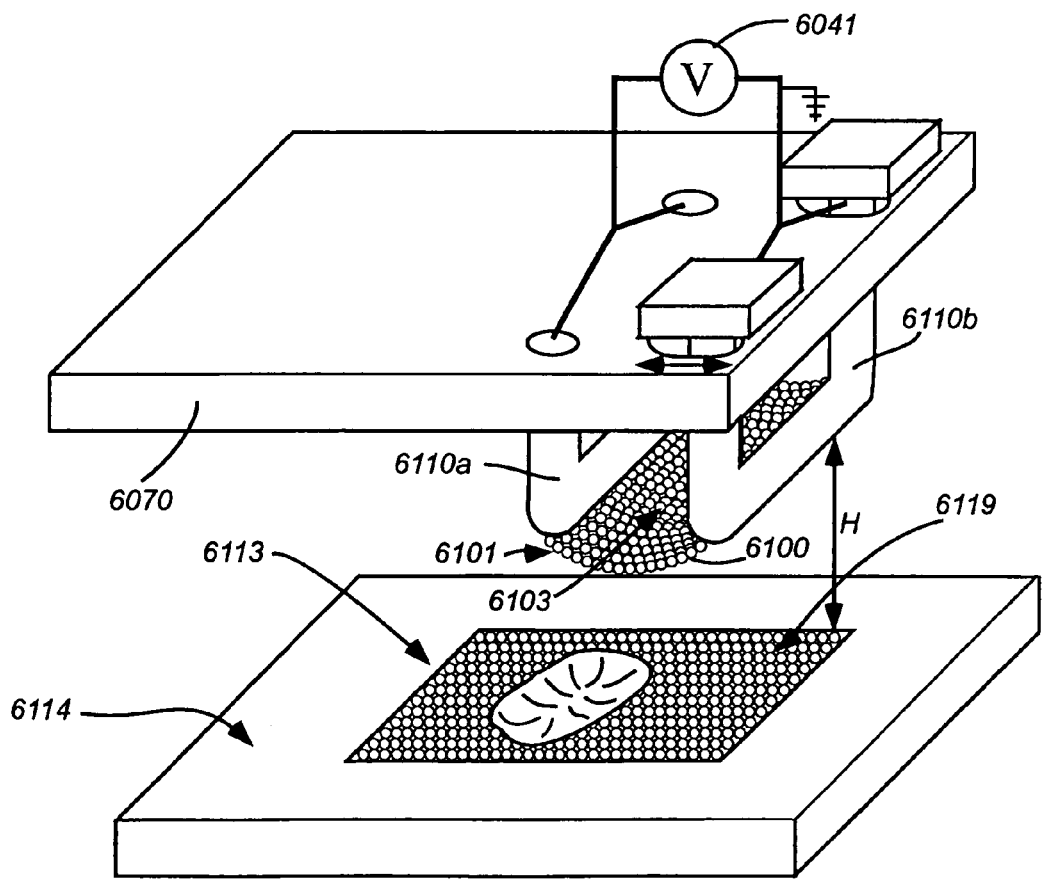
FIG. 7B shows the electrode of FIG. 7A, in the process of collecting dielectric items.

Another useful configuration for a manipulating electrode is shown in FIGS. 7A and 7B. It consists of two wires, 6110a and 6110b substantially parallel to each other and the surface 6119 of the particle bed 6113 along a length l. The particles are supported on an electrically isolated, conductive plate 6114. The wires 6110a and 6110b are separated from each other by a distance w and, initially, from the powder bed a distance H. Each wire is bent upward, substantially at a right angle at both ends, forming a substantially square loop. Each loop is secured to the electrode support 6070.

An AC voltage is applied between these two electrodes by connecting one loop 6110a to an AC power source 6041, and the other 6110b to electrical ground. To collect particles, the loops are initially placed at a separation H from the surface 6119 of the particles 6113 (analogous to that discussed above in connection with the pins, shown in FIG. 1B), and a voltage V is applied.

The electric field is localized around each wire, so that the particles are initially attracted to the surfaces of the wires. As additional particles 6100 are collected, they form "strings" 6101 between the two wire loops 6110a and 6110b. The strings extend between the wires, substantially the entire length l of the wires. Thus, the many strings of particles together form sheets 6103 of particles, which may be thought of as being draped between the long extents of the wires. It appears that there are a plurality of sheets stacked on top of each other over at least a portion of the region that sheets form (although this is not shown in FIG. 7B, for clarity). When the loops 6110a, 6110b are raised away from the particle bed 6113, the sheets 6103 of strings 6101 of particles remain between the electrodes 6110a and 6110b. The electrodes may then be moved over a recipient target, such as the well of a microtitre plate, where the particles are deposited by removing the applied potential.

It is useful to note that, in general, the presence of particles within the field changes the configuration of the field, typically concentrating the field lines at the locations of the particles. Thus the gradient is also generally increased by the presence of the particles. Thus, as particles are drawn toward the collecting electrodes, the field configuration changes, as does the force that it exerts on the particles themselves. The converse is also true. When the electrodes are pulled away from the surface of the particles, and some particles fall away, because the force is too weak to support the particle against gravity, adhesion to the other particles, etc., the field configuration changes, as does the force that it supplies.

Figure 8A:
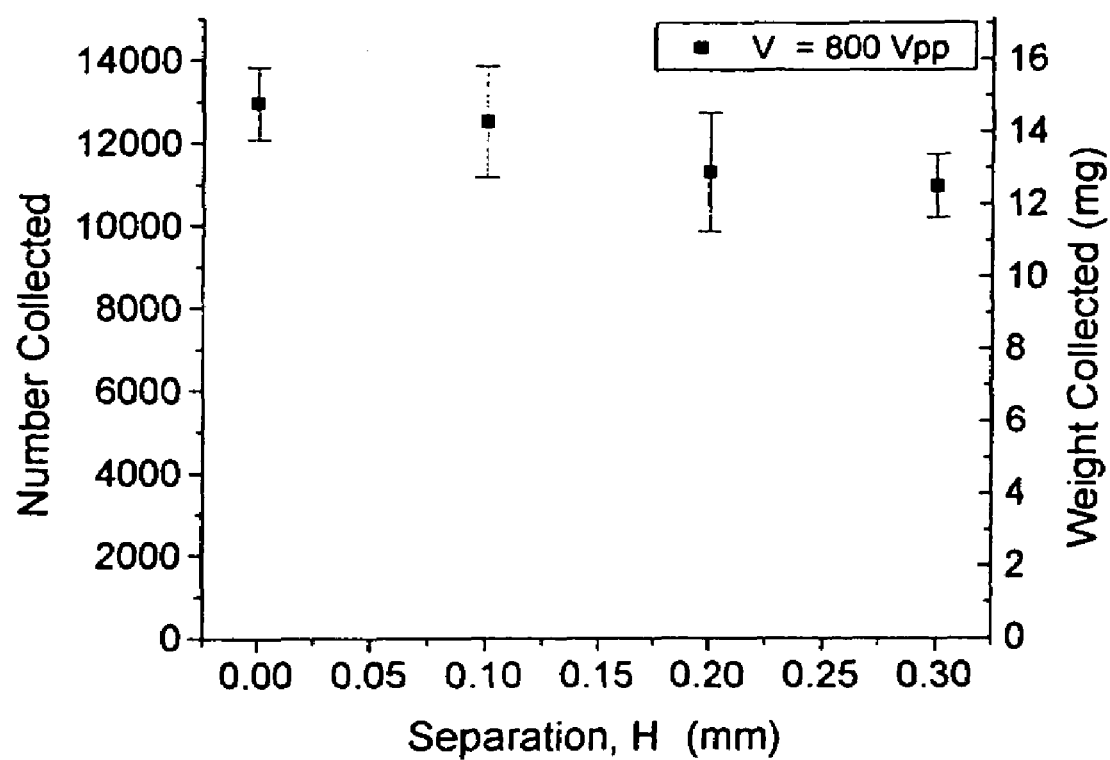
FIG. 8A shows graphically the relation between the weight of particles collected for a loop electrode such as shown in FIG. 7A, and initial height H above the particle bed, with w=1.8 mm between loops, l=2.5 mm length of loops, d=500 micron diameter of the wires, V=800 Vpp at a frequency of 50 Hz.
Figure 8B:
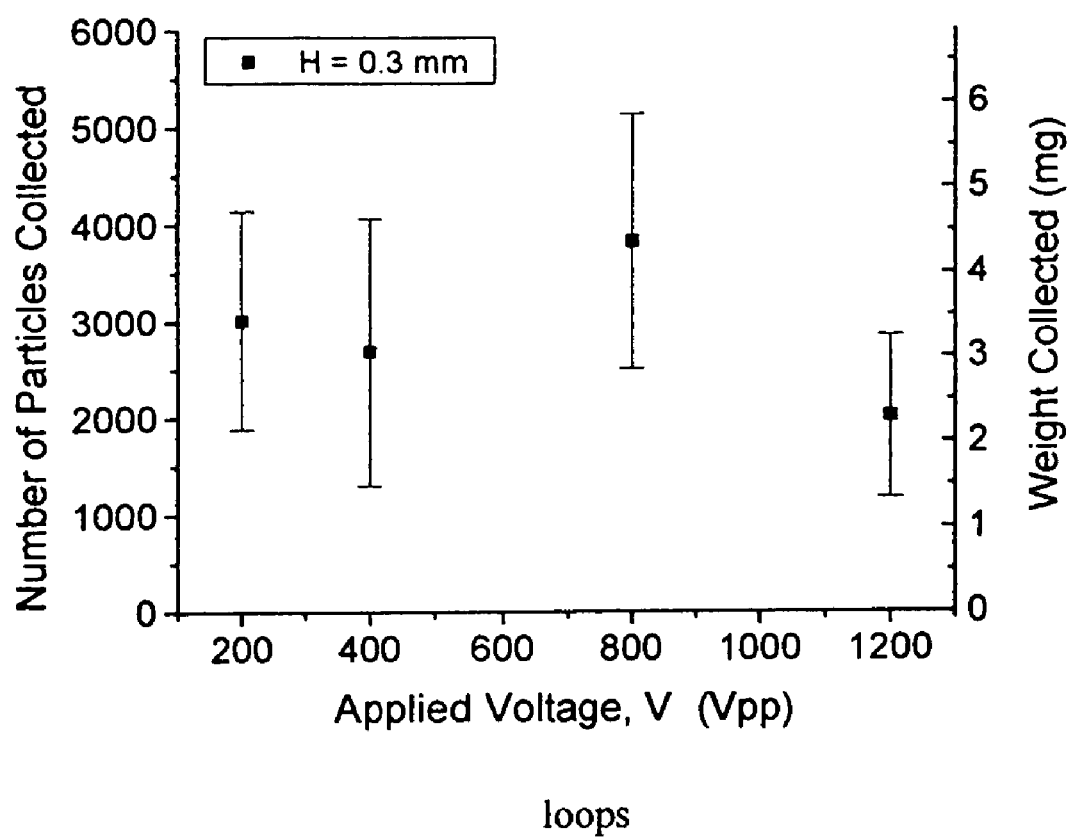
FIG. 8B shows graphically the relation between the weight of particles collected and voltage, for a loop electrode such as shown in FIG. 7A, sized as with FIG. 8A, with initial height H=0.3 mm.

For the loop geometry shown, having wires with a diameter d=0.5 mm, w=1.8 mm, l=2.5 mm, V=400 Vpp and humidity ~50%, the amount of powder collected decreases slightly from approximately 14.8 mg to 12.5 mg as the initial separation H increases from 0 to 0.3 mm. This dependence is shown by the graph in FIG. 8A. The amount of powder collected appears to increase slightly with applied voltage from 200 Vpp to 800 Vpp. The amount increases from 5.3 mg to 7.0 mg, as shown by the graph in FIG. 8B.

Figure 8C:
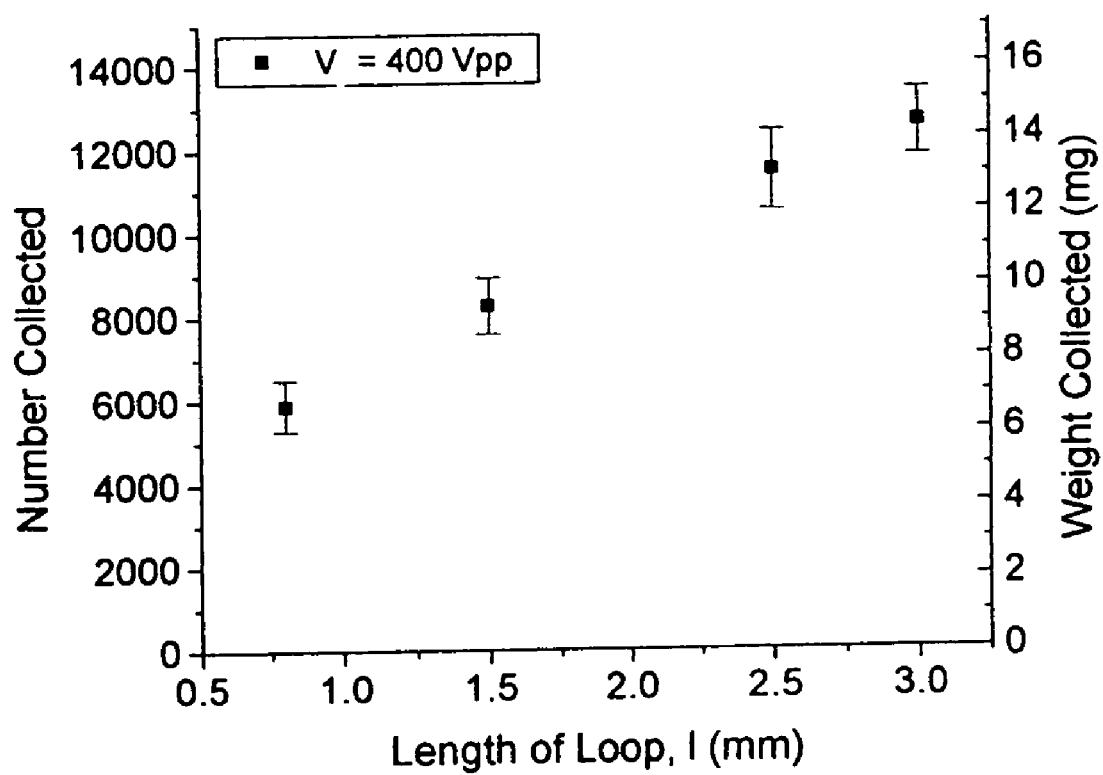
FIG. 8C shows graphically the relation between the weight of particles collected and length l of the loops, for a loop electrode such as shown in FIG. 7A, with initial height H=0, separation between loops w=2.0 mm and V=400 Vpp, humidity ~50%.

Like with the parallel pins, the geometry of the parallel loops has a strong effect on the amount of particles or items that can be picked up. In general, larger distance d between the wires results in smaller amounts of particles that are collected, up to a maximum spacing. At that maximum separation point, the wires become too far apart and, without being limited to a particular theory, it is believed that the field concentration at the center becomes too diffuse (the field lines will be most spread out) to support the center of the strings, or sheets (midway between the wires) and they do not hold. Thus, it is further believed that the gradient of the square of the field is small at these regions, because as the field concentration becomes more diffuse, its variation (spatially) also decreases. Larger diameter d of the wires does not have much effect on the amount of material collected, as compared to changing the separation between them w or the length l. Increasing the length l has an effect that is substantially linear with the increase, as shown graphically in with reference to FIG. 8C, for a loop electrode such as shown in FIG. 7A, with initial height H=0, separation between loops w=2.0 mm and V=400 Vpp, humidity ~50%. For each increase per unit length, a corresponding increase in weight of material collected arises.

To vary the distance w between the loops, it is possible to have removable loop pairs, with different, fixed separations w. These can be selected and installed as needed. Alternatively, a loop pair can be provided with an adjustable fixture, similar to that described above in connection with the parallel pins, for instance with the loop 6110b residing in a slot in which it can be fixed at different locations, as indicated by the double headed arrow. As with the parallel pins geometry, it is also believed that for very small distances between wires, about equal to a particle diameter, the amount of material that is collected is larger for larger separation, up to a maximum, assuming that arcing does not occur. However, arcing typically does occur at very small separations.

The paired loop electrode shown in FIG. 7A could also be provided with sheathing dielectric, in a similar manner, with a similar decrease in material collected. Again, in general, the reduction in collection will depend principally on the length of the loop that is sheathed, and the thickness of the sheathing.

The paired loop electrodes give rise to a spatially non-uniform field for similar reasons to why the pins electrodes give rise to a spatially non-uniform field. At their terminal ends, near to the particles, they appear like points, relative to the particle support, and thus give rise to a spatially non-uniform field. Along their parallel extents that are also parallel to the surface of the particles, as well as each other, they act both similar to the end points of pins, as described above, and also similar to the long portion of the pins, with facing semicircular surfaces. Both shape pairs give rise to a spatially non-uniform field.

Facing Plates as Elongated Electrodes

Figure 43:
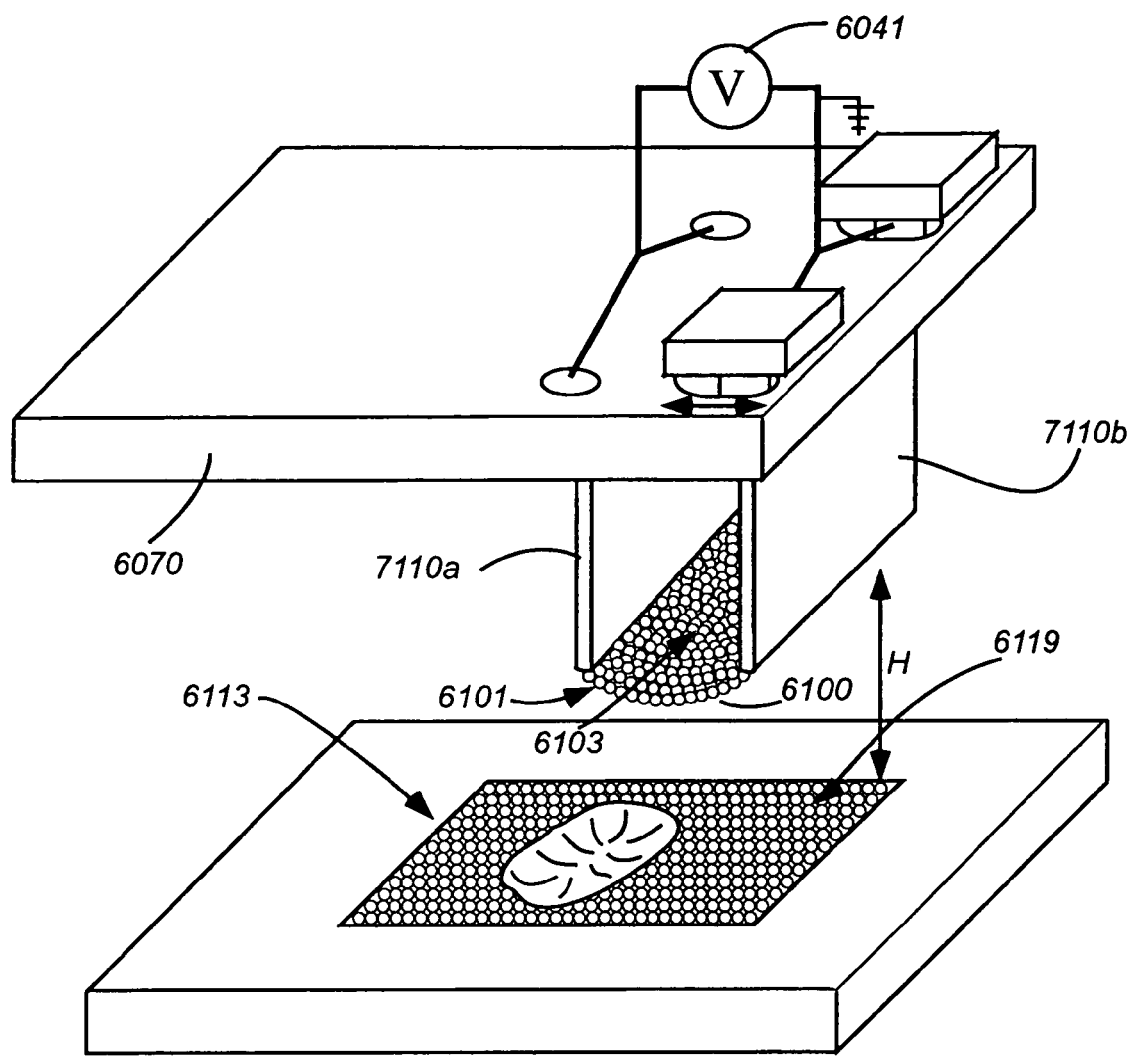
FIG. 43 shows, schematically, a parallel plate electrode, that can be used to collect items due to a non-uniform field at its edges.

It has been noted above that in general, a non-uniform field is generated between at least two electrodes, where facing surfaces of any two have an extent that is small, in at least one dimension, as compared to the distance between them. This is to contrast with a pair of flat plates, which will generate a uniform field therebetween, if they are large, in both dimensions, as compared to the distance between them. However, it should be noted that at the edge of any such facing flat plates, a spatially non-uniform field arises, generally extending into the space that circumscribes the plates, and the space between the edges. The non-uniform field can be exploited to collect items, despite the fact that the flat plates also generate a uniform field over a large region. This can be understood by referring to FIG. 43, which shows, schematically, a pair of flat plates 7110a and 7110b, that are facing each other in much the same was as are the parallel loops 6110a and 6110b shown in FIG. 7A. The plates generate a uniform field in the regions that are distant from the edges, and a non-uniform field near to the edges. Thus, the edges can be used to collect items, just as can the parallel loops. Thus, it is not a requirement that there be no uniform field region between the electrodes. Such a region will not contribute to picking up items by dielectrophoresis. However, those regions that contain a spatially non-uniform field do contribute to collection. It may, in fact, be useful for some applications to exclude collected items from the space between the plates, as would occur where the field is uniform.

Elongated Electrode with Disc and Ring

Figure 9A:
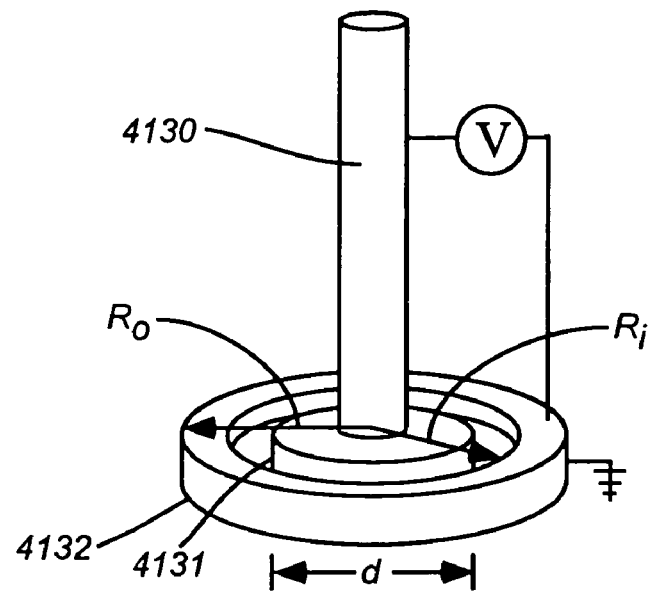
FIG. 9A shows schematically in perspective view an embodiment of an elongated manipulating electrode that can be used with the inventions, having an elongated rod, terminated with a disc, surrounded by a ring.
Figure 9B:
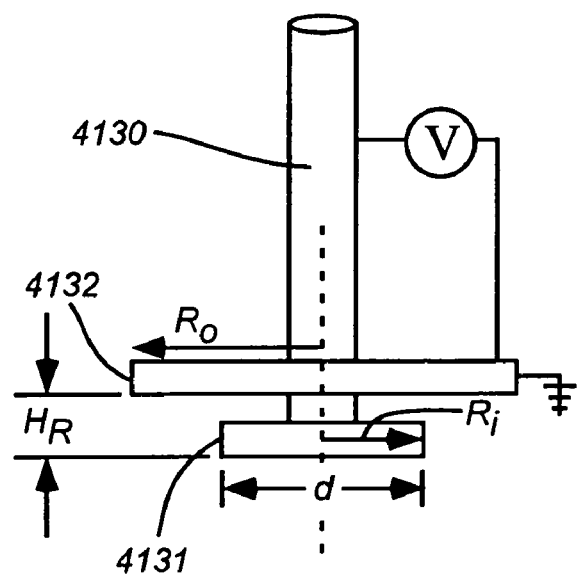
FIG. 9B is a schematic side elevation of the disc and ring manipulating electrode shown in FIG. 9A.

FIGS. 9A and 9B (side view) show, schematically, another type of elongated manipulating electrode 4110 having a beneficial configuration. This electrode is an elongated rod 4130, with a disc 4131. The terminal surface of the disc 4131 may be adjusted relative to the terminal surface of the ring 4132. The height of the ring above the terminal surface is denoted $H_R$ (FIG. 9B), such that $H_R=0$ when the two surfaces are coplanar as shown in FIG. 9A. The external ring 4132 is connected to ground (as indicated). An electrode spatially extended in two directions (not shown), is electrically isolated, and supports the items 200 to be manipulated, such as they are supported in FIG. 1B by the support 5114. A voltage is applied to the elongated rod 4130.

The applied voltage may be AC or DC. Thus, the field exists between the inner disc 4131, and the outer ring 4132. The particles are drawn to the regions of concentrated field, particularly at the outer edge of the inner disc 4131 where the gradient of the square of the field is high. The spacing between the disc and the ring, and the sizes of each (diameter of disc, inner and outer diameter of the ring) can be adjusted, depending on the size and dielectric constant of the particles to be collected, to collect particles at the disc edges, and in some cases, between the disc and the ring, in strands, analogous to that shown above with the parallel loops in FIG. 7B. It is a sort of circularly oriented version of the parallel wire loops embodiment.

As with the parallel pins and square loops configurations, the amount of material collected by the electrode depends on the initial separation, H, and the applied voltage, V. For this configuration, though, another parameter that may be varied to adjust the amount of material collected is the size of the disc, d.

Figure 10A:
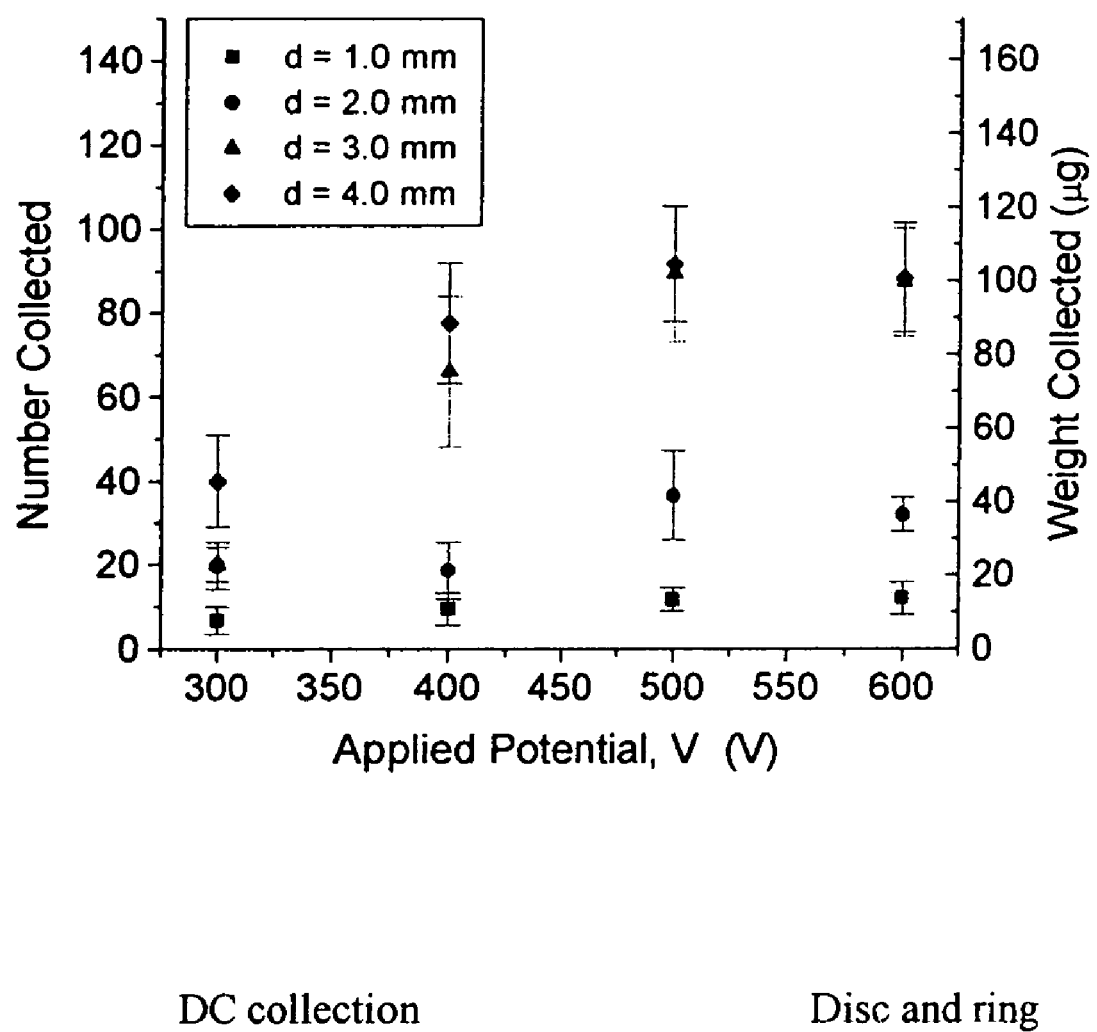
FIG. 10A is a graphical representation of the relationship between amount of material collected and voltage V, for a separation H=0.3 mm, for a disc and ring electrode such as shown in FIG. 9A, with the diameter, d, of disc 4131 varying from 1.0 to 4.0 mm.
Figure 10B:
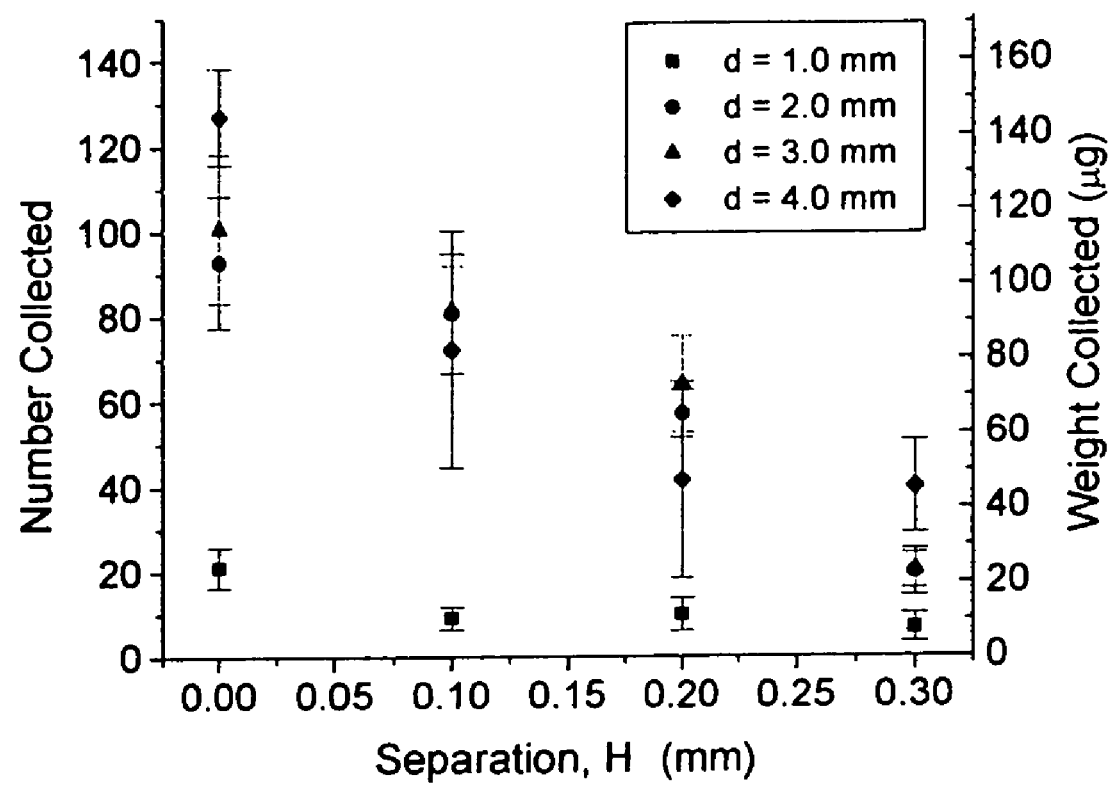
FIG. 10B is a graphical representation of the relationship between amount of material collected and separation H when the voltage is applied, for a fixed voltage of +300V, for a disc and ring electrode such as shown in FIG. 9A, with the diameter, d, of disc 4131 varying from 1.0 to 4.0 mm.

FIG. 10A shows the amount of material collected as a function of applied (positive DC) voltage using the configuration described above in connection with FIG. 9A. The diameter, d, of the disc 4131 was varied from 1.0 to 4.0 mm, and the amount collected is indicated by squares for d=1.0 mm, circles for d=2.0 mm, triangles for d=3.0 mm, and diamonds for d=4.0 mm. The conditions used were $H_R=1.0$ mm, H=0.3 mm. This shows that the amount collected increases slightly as the magnitude of applied voltage is increased. FIG. 10B shows the amount of material collected as a function of the initial separation, H, at a constant applied voltage of +300 V and $H_R=1.0$ mm. The amount collected decreases as the separation, H, increases. Both FIGS. 10A and 10B indicate that the amount collected at a given initial separation and applied voltage increases as the diameter of the disc, d, is increased. FIGS. 10A and 10B further indicate that the applied voltage, V, may be varied to adjust the amount collected within a narrow range, but that the initial separation, H, and the disc diameter d have a much more significant effect.

The disc and ring FIG. 9A operate in a similar fashion. One electrode element is the inner disc 4131, and the other is the outer ring 4132. The facing surfaces are those portions of the outer edge of the inner disc and the inner edge of the outer ring. The less these appear to be flat plates, the less uniform is the field generated there-between. This is why, it is believed, the largest amount of particles are drawn to the sharp edges of these elements, rather than their flat faces.

Elongated Electrode with Disc and Plate Particle Support

Figure 11:
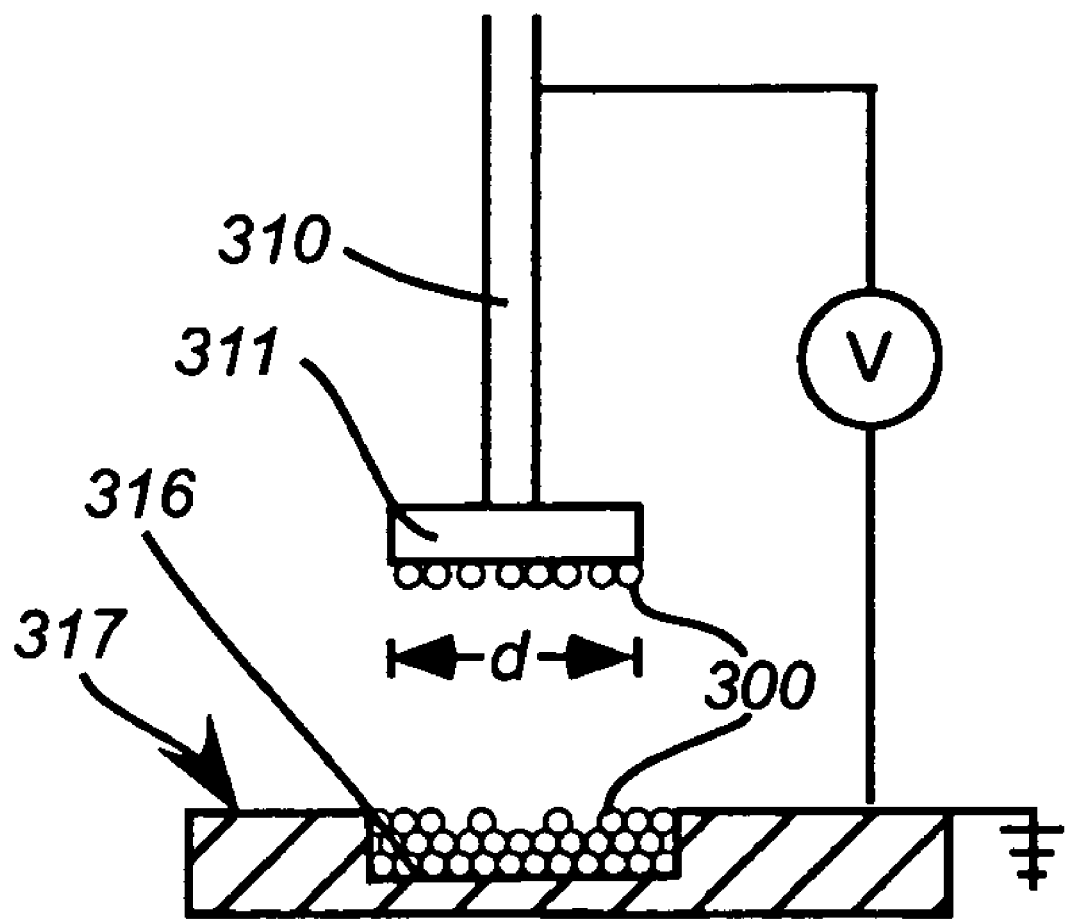
FIG. 11 shows, schematically, an apparatus for collecting particles, using a bare manipulating electrode.

FIG. 11 shows an uncoated manipulating electrode 310 that consists of an elongated rod, with a disc 311 of diameter d. in proximity to a quantity of particles 300, residing in a recess 316 of an extended grounded metal plate 317. This is essentially the configuration shown in FIG. 5D, discussed above in the section regarding the scale of the dielectrophoretic force, and the collection volume. A voltage is applied between the manipulating electrode and the metal plate 317. When the particles 400 contact the collecting electrode 310, while the voltage is maintained on the collecting electrode, the particles are retained there, even as the manipulating electrode 310 is drawn away from the particle support 317.

The amount of material collected by the electrode depends on the initial separation, H, the applied voltage, V, and the diameter of the disc, d.

Figure 12A:
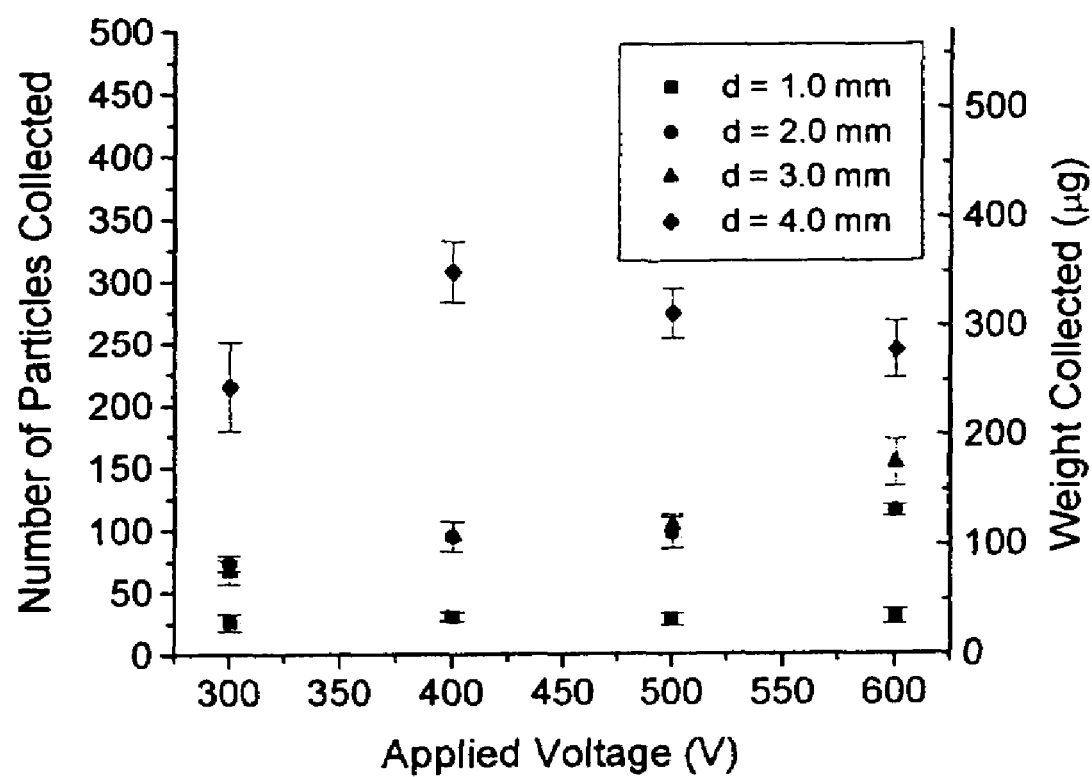
FIG. 12A is a graphical representation of the relationship between amount of material collected and voltage V, for a separation H=0.3 mm, for a disc and plate electrode such as shown in FIG. 11, with the diameter, d, of disc 4131 varying from 1.0 to 4.0 mm.
Figure 12B:
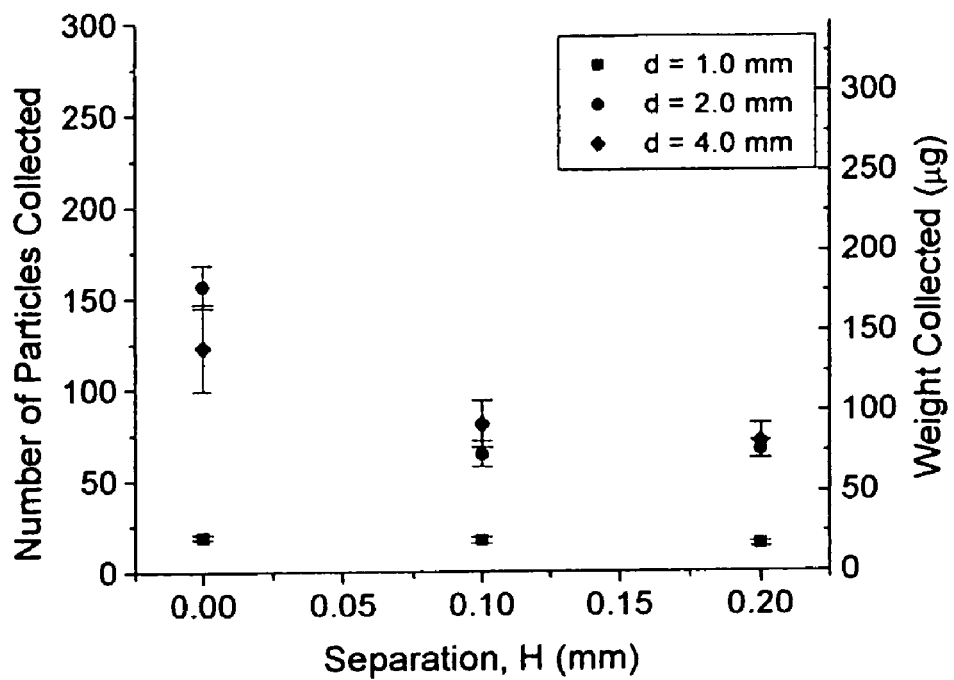
FIG. 12B is a graphical representation of the relationship between amount of material collected and separation H when the voltage is applied, for a fixed voltage of +300 V, for a disc and plate electrode such as shown in FIG. 11, with the diameter, d, of disc 4131 varying from 1.0 to 4.0 mm.

FIG. 12A shows the amount of material collected as a function of applied (positive DC) voltage at constant initial separation H=0.3 mm using the configuration described above in connection with FIG. 11. The diameter, d, of the disc was varied from 1.0 to 4.0 mm, and the amount collected is indicated by squares for d=1.0 mm, circles for d=2.0 mm, triangles for d=3.0 mm, and diamonds for d=4.0 mm. This shows that the amount collected increases slightly as the magnitude of applied voltage is increased. FIG. 12B shows the amount of material collected as a function of the initial separation, H, at a constant applied voltage of +300 V. In general, the amount collected decreases as the separation, H, increases. Both FIGS. 12A and 12B indicate that the amount collected at a given initial separation and applied voltage increases as the diameter of the disc, d, is increased. FIGS. 12A and 12B further indicate that the applied voltage, V, and the initial separation H, may be varied to adjust the amount collected within a narrow range, but that the disc diameter d has a much more significant effect for this configuration.

Non-elongated Electrodes that Generate Spatially Non-uniform Field

The foregoing discussion has illustrated using an electrode that generates a non-uniform field to give rise to a dielectrophoretic force on an item composed of a dielectric material. Most of the manipulating electrodes discussed are also elongated in some sense. A simple, single element electrode, as shown in FIG. 5A is elongated along the dimension from the electrode support to its terminus. The particle support electrode is spatially extended in the two dimensions that are perpendicular to the dimension of elongation. This electrode pair gives rise to a spatially non-uniform field, and non-zero gradient, as discussed above.

The parallel pin electrodes are elongated in the dimension from the electrode support, to the terminus of the pins, as are the parallel loops. The loops are also elongated in the dimension that is perpendicular to the first mentioned, parallel to the surface of the particles. Both the parallel pins and the parallel loops give rise to a spatially non-uniform field, but they do so by generating a field that extends between the two elongated elements (e.g., the two parallel pins), rather than between an elongated element and a counter electrode that is spatially extended in two dimensions that are perpendicular to the dimension of elongation, such as a plate.

A common characteristic in both cases, and, without being limited to a particular theory, one which it is believed gives rise to a non-uniform field, is that in both cases, the field is generated between facing surfaces of the two elements that make up the electrode pair. In general, the elements do not have facing flat surfaces, where both dimensions of both facing surfaces are large as compared to the distance between them. Formulated alternatively, for any facing surfaces, the distance between the two facing surfaces of the electrode elements is large compared to the extent of either facing surface, in any one dimension. By "facing, it is meant surfaces that have parallel tangent planes, and portions of the surfaces adjacent thereto. By large, it is meant at least approximately twice as great, preferably at least four times as great, and most preferably, in some cases, at least eight times as great. If the distance between the two spatial extents is small, compared to both of these spatial extents, then the facing surfaces act together as a pair of parallel, or nearly parallel plates, and the field is uniform, or close to uniform.

For instance, in the case of the elongated electrode 110 shown in FIG. 5A and the counter electrode 114 that is spatially extended in at least one dimension perpendicular to the dimension of elongation of the electrode 110, the extent of facing surface (either a semi-circle, or, if there is rotational symmetry around the long axis, a hemi-sphere) of the tip of the elongated electrode 110 is small compared to the distance between that tip and the counter electrode 114. This gives rise to a spatially non-uniform field, as shown in FIG. 5A, and a dielectrophoretic force.

In the case of parallel pins, as shown in 5110a and 5110b, as shown schematically in FIG. 1F, the non-uniform field arises between the two elongated elements 5110a and 5110b themselves. Each constitutes the counter-electrode for the other. The facing surfaces are thin rectangles, almost lines, on each element 5110a and 5110b, facing the other. These have a small extent in the dimension circumferentially around the electrode, as compared to the distance between the two elements.

The parallel loops FIG. 7A, operate in a similar fashion to the parallel pins, but with a longer extent of conducting element, which is simultaneously near to the items to be collected, and facing its counterpart on the counter electrode.

The disc and ring operate in a similar fashion with one conducting element being the inner disc 4131, the other being the outer ring 4132.

Thus, in the cases of the parallel pins, loops and the disc and ring, the elongated shape, protruding from their electrode support, is not necessarily the dominant factor in giving rise to a non-uniform field. The geometrical considerations comparing the dimensions of facing surfaces to their separation mentioned above also contribute.

Figure 22:
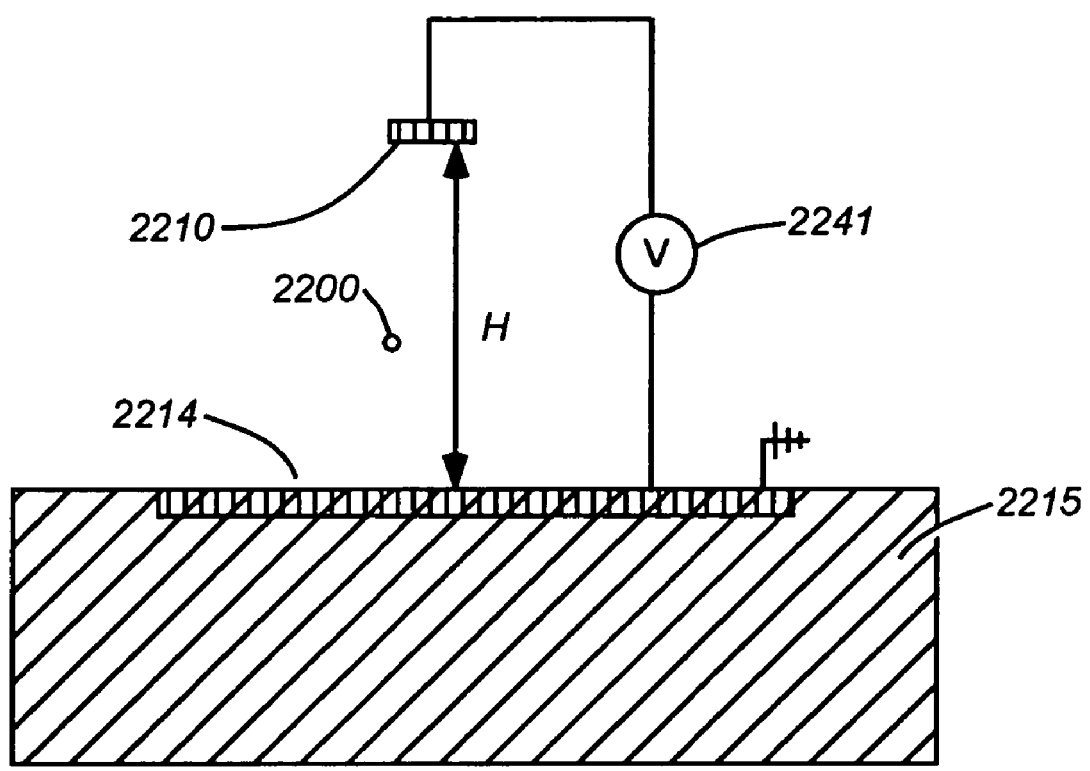
FIG. 22 shows schematically, an electrode that will produce a non-uniform field, which electrode is not elongated.

The elongated shape is useful for accessing recesses, but it is not necessary to generate the non-uniform field. For instance, as shown in FIG. 22, a planar, non-elongated, collecting electrode 2210 is provided opposite a counter electrode 2214 that is spatially extended in at least one dimension relative to the collecting electrode 2210, and is spaced away therefrom a distance H that is large compared to at least one dimension of the collecting electrode 2210. If the collecting electrode 2210 is maintained at a voltage by voltage source 2241 compared to the larger, counter electrode 2214, a non-uniform field will arise therebetween, due to the geometry of the plates and their spacing, and will present a dielectrophoretic force upon a dielectric particle 2200 that resides between the two, forcing that particle toward the smaller collecting electrode 2210. Thus, a dielectrophoretic force arises between two electrodes, neither of which are elongated. Thus, in general, particles are attracted to the electrode that has the smaller extent, in at least one dimension.

Microchip Electrode with Support

Figure 13:
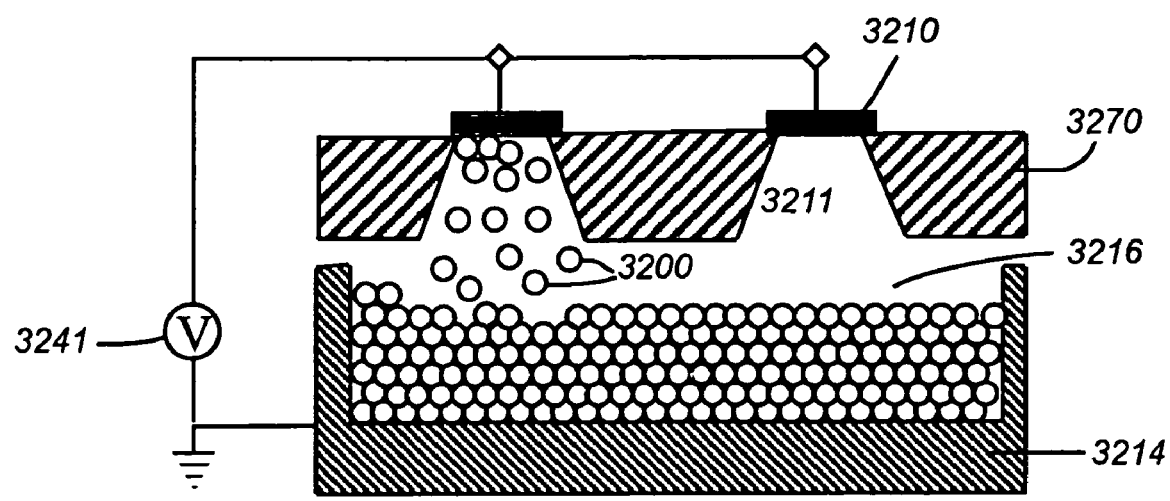
FIG. 13 shows, schematically an apparatus for collecting particles into an inverted recess of a microchip.

A method for filling the wells of a pharmaceutical material delivery microchip (discussed above) (either implantable or not) with a dry powder, such as an active drug or powdered protein exploits such electrodes that need not be elongated to generate a spatially non-uniform field. The method and apparatus are shown schematically in FIG. 13. A conductive membrane 3210 covering each well 3211 of a microchip 3270 acts as a manipulating electrode to collect the drug particles 3200. Prior to collection, the particles 3200 reside in a recess 3216 of a grounded metal support 3214. Application of a voltage between an individual conductive membrane 3210 and the grounded metal support 3214 generates a spatially non-uniform electric field, whose field lines converge on the membrane. This field acts to draw the particles 3200 upward toward the membrane 3210, thus filling the well 3211. The voltage applied may be either AC or DC. The filled well may then be sealed by methods described in (Santini, U.S. Pat. No. 5,797,898, cited above) prior to removing the voltage to ensure that the particles are retained in the wells. Thus, the conductive membrane 3210 in the recess 3216 acts as a manipulating electrode, to simultaneously collect particles and deposit them where they are to be used. This is a particularly useful embodiment, as it combines collecting and depositing steps (discussed in general below) into one, thereby resulting in a very efficient process.

The recesses of the microchip can be filled either one at a time, or more than one at a time. The microchip includes circuitry that allows addressably providing a voltage to each of the conductive membranes for subsequent release of the materials that are contained in the recesses. This same circuitry can be used to addressably provide a voltage to the membrane to generate a non-uniform field, as discussed above. Thus, all of the recesses can be filled simultaneously, if the microchip is placed adjacent a large expanse of material to be collected and all of the membranes are provided with a voltage. Alternatively, an individual membrane of a recess can be provided with a voltage, to fill that recess. Or, a plurality of membranes, either adjacent or spaced apart, can be simultaneously energized to fill a selected plurality of recesses.

Aerosol Configurations

Similar methods and apparatus can be used for collecting dielectric items that are suspended in a gas, such as an aerosol cloud, or a volume of air.

Figure 14:
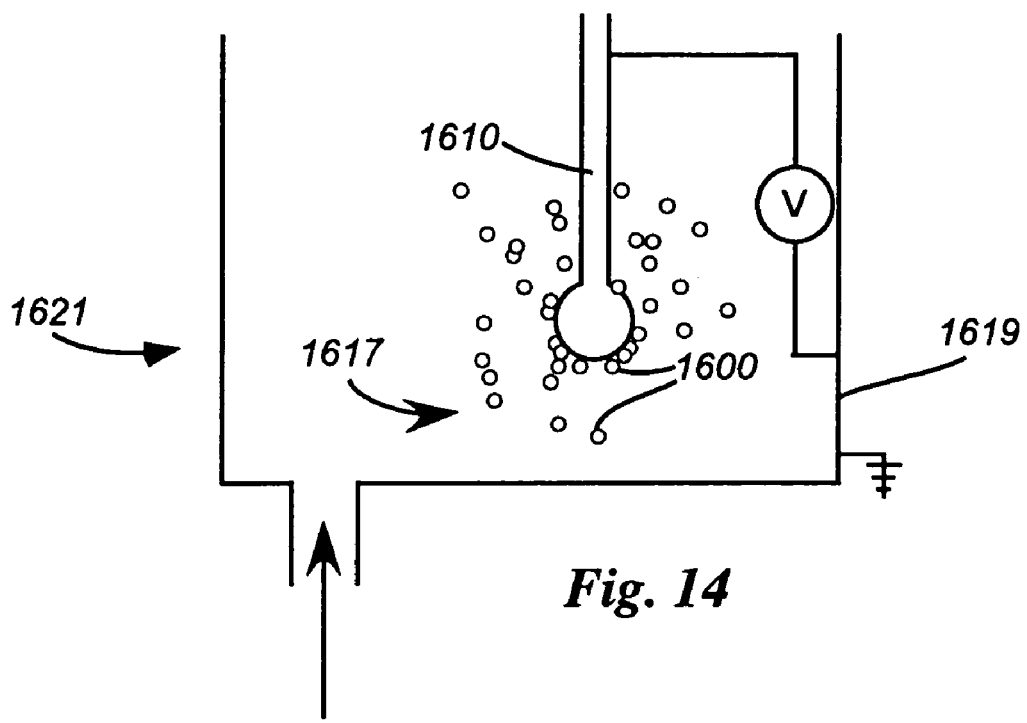
FIG. 14 shows schematically a set up for collecting particles from an aerosol cloud with a single element manipulating electrode.
Figure 16A:
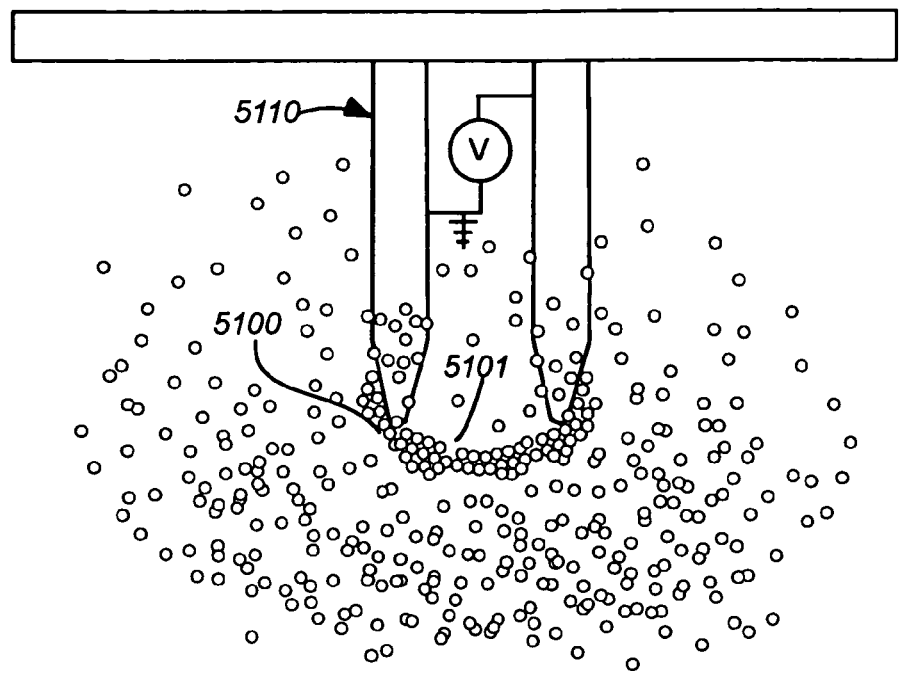
FIG. 16A shows schematically, a set up for collecting particles from an aerosol cloud, with a two pin manipulating electrode.
Figure 16B:
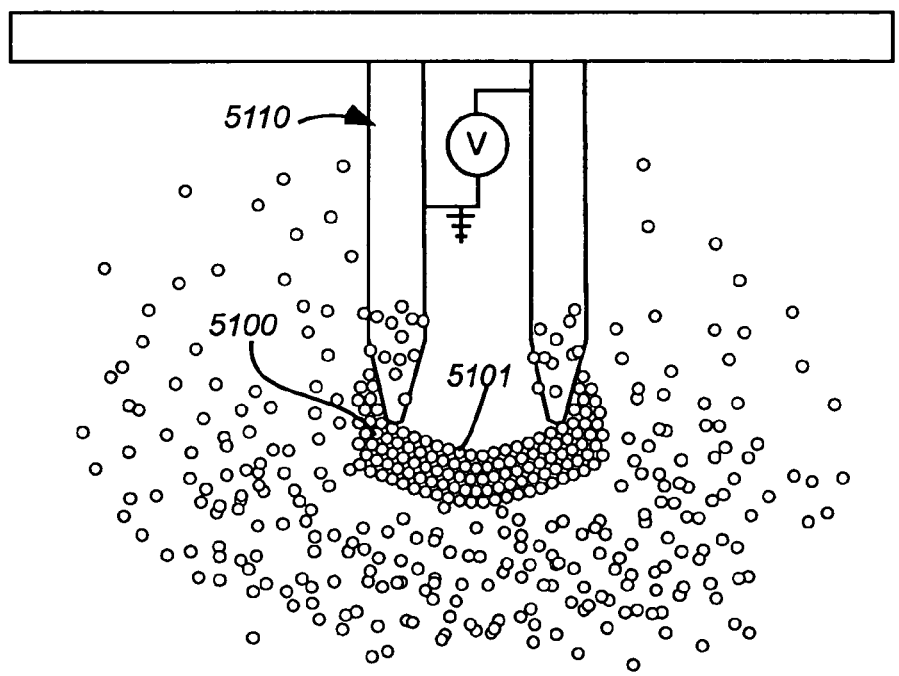
FIG. 16B shows schematically the two pin manipulating electrode shown in FIG. 16A after having collected particles from an aerosol cloud.

For instance, FIG. 14 shows using an elongated electrode to collect small particles from an aerosol cloud. The walls 1619 of the aerosol chamber 1621 are grounded, and a voltage is applied to the elongated electrode 1610 to create a spatially non-uniform field, generally having field lines that converge on the elongated electrode 1610. This will cause particles within the critical volume to be drawn to and retained by the manipulating electrode, as shown in FIG. 14. With the aerosol embodiment, advantage can be taken of the fact that the manipulating electrode is essentially immersed in the items to be collected. Thus, they may be drawn toward it from all directions, if the shape of the field and the gradient of its square so dictate. Either AC or DC excitation can be used to generate the field. Alternatively, a parallel pins electrode 5110, such as has been described above can be used. FIG. 16A shows using a parallel pin type electrode 5110 to collect particles 5100 from an aerosol dispersion, with FIG. 16B showing the particles forming strings 5101, similar to what arise in the non-aerosol case.

Figure 15:
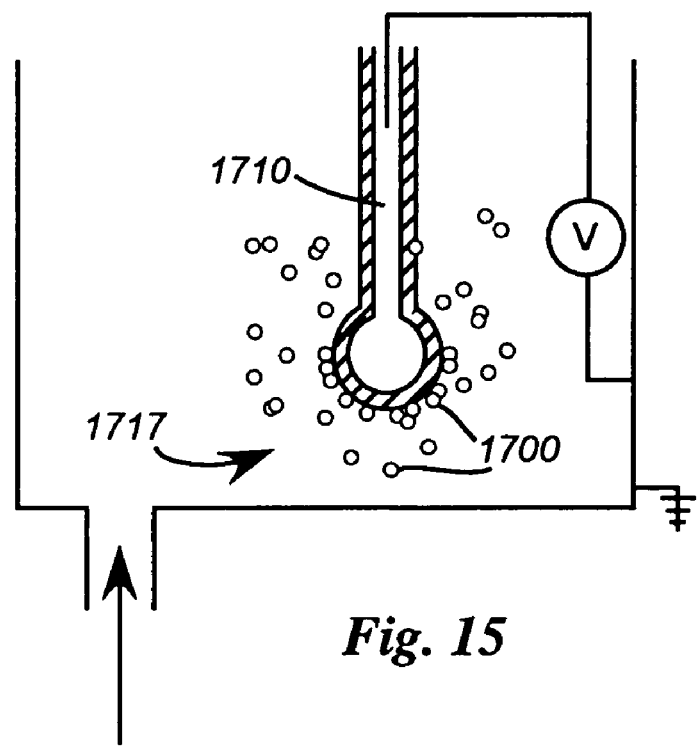
FIG. 15 shows schematically a set up for collecting particles from an aerosol cloud with a single element manipulating electrode that has a dielectric cover.

The electrode used for aerosol collection can be covered with a dielectric covering, such as shown in FIG. 15 for a single element electrode 1710 or FIG. 3A for a two pin electrode,.

Figure 17:
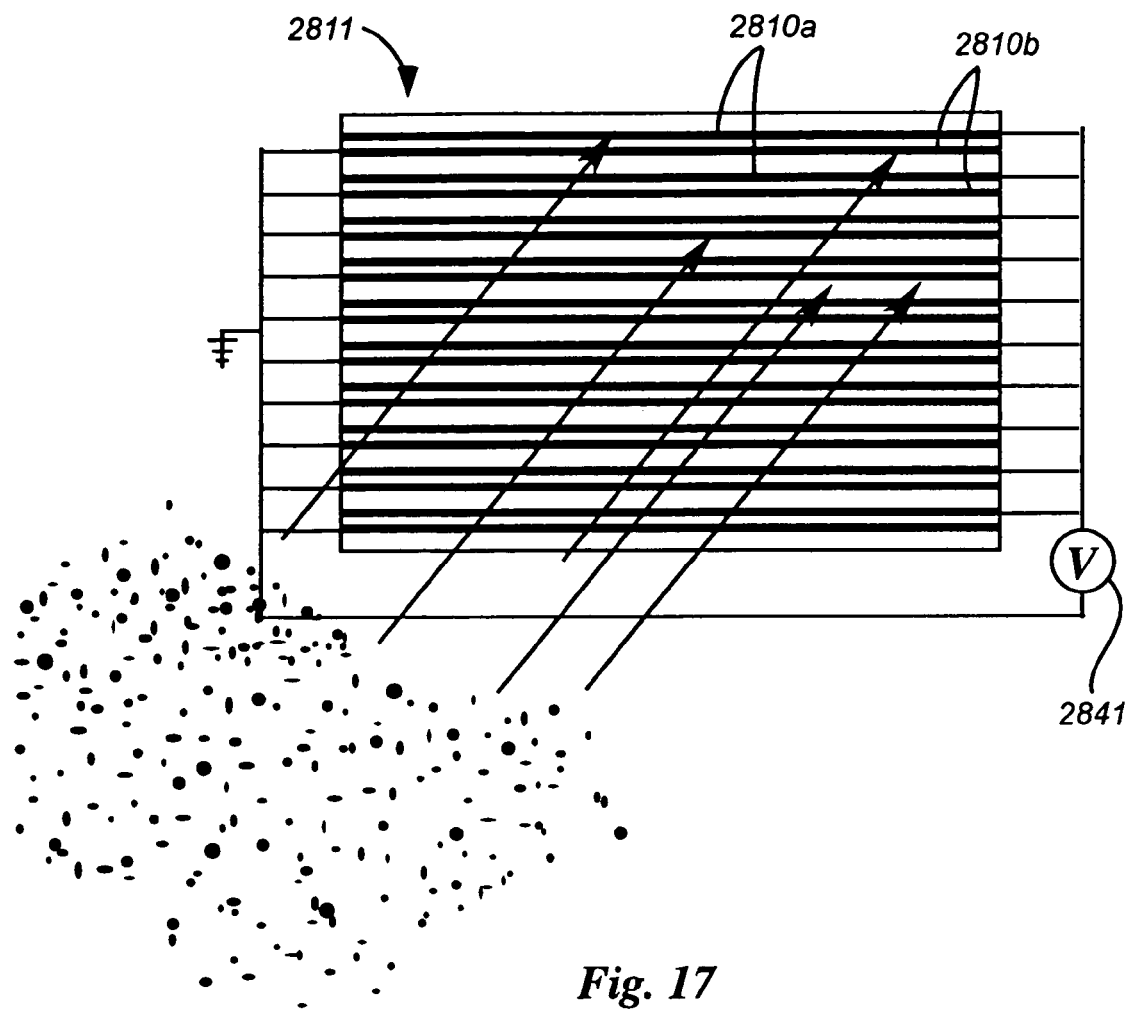
FIG. 17 shows schematically a set up that exploits dielectrophoretic force to remove particles from a relatively large volume of air, having a plurality of parallel wire manipulating electrodes.

This technique can also be used as a dielectrophoretic cleaner for removal of particles from an air stream. For instance, an array 2811 of elongated wire electrodes 2810a and 2810b is arranged, as shown in FIG. 17 connected to a voltage source to create a spatially non-uniform field that will draw items to each wire. The gas is passed through the array of electrodes until a quantity of particulates is accumulated on the electrodes. This quantity is then removed from the electrodes, such as by washing, or other suitable means, thereby effectively removing the particulates from the gas. The wire electrodes are arranged in pairs, with one 2810a being connected to a voltage source, and the other 2910b to ground. Typically, the pair members are adjacent each other. Thus, each pair acts in the same manner as the pair of loops 6110a and 6110b, shown in FIG. 7A. Typically, for air cleaning, the wires would have length l on the order of 10-100 cm. The wires can be covered with a dielectric covering, which may, in some instances, facilitate subsequent cleaning.

FIG. 17 shows linear manipulating electrodes 2810a and 2810b. However, this is not required. Concentric circular electrodes, or any other shapes that provides the necessary field and gradient can be used, depending on the geometry of the equipment and ducting in which the cleaner is to be used.

The techniques and apparatus discussed above can be used with a wide variety of dielectric materials, including, but not limited to: active pharmaceutical ingredients (e.g., aspirin), excipients, proteins, salts, ceramic powders (e.g., silica), pigments, catalysts, polymer particles, adhesives and phosphers.

Charge Disposition of Collected Items After Collection

Figure 18:
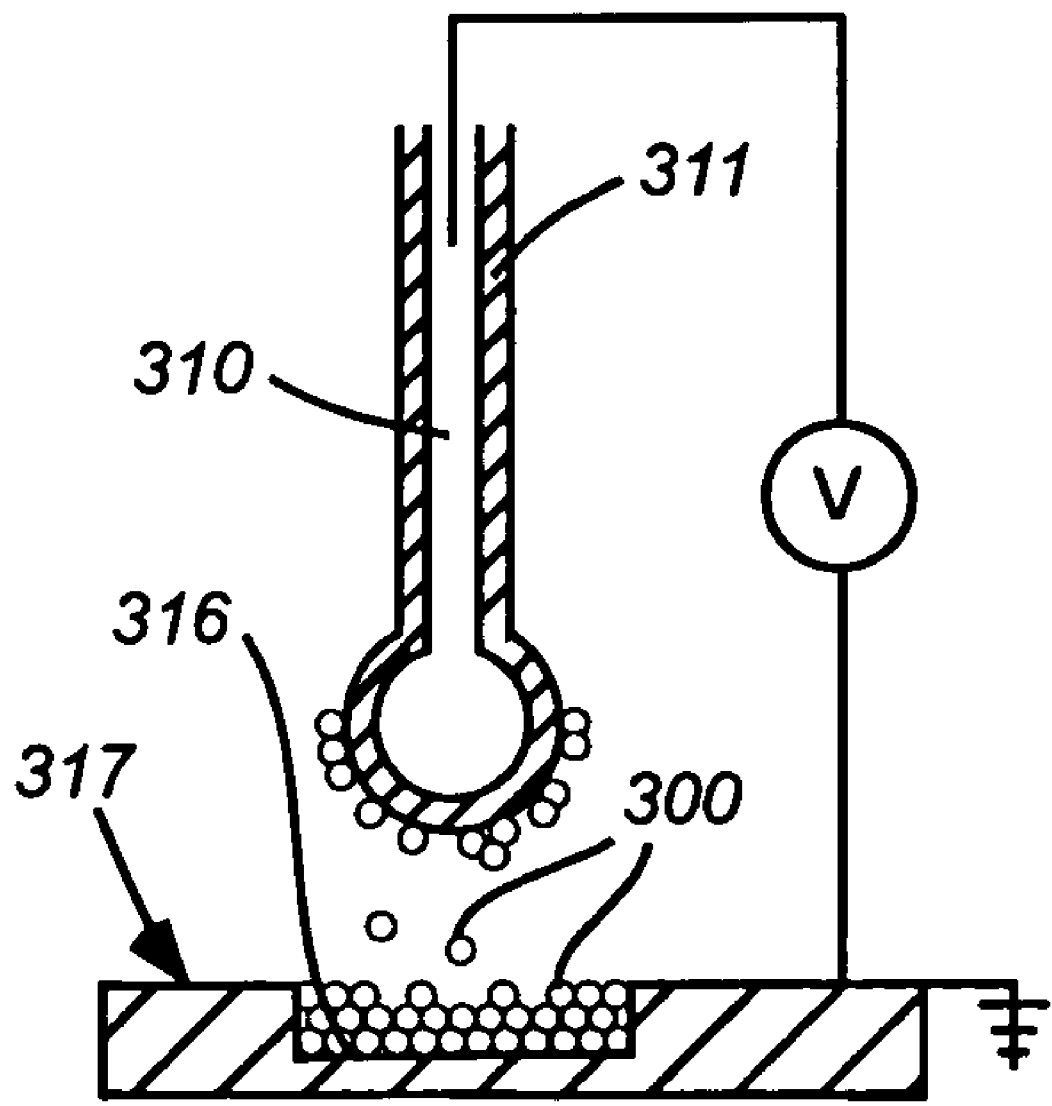
FIG. 18 shows schematically, an apparatus for collecting particles with a collecting electrode that is covered with a dielectric cover.

As mentioned above, it is not necessary that the manipulated items carry a charge before they are manipulated. Particles that have acquired a surface charge, for example by triboelectrification, may be manipulated by this method. Collection of particles on a single electrode is discussed above with reference to FIG. 11. In general, the forces exerted on the particles by the spatial non-uniformity of the applied field may attract them to the electrode 310, regardless of their surface charge or the polarity of the field. A bare metal electrode, as shown in FIG. 11, may cause charged particles to discharge. The extent to which this occurs will depend on many factors: the surface conductivity of the particles, the initial charge, the voltage, and the duration of contact with the manipulating electrode. A collecting electrode 310, which is covered with a dielectric (as shown in FIG. 18), will allow the particles 300 to maintain their initial charge state after collection. It is not, therefore, possible to predict, in general, the exact surface charge of the particles at various points throughout the manipulation process. What is known is that a dielectrophoretic force will arise regardless of the surface charge that the particles carry. Further, it will typically dominate any charge related forces between the particle and the collecting electrode, either attractive or repelling for the usual magnitudes of voltage applied during collection. Thus, it is possible to attract and retain particles regardless of their charge.

Charged Item Manipulation

Items to be manipulated that are charged, for example by triboelectrification, are drawn toward the collecting electrode by dielectrophoretic force, and are retained there in the same manner as if uncharged. However, there is a Coulombic force that also contributes to the attraction (or opposes the attraction, if the charge polarity is the same as the polarity of the collecting electrode). However, it is believed that the charge related contribution is dominated by the dielectrophoretic contribution to the force, and that its effect can be countered and accounted for by calibration, as explained below. Rough calculations performed to establish the general scale of the dielectrophoretic force, compared to the charge based force that would arise, assuming the maximum charge that a representative particle could hold, given the breakdown voltage of the surrounding air, show that the dielectrophoretic force will dominate significantly. Experiments have also shown that negatively charged particles may be collected with an applied voltage of either positive or negative polarity.

The surface charge of a dielectric item may be altered by direct electrical contact with a bare electrode. Without being limited to a particular theory, it is believed that given enough contact time between the item and the electrode, the item may discharge. On the other hand, if the manipulating, collecting electrode is provided with a dielectric covering, such as is shown in FIG. 18 then, when the particle contacts the electrode, it will not change its surface charge. Thus, providing the dielectric covering provides more certainty as to the factors that contribute to the surface charge of the particles. Basically, they will retain near to the charge that they had before collection. Thus, after collection, its charge might be exploited for deposition on a target. The electrode containing the particles may be brought into close proximity of a charged target region, or an electrode with an appropriate applied voltage, which could pull the charged item from the manipulating electrode, by virtue of coulombic force.

Manipulation of Microelectronic Parts—Collection

An invention disclosed herein can be used to attract microelectronic parts to an electrode for subsequent manipulation. As discussed above, the microelectronic parts need not carry a surface charge, as they are attracted to the electrode by the non-uniform field. An apparatus appropriate for manipulating a shaped microelectronic component is shown schematically in FIG. 19A. A spatially non-uniform field is generated by applying a voltage between the elongated electrode 1510 and a grounded metal plate 1515, below a dielectric layer 1514, upon which one or more parts 1500 rest. The shape of a surface 1519 of the part 1500 can be exploited by providing an elongated electrode 1510 with a corresponding shape on its contact surface 1521. The shapes of the two surfaces are complementary to help the part be retained on the electrode, and to aid in alignment. As shown, in this case, they are both stepped, with mating flats, but this need not be the case. For instance, one could be a concavity, and the other a matching convexity.

The charge retention behavior of a microelectronic component being deposited is essentially similar to that discussed above in connection with transporting particles.

Figure 20:
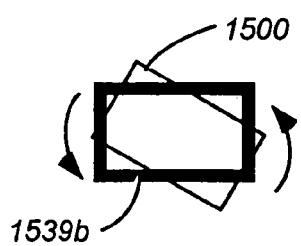
FIG. 20 shows schematically an enlargement of a plan view of a misaligned microelectronic part being attracted to a manipulating electrode.

The shape of the collecting electrode may be designed to create an electric field that will exert a torsional force on a misaligned part. This may aid in establishing proper alignment of the microelectronic part by rotating it about an axis that is perpendicular to the surface of the collecting electrode. For instance, as shown in FIG. 20, which is a schematic bottom view, if the shape of the component 1500 is rectangular, with a longer and a shorter side, when the field generated by an appropriately shaped collecting electrode, will cause the part to rotate.

Figure 19A:
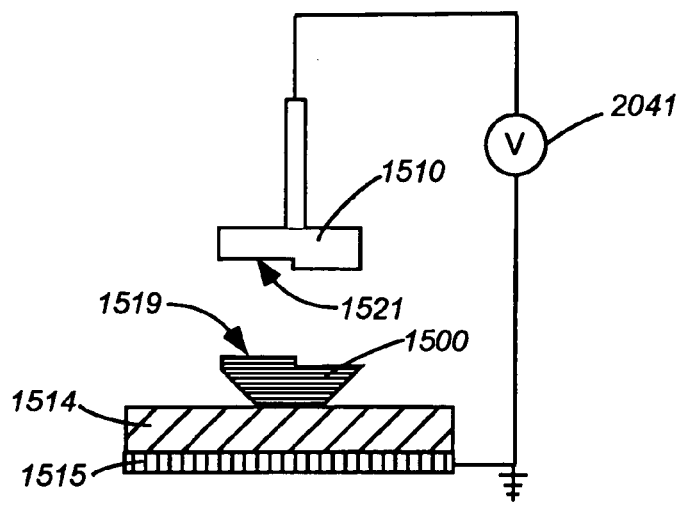
FIG. 19A shows schematically a bare shaped electrode used to attract a microelectronic component for subsequent manipulation and placement onto a recipient substrate.
Figure 19B:
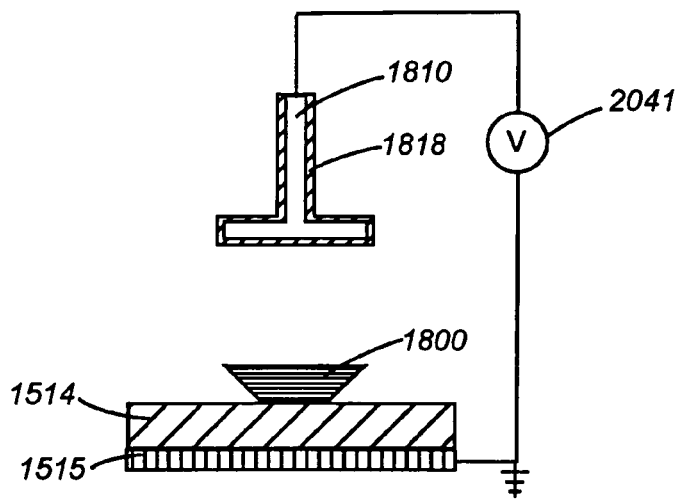
FIG. 19B shows schematically a shaped electrode coated with a dielectric layer, used to attract a microelectronic component for subsequent manipulation and placement onto a recipient substrate.

FIG. 19B shows an arrangement similar to that shown in FIG. 19A. However, in FIG. 19B, an elongated electrode 1810 is used that bears a dielectric coating layer 1818. The dielectric layer 1818 prevents the component 1800 from discharging any charge that it may carry. It also prevents any charge from conducting from the elongated electrode 1810 and accumulating on the component during collection. This insulation feature may be helpful with some microelectronic components, which may be damaged if charged, or discharged, in particular, too quickly. It also helps to minimize the uncertainty associated with any possible charge that might be carried by the item to be manipulated. The operation of this embodiment is otherwise identical to that described above in connection with FIG. 19A.

Elongated Shape Permits Manipulation into Recesses

Figure 24:
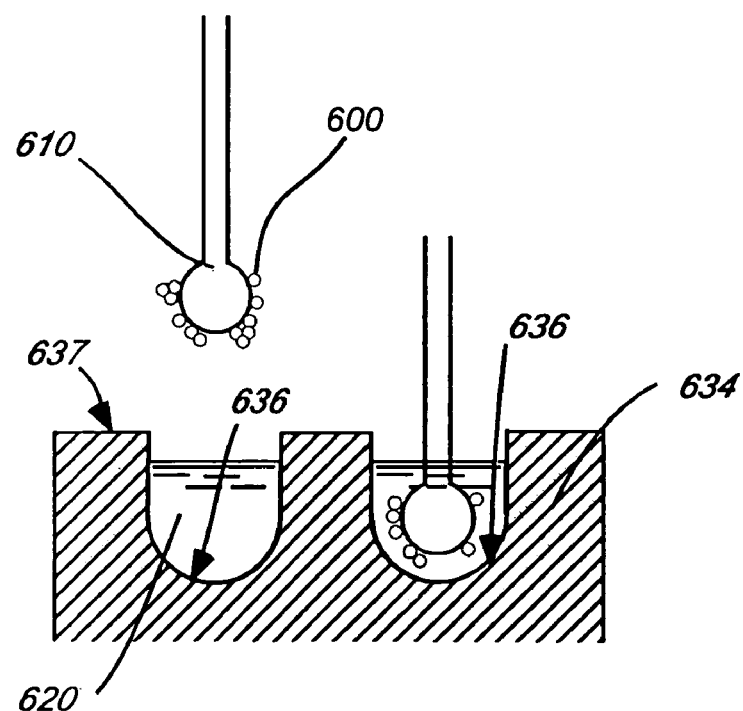
FIG. 24 shows schematically using an elongated electrode to deposit an item within a well that contains a liquid.

The shape of most of the electrodes discussed above has been generally characterized as elongated, or protruding from a support, and the effect of such an elongated shape, giving rise to the dielectrophoretic force has been discussed. An elongated shape provides other opportunities by virtue of its elongated, and otherwise shaped geometry. For instance as shown in FIG. 24, a generally elongated electrode 610 can be used to handle (collect, transport and deposit) items 600 into concave shaped recesses 636 of a body 634, such as a well in a microtitre plate. This might not be possible with a flat manipulating electrode, or, it might be more difficult.

There are many instances in which manipulation of small items to and from such recesses are required: for instance, small beads are used to carry reagents for combinatorial chemistry. It is necessary to be able to manipulate a single bead, or a small number of beads, either alone, or carrying a controlled amount of reagent or test material. In the latter case, the reagent, or other test material, is carried by subsequent handling of the bead. One aspect of an invention disclosed herein can be also be used to dispense the reagent. For instance, a dry, non-conductive, powdered reagent, can be collected and then deposited into the wells of a microtitre plate. An invention described herein can be used to handle both the beads, and the powdered reagent.

Any of the electrode shapes discussed above can be used to collect items from, (or deposit them, as described below) into a receptacle, such as a well of a microtitre plate. Just as examples, the simple, unitary elongated electrode shown in FIG. 5C, the parallel pins, (or "points") electrode shown in FIG. 1B, and the parallel loops electrode 6110 shown in FIG. 7A and the disc and ring electrode 4130 shown in FIG. 9A (discussed above) may all be so used. In the case of the parallel pin 5110 and loops 6110, their spacing w must be small enough to fit within the well. Similarly, the loops length l must be short enough to fit within the diameter of the well 3116. A typical well is between two and ten mm in diameter with those widely in use being about five mm in diameter and about one cm deep. However, there are a wide variety of well sizes and shapes, and virtually any configuration is possible.

Figure 21A:
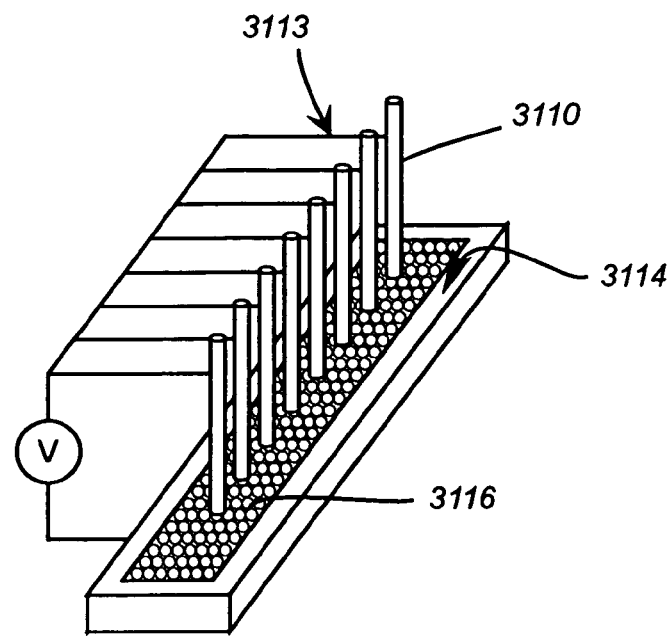
FIG. 21A shows schematically, in perspective view, an array of electrodes manipulating items with respect to multiple wells of a microtitre tray.

In this context, by "elongated" it is meant an electrode as shown in FIG. 1A, that extends, or protrudes somewhat from an electrode support 5070, so that the portion of the free end of the electrode, upon which the particles being manipulated are adhered, can be inserted deep enough into a receptacle to be deposited therein. Or, if the electrode is being used to collect from within a receptacle, the electrode must be able to be inserted deeply enough into the receptacle to retrieve the item. Thus, the electrode can also take the form of a slender stalk, terminated by a shaped end, such as a ball, or a disk, a plurality of such stalks, a rod, a hollow tube, of any cross-section, etc. Typically, an elongated electrode will be longer than it is wide, although, this need not be the case. It does need to protrude somewhat beyond its support. FIG. 21A is meant to show, generically, with electrode 3110 any of the above-mentioned, or any suitable elongated electrode, in an array.

Array of Electrodes and Calibration

Figure 21B:
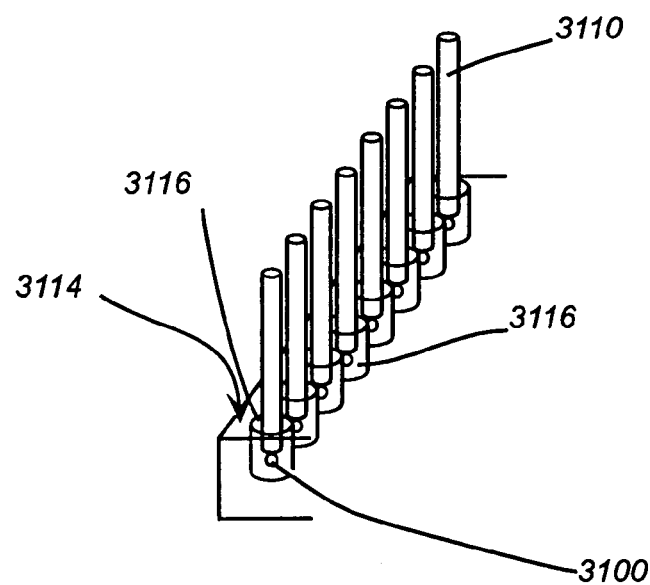
FIG. 21B shows schematically an enlargement of a portion of the array of manipulating electrodes shown in FIG. 2A.

As shown in FIGS. 21A and 21B, an array 3113 of elongated electrodes 3110 can be used in an automated system with a target microtitre plate 3114. The array can be of any size. It can be a single row or column of electrodes, either extending across the full extent of the microtitre plate, or only a portion thereof. Or, it could be a two dimensional array of rows and columns, of whatever size is convenient, from 2×2 to the full size of the plate (26×6, as shown). When an array 3113 of electrodes 3110 is used, a selected portion of the array, for instance a row of six, can be used for calibrating the collection and deposition properties of the equipment. Typically, within each calibration well, the amount of material that is actually deposited is measured. From this measurement, the rest of the plate can be calibrated by routine statistical techniques. For instance, the amount of material collected and deposited by each of the electrodes of the calibration portion of the array (either the number of countable particles, such as beads, or the volume, or weight, or concentration in liquid of less easily countable powder material) can be measured, and averaged, or otherwise statistically analyzed, over the range of calibration, thereby obtaining an accuracy factor for the remaining wells. Thus, each microtitre plate can be separately calibrated.

Another type of target that has a plurality of recesses is an implantable microchip, such as discussed above. The recesses of a microchip can be filled by an array of manipulating electrodes.

In cases where the target does not have a plurality of separate target regions, such as a microtitre tray, calibration can still be accomplished. There are discrete deposits of items, typically in discrete events and at discrete locations on a target. The amount of material that is collected and discretely deposited for the first several collection events, (or selected subsequent collection events) is measured. Then conditions are maintained stable for the remainder of runs. Thus, rather than designating several essentially simultaneously deposited quantities for calibration, as with a microtitre tray, several discrete, sequentially deposited quantities are used. They can be selected from close in time, or spaced-in-time discrete deposits.

Shapes of Items to be Manipulated

Figure 41:
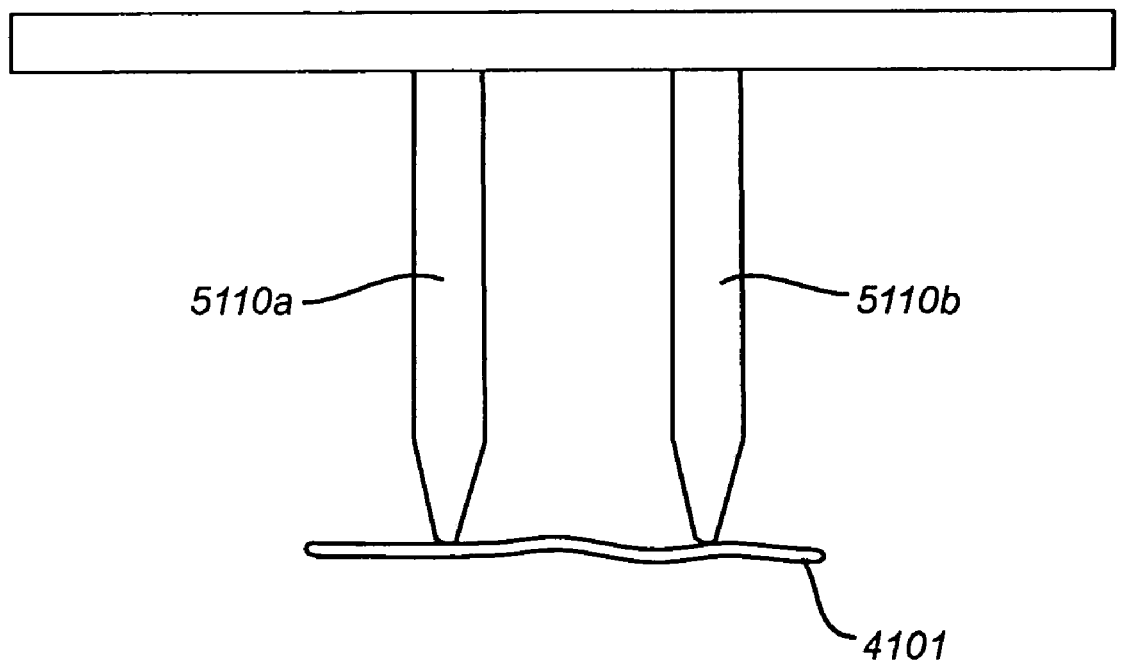
FIG. 41 shows, schematically, a parallel pin manipulating electrode, to which a threadlike micron scale item has been attracted and collected.
Figure 42:
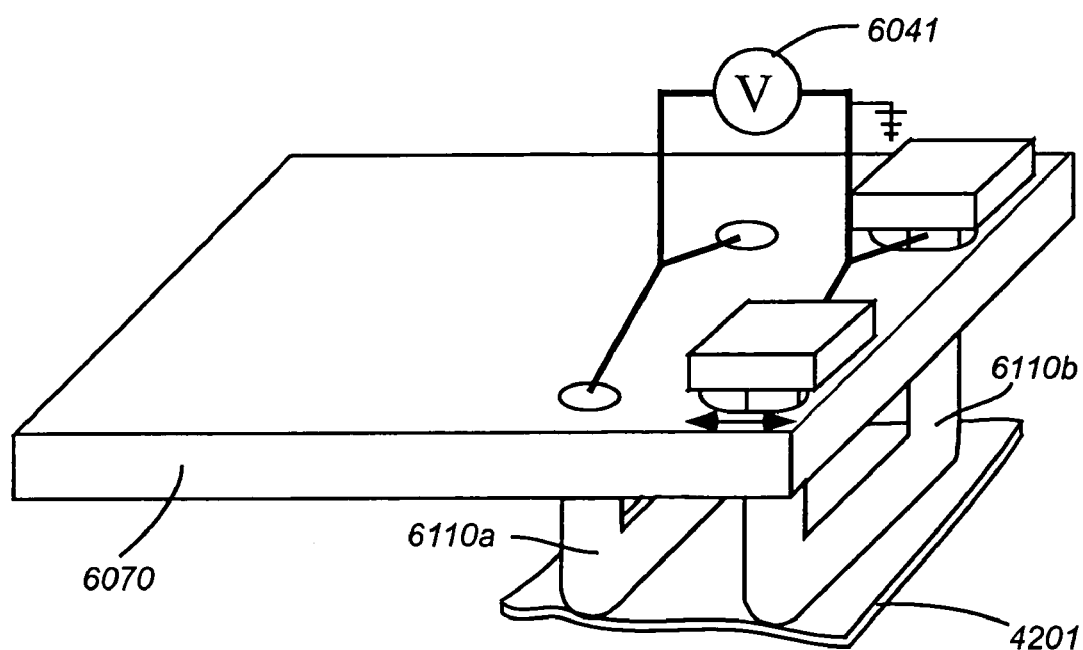
FIG. 42 shows, schematically, a parallel loop manipulating electrode, to which a sheetlike micron scale item has been attracted and collected.

The discussion above has used as an example roughly spherical micron scale items (from one to several hundred microns) to be manipulated, as well as microelectronic parts that are roughly the same size in all three dimensions. The inventions disclosed herein can be used to manipulate items that are micron scale in only two (threads) or one (sheets) dimensions, while being significantly larger in a third, or second and third dimensions. For instance, threads, whiskers, crystals, etc., that are micron scale in diameter, and much larger in length, can be collected, for instance to a two element manipulating electrode, such as the parallel pins electrode of FIG. 1A, or the parallel loops electrode of FIG. 7A. In such a case, as shown in FIG. 41, the threads 4101 would be collected analogously to the strings of particles, aligned as are the strings. Similarly, as shown in FIG. 42, sheets 4201 can be collected by the parallel loops electrode, an array of them, or an array of parallel pins. As used herein, "micron scale" includes any such items that have at least one dimension that is micron scale.

Deposition of Dielectric Items

Once these dielectric bodies have been collected onto an elongated manipulating electrode, they are transported, and deposited on a target. FIG. 44 shows, schematically, a collecting module 9001, with a generic manipulating electrode 9110, collecting generic items 9100 from a supply module 9105, to be transported to a generic target module 9130, where each of the collecting module 9001, item supply module 9105 and target 9130 are provided with an x-y-z transport module 9201, 9202, 9203, respectively, to position each relative to the environment, and to the others. Any of the collecting electrodes discussed herein can be so transported, to any of the targets discussed herein. Typically, the collecting electrode is moved away from the particle, or item support. This motion can be vertical, or horizontal, or a combination thereof. To be more precise, relative motion between the collecting electrode and the item support is established. In some cases, the electrode moves (relative) to fixtures, and in some cases, the item support moves relative to fixtures. In some cases, both move, for instance with the collecting electrode moving up and down, and the item support and target (discussed below) moving horizontally, for instance along a circuit, past numerous different processing stages, including a collection and a deposition stage. As used in the claims, it will be understood that motion of any of the modules is equivalent to relative motion among the named modules.

For most combinatorial chemistry applications, the target is the well of a microtitre tray. For microelectronic components, the target is a portion of a chip. For microchip applications, the target is a recess on a pharmaceutical delivery microchip, which may but need not be implantable. Other types of targets are also possible.

In many cases, the manipulating electrode is brought near to and above the target (or the target is brought near to and beneath the electrode) and a voltage is removed from the manipulating electrode, which removes all of the force that has been holding the manipulated items to the electrode. In such a case, the items simply fall under the influence of gravity to the target. If the particle is so small that its velocity toward the target is very small, additional directing force, as described below, can be provided. If the particle falls with an acceptable speed, the gravity can be sufficient. In some, other cases, when the bias is removed from the manipulating electrode, the transported items remain adhered, as has been discussed. In that case, various techniques can be used to remove the items. These include but are not limited to: rinsing with a liquid, application of dielectrophoretic force, or application of coulombic force. In all of these cases, the precise force that is applied is not critical. All that is required is to provide enough force to dislodge the manipulated item from the manipulating electrode. Once dislodged, gravity will bring the item to the target. In some cases, providing a target with a shaped recess (as described below) will help to direct the items to the desired target region, and to keep them there. Various targets, and methods for depositing the collected items into them will be discussed below.

Deposition Exploiting Dielectrophoretic Force

The dependence on shape and size discussed above in connection with dielectrophoretic collection using non-elongated electrodes can also be exploited to remove particles and items from a collecting electrode, and to deposit them on a target. In essence, the target is also a collecting electrode. However, rather than collecting from a particle supply, the collecting is from previously collected particles retained by a manipulator electrode. The geometries and sizes and voltages must be tailored so that particles are preferentially attracted then, to the target, as compared to the manipulating electrode. This is discussed in more detail below, in connection with FIG. 36, for example.

Microtitre Wells

FIG. 24 shows, in an enlarged cross-sectional view, using an elongated electrode 610 to deposit particles 600 into a well 636 of a microtitre plate 634. The electrode 610 is shown as a generic ball-ended stick, but any elongated electrode, including, but not limited to structures, as discussed above, could be so used. The well 636 contains a quantity of liquid 620, which may be selected for use in subsequent processing steps. The particles 600 may be removed from the electrode 610 by simply removing the power, if they are large enough for gravity to overcome any adhesion forces holding them to the electrode. Alternatively, the liquid 620 may be used to wash the particles 600 from the elongated electrode 610 when the elongated electrode 610 is dipped into the liquid. In some cases, it may be necessary to agitate the electrode within the liquid.

For instance, small dielectric particles 600 frequently remain adhered to the electrode 610 even when the power is removed. In such a case, it is possible to remove the particles from the electrode by washing them off in liquid 620.

Target Having Charged Regions

Figure 23:
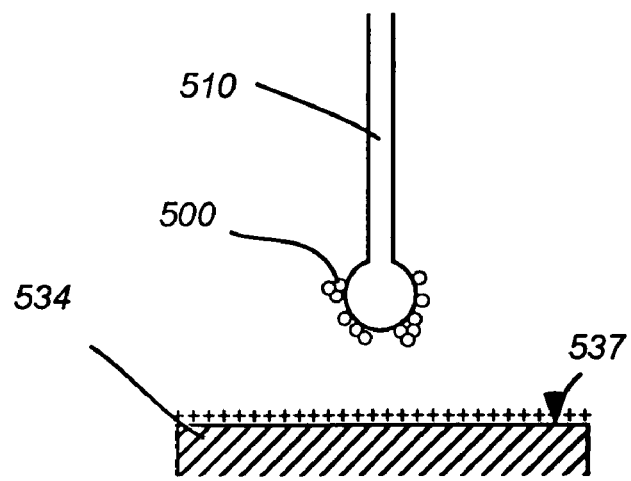
FIG. 23 shows schematically an electrode carrying particles and a target electrode that is charged, to attract manipulated particles to it.

FIG. 23 shows an elongated electrode 510, which carries on its surface particles 500. The bare electrode has previously been provided with a voltage to collect the particles by some suitable means, as described above. A charged, flat dielectric target 534 will receive the particles. Before deposition, the surface 537 of the target 534 has been charged with a charge by an appropriate method, for instance, by using a corona discharge device. The particles on the elongated electrode may carry a surface charge, as determined by experiment for the given parameters of the powder, electrode, duration of different stages, etc., discussed above. In such cases, it will generally be desirable to charge the target with an opposite polarity. In general, it is only necessary to dislodge the particles from the surface of the electrode to cause them to be deposited.

To deposit the transported particles 500 onto the surface 527 of the target 534, the former voltage of the transporting electrode 510 is eliminated, so that the manipulating electrode is electrically isolated. The particles are weakly held to the electrode by van der Waals adhesion forces and capillary forces.

The surface charge on the target 534 will give rise to a Coulombic force on oppositely charged particles, that act to pull the particles 500 toward the charged target surface 537. Both charged and uncharged particles will also experience a net force due to the spatially non-uniform electric field generated between the manipulating electrode 510 and the charged target surface 537. The corona ions deposited on the dielectric target region are uniformly distributed and immobile. As the manipulating electrode is brought near the charged target, the electric potential in the region between the nearest part of the electrode and the charged surface is changed. While the electric potential at the surface of the metal electrode is constant, the potential at the surface of the charged dielectric target may vary with position, and will be highest at the point nearest to the metal electrode. Without being limited to a particular theory, it is believed that this will give rise to a spatially non-uniform field that will act to move the particles towards the point of smallest spacing between the electrode and the target. As the particles begin to move along the electrode surface, the adhesive forces are reduced, and gravity will cause the particles to fall towards the target. As has been mentioned above, it is important in many applications for the amount of material that is deposited on the target 534 to be precisely measured. It has also been mentioned that in some cases, with Coulombic, or charge based manipulation methods, it is somewhat difficult to ensure repeatability, due to variations in charge caused by humidity and other variable environmental factors. One way to minimize some of these variability problems is to collect the particles by a dielectrophoretic method, so that the amount of particles collected onto the manipulating electrode is known to some degree of precision. Then, when the particles are deposited using a coulombic phenomenon, as discussed in connection with one aspect of FIG. 23, what must be done is to ensure that all of the collected particles are in fact deposited on the target. In that way, because the amount that was collected onto the electrode 510 was precisely controlled, the amount deposited on the target is also precisely known and controlled.

Figure 25:
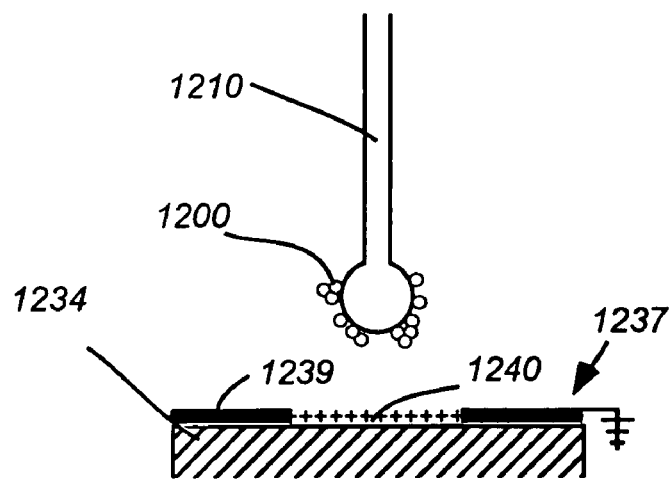
FIG. 25 shows schematically an electrode carrying particles and a target substrate containing a conductive film that is patterned, such that the conductive regions may be electrically grounded after charging to leave a surface charge on the exposed dielectric regions that will attract the collected particles.

FIG. 25 shows a set up that enables precise location of deposited particles. This set up would be used with a DC or AC voltage. A bare elongated electrode 1210, has collected a number of particles 1200. The electrode was maintained at a voltage to transport the particles from their collection location to the target. A dielectric target 1234 is provided with a patterned conductive film 1239 on its surface 1237, so that regions 1240 of the dielectric surface are exposed in a corresponding pattern to the film 1239 (exposed in places where film is not present). The entire surface 1237 is charged uniformly, such as by a corona discharge, and then the conductive portions 1239 are all grounded, thereby removing the charge from the conductive regions. The exposed patterned surface regions 1240 will retain their charge (positive, as shown).

As with the embodiment discussed above in connection with FIG. 23, the voltage to the handling electrode 510 is removed after the manipulating electrode is brought near to the target (as shown in FIG. 25) and the manipulating electrode 1210 is electrically isolated. Thus, as the elongated transporting electrode 1210 and transported particles 1200 are brought within proximity to the exposed target regions 1240, the particles 1200, will be drawn from the manipulating electrode 1210 to the exposed, charged regions 1240 of the target surface 1237. The particles need not be charged in order to be deposited on the target region by this method. Even if they are uncharged, they will be drawn to the charged region 1240 due to the spatially non-uniform field that arises, as discussed immediately above. However, if the particles are charged, it will generally be desired to charge the target regions with an opposite polarity to aid in deposition.

Figure 26:
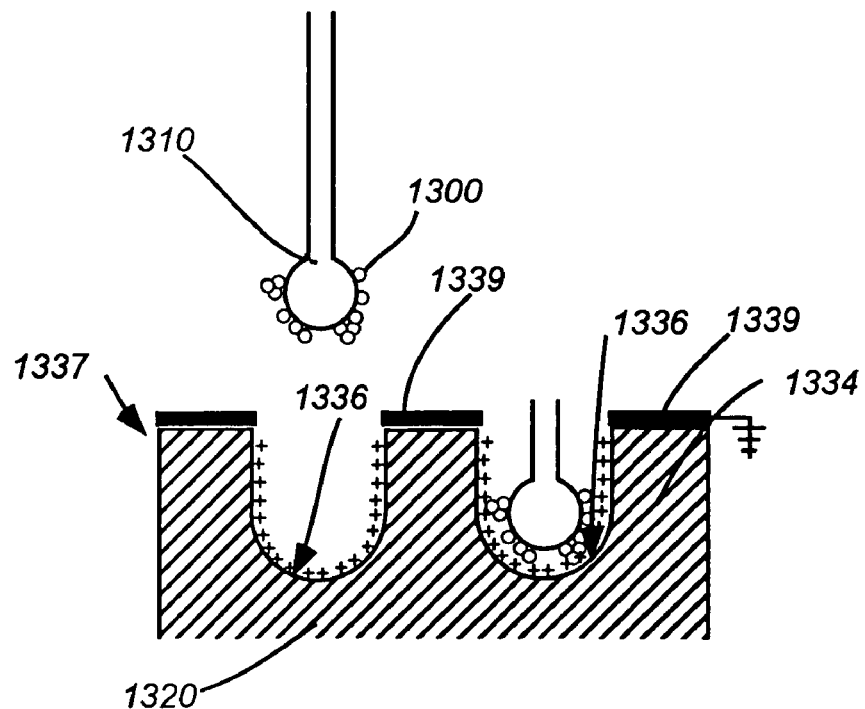
FIG. 26 shows schematically an electrode carrying particles and a target containing wells and a conductive layer outside of the wells, such that the conductive layer may be electrically grounded after charging to leave a surface charge in the wells that will attract the collected particles.

FIG. 26 shows a set up that allows for precise location of deposited particles within wells of a microtitre plate, exactly analogous to the situation explained with respect to FIG. 25. A bare electrode 1310, has collected a number of particles 1300. The electrode was maintained at a positive DC voltage for collection purposes. A dielectric target microtitre plate 1334 is provided with a patterned conductive film 1339 on its surface 1337; so that the well regions 1336 of the dielectric surface are exposed in a corresponding, mating pattern to the film 1339. The entire surface 1337 is charged uniformly, such as by a corona discharge, and then the conductive portions 1339 are all grounded, thereby removing the charge from the conductive regions. The exposed patterned well regions 1336 will retain their charge (positive, as shown). Thus, as the elongated electrode 1310 and transported particles 1300 are brought within proximity to the exposed well regions, the particles 1300, will be drawn from the electrode 1310 to the exposed, charged well regions 1336 of the target microtitre plate surface 1337. If the particles are charged, the well 335 is oppositely charged, and the force has a coulombic component. If the particles 1300 are not charged, then the force on them is due to the spatially non-uniform field (dielectrophoretic), as discussed above. It can be seen that in this manner, the elongated shape of the electrode 1310 can advantageously be used to place the particles deep within the wells 1336, which action could not conveniently be done with a planar electrode. The other considerations, discussed above in connection with FIG. 25, also apply to this embodiment.

Dielectric Covered Manipulating Electrode

Figure 27:
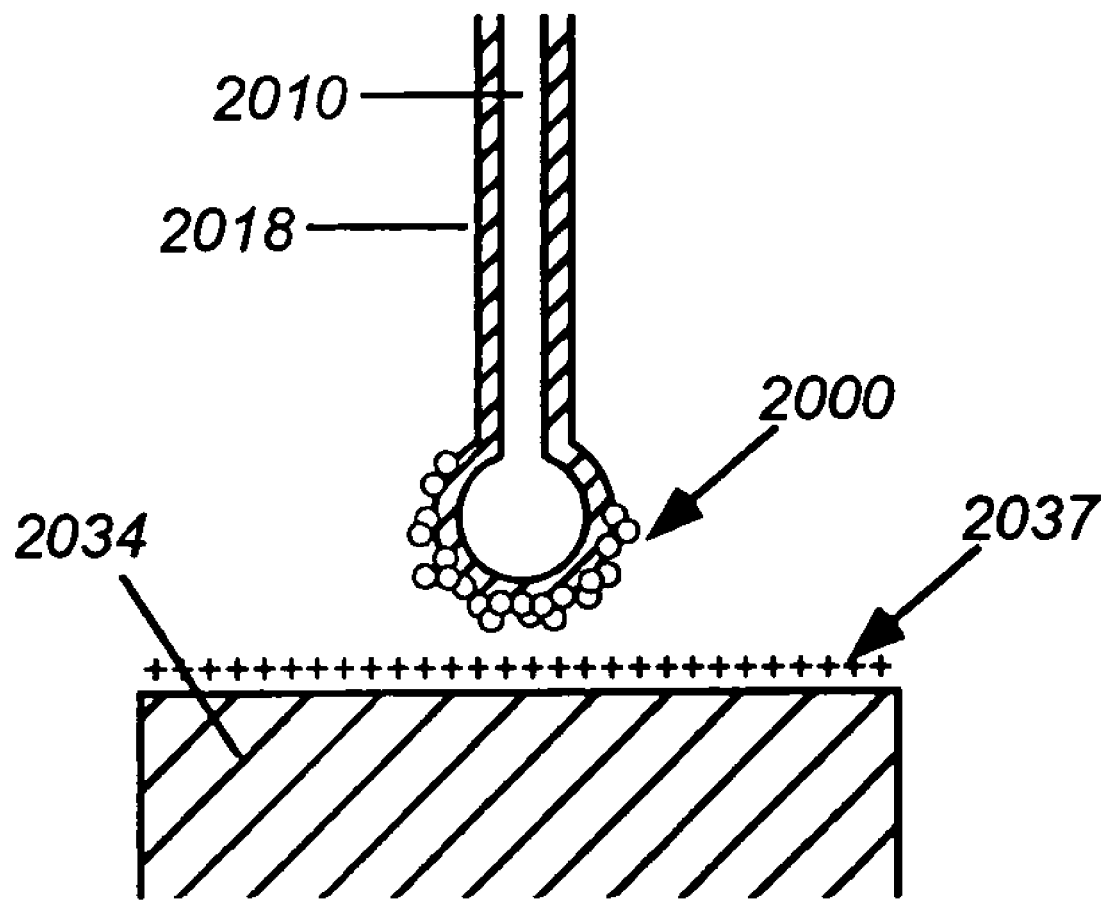
FIG. 27 shows schematically an arrangement for depositing particles onto a charged dielectric substrate similar to that shown in FIG. 23 but where the manipulating electrode bears a dielectric covering.

FIG. 27 shows an arrangement for depositing particles 2000 onto a dielectric substrate 2034. The substrate 2034 surface 2037 is charged, for instance by a corona discharge. If the collected particles carry a surface charge, it will generally be desirable to charge the substrate with the opposite polarity. The particles 2000 are transported by an elongated electrode 2010, which is covered by a dielectric coating 2018. The elongated electrode 2010 containing the collected particles 2000 is brought near to the target 2034, and the applied voltage used to collect the particles is removed immediately prior to deposition so that electrode 2010 is electrically isolated. This arrangement for deposition is essentially identical to that shown in connection with FIG. 23, discussed above, but for the dielectric covering. As discussed above, the dielectric covering helps to minimize some of the uncertainty regarding the charge carried by the particles 2000 being manipulated. Otherwise, its operation is essentially identical to that discussed above in connection with FIG. 23.

Figure 28:
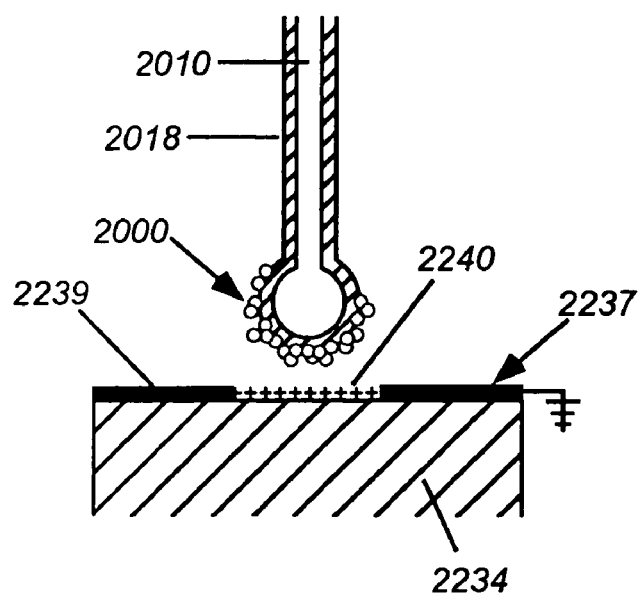
FIG. 28 shows schematically an arrangement for depositing particles onto a charged dielectric substrate, with a patterned conductive film at regions where deposition is not desired similar to that shown in FIG. 25, but where the manipulating electrode bears a dielectric covering.

A different arrangement is shown in FIG. 28, using a similar elongated electrode 2010 coated with a dielectric layer 2018. In this case, the target 2234 has a patterned surface 2237, with a conductive film that covers certain regions 2239 and leaves other regions 2240 bare. This embodiment is essentially identical to that disclosed above in connection with FIG. 25, except that, again, the dielectric covering 2018 prevents any surface charge present on the particles 2000 from discharging.

Figure 29:
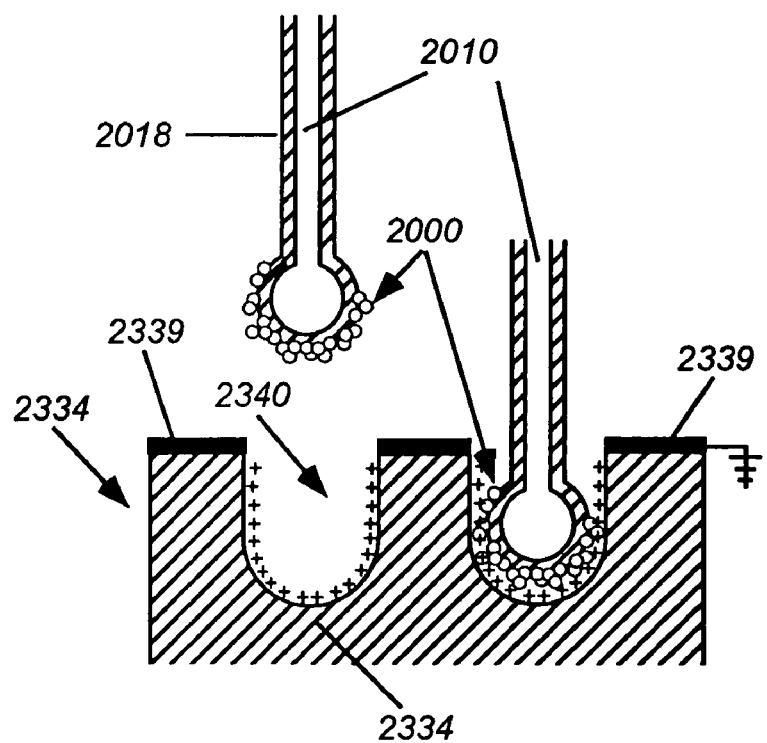
FIG. 29 shows schematically an arrangement for depositing particles onto a dielectric substrate with charged recesses, with a patterned conductive film at regions where deposition is not desired, similar to that shown in FIG. 26 but with the manipulating electrode bearing a dielectric covering.

FIG. 29 shows another arrangement with an elongated electrode 2010. The elongated electrode is coated with a dielectric layer 2018. The target 2334 is dielectric. In this case, it is provided with wells, 2340, such as a microtitre plate. The arrangement is identical to that shown above in connection with FIG. 26, except that the dielectric cover 2018 has been provided, with the same purpose and effect as the dielectric cover discussed above in connection with FIG. 28.

Both this FIG. 29 arrangement and that shown in FIG. 26 may be advantageously used in situations where the items to be transported are located relatively far up along the shank of the elongated electrode 2010 from the free end. This may occur, for instance, if the items are collected from an aerosol cloud, as shown in FIGS. 14 and 15, or if the shape of the electric field is such that it directs items away from the tip, and up along the shaft. This is because the charged portions of the wells will be relatively close to even those portions of the elongated electrode that are distant from the tip. Similarly, the arrangement shown in FIG. 24 can be used in this case, because the liquid in the wells will contact the portions of the elongated electrode distant from the tip.

Placement of Microelectronic Parts

An invention disclosed herein can be used to assemble microelectronic parts onto a recipient target, as shown schematically with reference to FIG. 30. The part 1400 is retained on an elongated electrode 1410, by which it has been collected as described in connection with FIG. 19A. A dielectric target 1434 has a surface 1437, which has bare regions 1440 and a pattern of conductive regions 1439. The pattern of conductive regions are coupled to a voltage source 1441 through a circuit that enables each individual conductive region 1439*a*, 1439*b* to be individually addressable, provided with a specific, different voltage potential. This selectivity capability may be accomplished by any suitable means, and is indicated by the small diamonds at the junctions between the connectors to the conductive regions 1439*a*, 1439*b* and the voltage source 1441. The voltage applied to the elongated electrode 1410 in order to collect the part is removed immediately before deposition takes place.

In one embodiment, the target 1434 is a semiconductor chip that has been made by any suitable means, either conventional or subsequently developed. Thus, it has electronically conducting pads and traces suitable for its ultimate use in electronic equipment, which pads can also be tailored to be exploited in the assembly of microelectronic components on the chip target 1434. The patterns of conductive regions 1439*a* and 1439*b* and non-conductive regions 1440 thus serve a dual purpose of helping to attract the components 1400 to the proper locations on the target chip during assembly, and also coupling the components to each other and other components in electronic circuits for use in the finished product.

Returning to a description of component deposition, during component deposition, a specific voltage is provided to each addressable region 1439*a*, 1439*b*, at appropriate times, so that the component is attracted to the desired addressable, e.g., region 1439*a*, and not to any other conductive regions, where it is not intended to deposit the particular component. Neither is the component attracted to the non-conductive regions 1440. In general, when a component is brought near to the target, only the specific, appropriate addressable region 1439 is set to a voltage that attracts the component. All of the other addressable regions are electrically isolated. This supplied voltage, in conjunction with suitably placed grounded electrodes, 1405, gives rise to a spatially non-uniform field, such that the force directs the dielectric body toward the desired target region 1439*b*.

FIG. 31 shows an arrangement similar to that shown in FIG. 30, also showing a dielectric target 1534. This target has a surface 1537 defined by shaped recesses 1539*a*, 1539*b*, that are shaped to mate with the shape of the component 1500 to be deposited. The component 1500 has a convex trapezoidal cross-section, as shown, and the recesses 1539*a*, 1539*b* have a concave trapezoidal cross-section, which matches that of the components 1500 to be deposited. The recesses 1539*a*, 1539*b* also are provided with addressable conductive material, which conductive material is part of a circuit, in the same manner as described in connection with FIG. 30. Thus, the voltage supply 1541 provides an appropriate voltage to the recess 1539*b* of the target 1534 where it is desired to deposit a component, which voltage establishes a field that attracts the component to the specific recess. The matching shape of the recess helps to more precisely locate the component as it is released from the transporting electrode 1510 (as described above, again, in connection with FIG. 30). The matching shape of the recess 1539 also helps to retain the component in the recess more securely, for instance, against disturbing forces due to jostling, vibration, and static charges generated during processing.

The elongated form of the electrode 1510 is particularly advantageous in connection with a target having recesses 1539, because it enables bringing the part 1500 into very close proximity to the deepest part of the recesses.

This method, using a dielectrophoretic force to attract particles to a target region, may also be employed to fill the wells of an drug-delivery device, such as that developed by Santini, et. al. (J. Santini, U.S. Pat. No. 5,797,898, cited above). FIG. 31 shows depositing a shaped component into an addressable recess 1539*b*. It is also possible to deposit a quantity of powder material 3300, such as shown in FIG. 32, into an addressable recessed region 3311 in an drug-delivery device 3370, which may, but need not be, implantable. This may be accomplished by bringing a manipulating electrode 3310, which has collected particles 3300 as discussed above in reference to FIG. 11, near to the recessed region 3311, which contains a grounded conductive membrane 3313. The spatially non-uniform electric field generated between the manipulating electrode 3310, which is maintained at the collecting voltage by the voltage source 3341 and the membrane 3313, will draw the particles 3313 toward the membrane, thus filling the recessed region 3311.

FIG. 33 shows schematically another method of filling recessed regions 3311 of a microchip 3370 with powder particles 3300. In this case the particles have been collected by a two-element manipulating electrode 3360, such as the two pin electrode described in reference to FIG. 1M. The manipulating electrode 3360 is brought near the addressable recess 3311. At the instant the collecting voltage $V_1$ provided by source 3343 is removed, a depositing voltage $V_2$ provided by source 3345 is applied between a counter-electrode 3314, located relatively far from the recess 3311, and the conductive membrane 3313. This generates a spatially non-uniform field in the vicinity of the membrane 3313, which acts to draw the particles 3300 toward the membrane 3313, thus filling the recess 3311.

Figure 30:
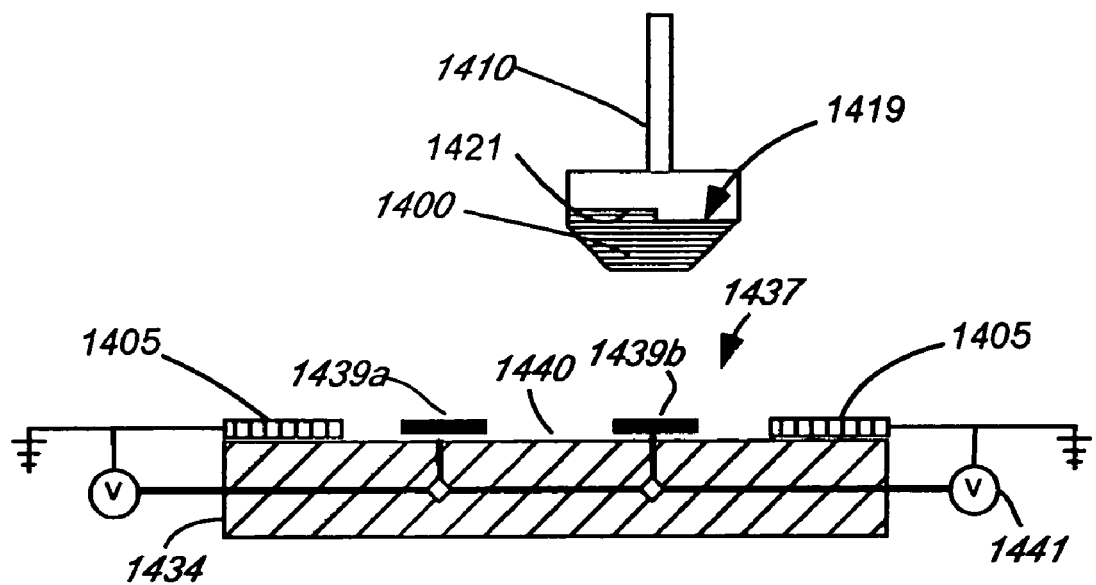
FIG. 30 shows schematically an electrode carrying a microelectronic part and a target containing addressable electrodes, such that a voltage may be selectively applied to each individual addressable electrode to attract a manipulated part.
Figure 34:
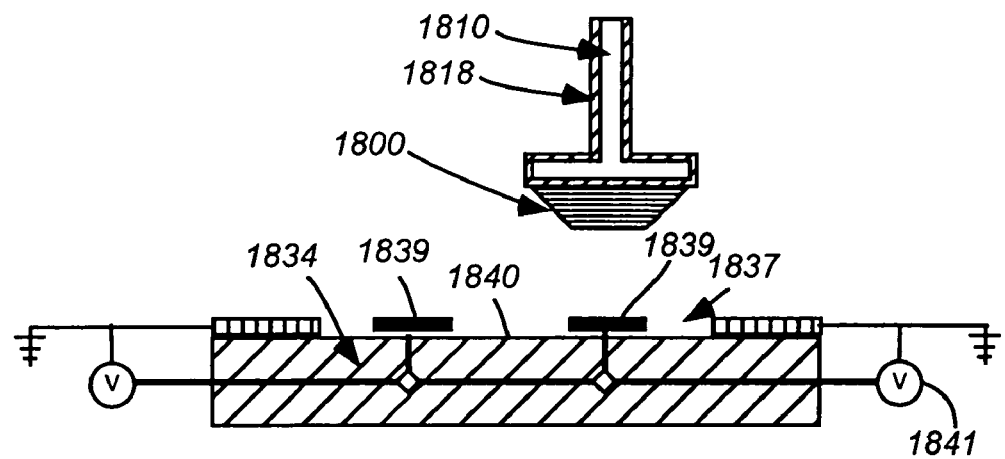
FIG. 34 shows schematically an electrode that bears a dielectric coating carrying a microelectronic part and a target containing addressable electrodes, such that a voltage may be selectively applied to each individual electrode to attract a manipulated part.

FIG. 34 shows an arrangement similar to that shown in FIG. 30. However, in FIG. 34, an elongated electrode 1810 bears a dielectric coating layer 1818. The operation of this embodiment is otherwise identical to that described above in connection with FIG. 30, with the dielectric coating serving to reduce uncertainty regarding the charge of the transported component 1800.

Figure 31:
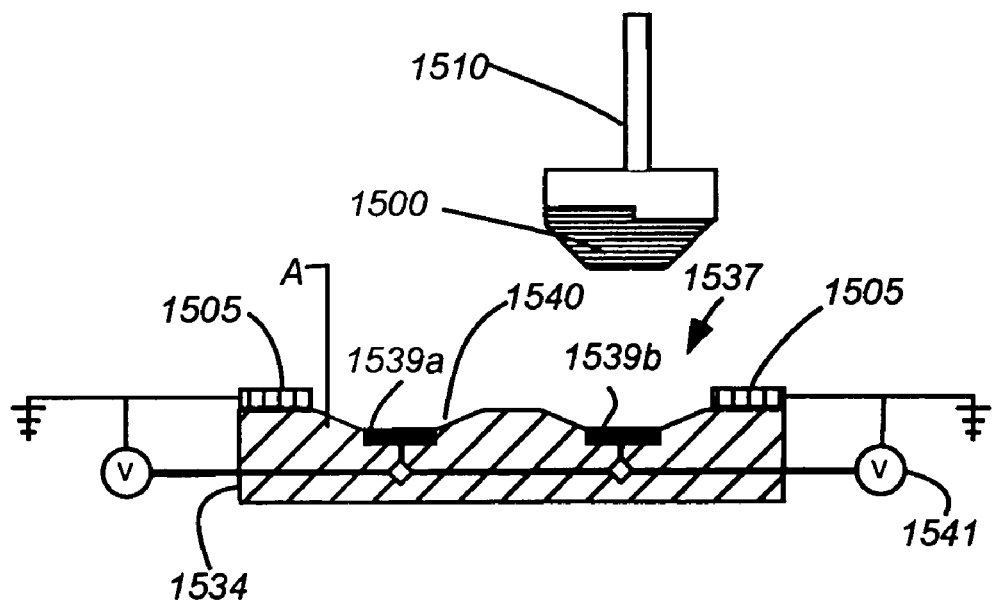
FIG. 31 shows schematically an electrode and microelectronic part and target, similar to that shown in FIG. 30, with shaped, recessed target regions.
Figure 32:
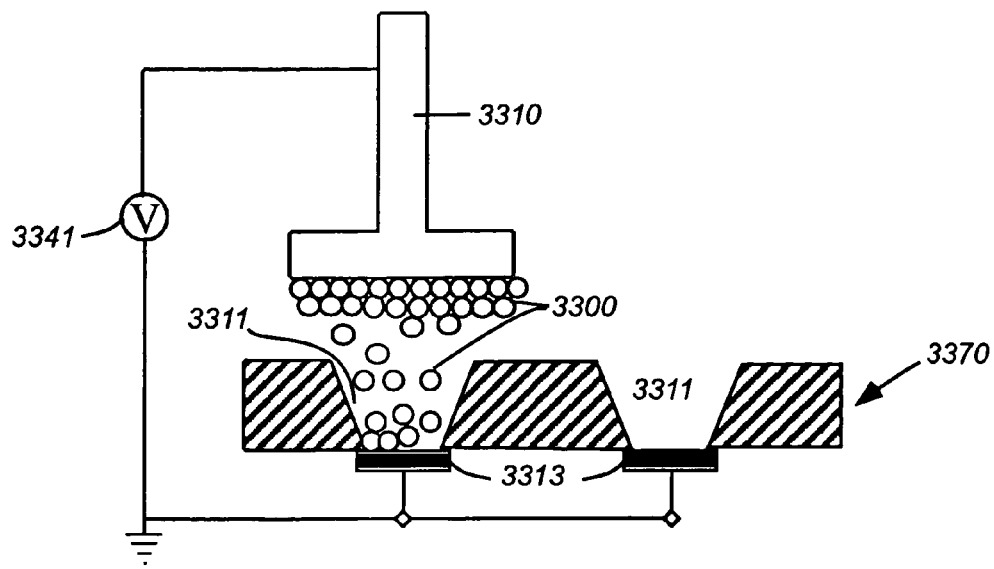
FIG. 32 shows, schematically, depositing particles into a recess of a pharmaceutical delivery microchip, using an elongated single element electrode.
Figure 33:
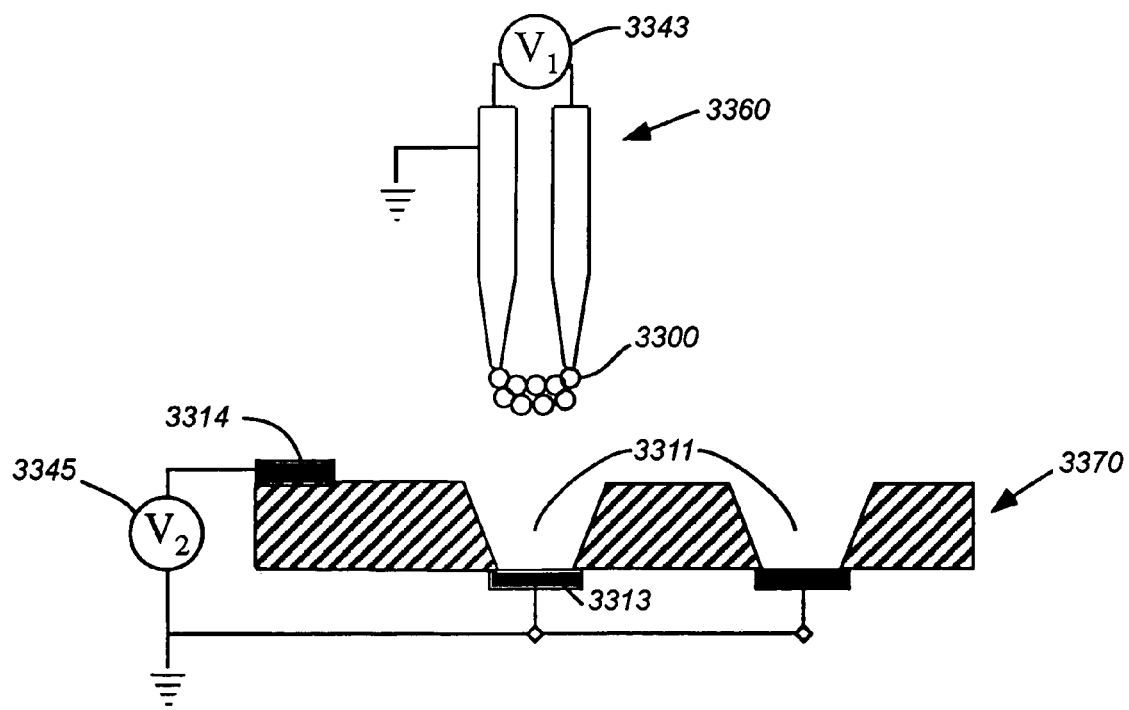
FIG. 33 shows, schematically, depositing particles into a recess of a microchip, using an elongated two element electrode.
Figure 35:
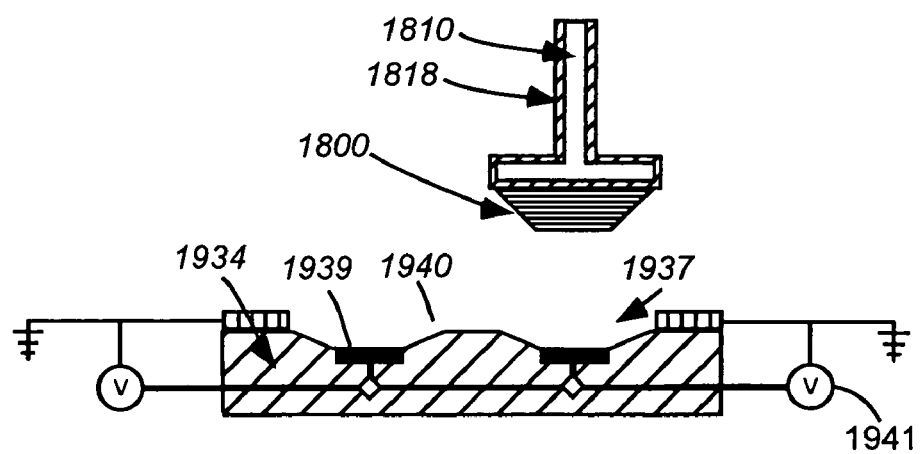
FIG. 35 shows schematically an arrangement that is similar to that shown in FIG. 34, where the target has a surface that is defined by shaped recesses.

FIG. 35 shows an arrangement that is similar to that shown in FIG. 34, in that an elongated electrode 1810, which is coated with a dielectric layer 1818 carries a microelectronic part 1800 to be deposited on a dielectric target 1934. In this case, the target 1934 has a surface 1937 that is defined by shaped recesses 1939, each of which has an addressable conductive region similar to the arrangement shown in FIG. 31. The addressable recesses 1939 are coupled to a voltage source 1941 in the same manner as is described in connection with FIG. 31. The dielectric coating 1818 functions in the same manner as described in connection with FIG. 34.

Exploiting Dielectrophoretic Force to Deposit Items on a Target Particles

Figure 36:
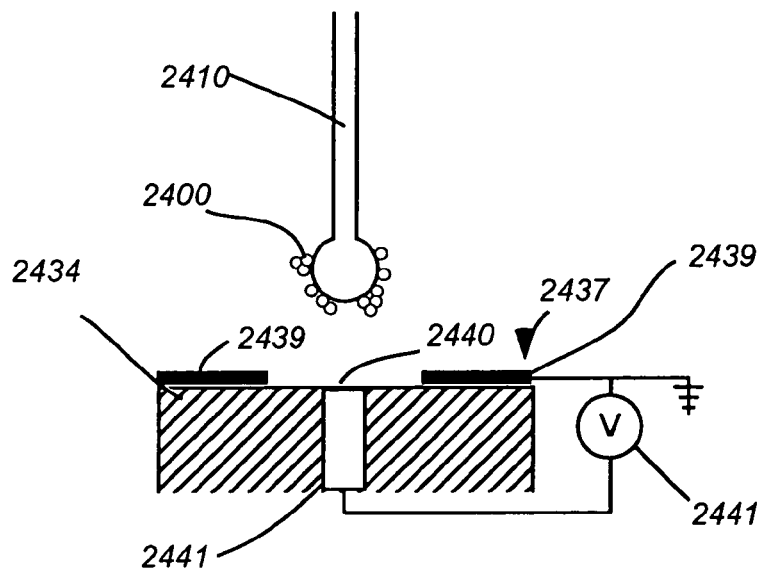
FIG. 36 shows schematically, a generally flat target having an electrode pattern that creates dielectrophoretic force attracting particles to be deposited to it.

FIG. 36 shows, schematically, depositing items 2400 on a target 2434 by exploiting a dielectrophoretic force. The manipulating electrode 2410 carries the collected particles 2400, as in the other examples. Upon removal of the applied collecting potential, the particles are retained on the manipulating electrode 2410 by surface adhesive forces. The target 2434 has on its surface 2437 a patterned, conductive region 2439 where it is desired that particles not be attracted, which can be grounded, as shown. A prime target region 2440 is associated with a target electrode 2441, which is shaped and located relative to grounded portions to produce a spatially non-uniform electric field that will exert a dielectrophoretic force on the particles 2400 carried on the manipulating electrode 2410. The exact electrode shape or class of shapes that will give rise to such forces will depend on the geometry of the manipulating electrode 2410, the particle shape, size, dielectric constant, etc. However, it is believed that what is required is to create a field that has converging field lines adjacent the tip of the target electrode 2441. It is believed that such a field would be created by a target electrode with a small spatial extent along at least one dimension, relative to the grounded conductive regions. Rather than a single electrode, an array of smaller electrodes could be provided. Thus, as the particles are brought near to the target electrode 2441, they are drawn to it by the dielectrophoretic force. The force must be large enough to overcome any adhesion force.

If the particles are retained on the manipulating electrode 2410 by a force that arises only when voltage is supplied to the manipulating electrode 2410, that voltage can be removed when the manipulating electrode 2410 is close enough to the target electrode 2441 for the dielectrophoretic force to draw the particles 2400 to it. An advantage of this method and apparatus for depositing particles, is that it does not depend on the surface charge of the items to be manipulated. A force will arise that will tend to deposit the particles onto the target 2434. Rather than grounding the patterned regions, they can be provided with a different voltage, by providing an additional voltage source, in place of the ground reference, as long as a spatially non-uniform field arises.

Figure 37:
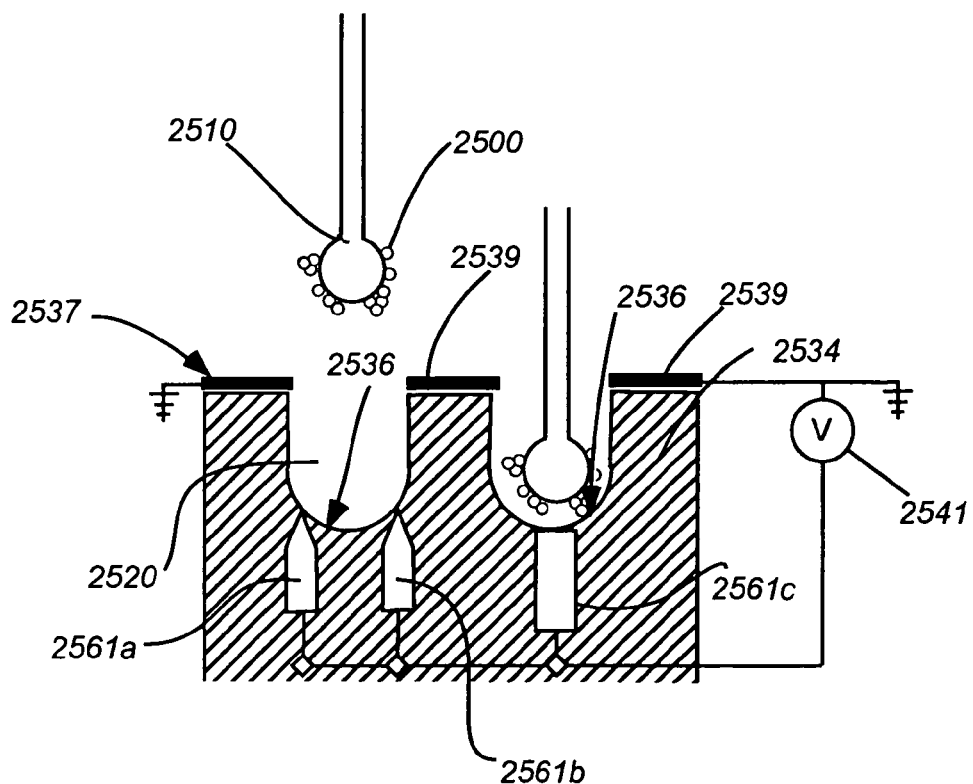
FIG. 37 shows schematically, a portion of a microtitre tray type target having an electrode pattern that creates a dielectrophoretic force attracting particles to be deposited to individual wells of the tray, showing optionally one of the wells containing multiple target electrodes and one containing a single electrode.

FIG. 37 shows another apparatus that exploits dielectrophoretic force to deposit particles 2500 on a target 2534. This target is a microtitre tray, with wells 2536. It also has a pattern of conductive regions 2539 on its surface at location where it is not desired that particles be deposited, which also can be grounded as shown. A target electrode 2561 is provided adjacent to the bottom of the well 2536, so that it will create a dielectrophoretic field that will draw particles 2500 to it. In general, the same considerations apply as in the case of the generally flat surface target 2434, shown in FIG. 36, except that the shape of the wells will tend to help retain particles in the wells. FIG. 37 shows schematically a single electrode 2561c adjacent one well (right), or, alternatively, a double electrode 2561a and 2561b adjacent a different well (left). More complicated electrode configurations are also possible. It is possible to selectively energize the target electrodes 2561a and 2561b and 2561, as indicated by the diamonds at their terminals in order to deposit particles only in selected wells.

Microelectronic Parts

Figure 38:
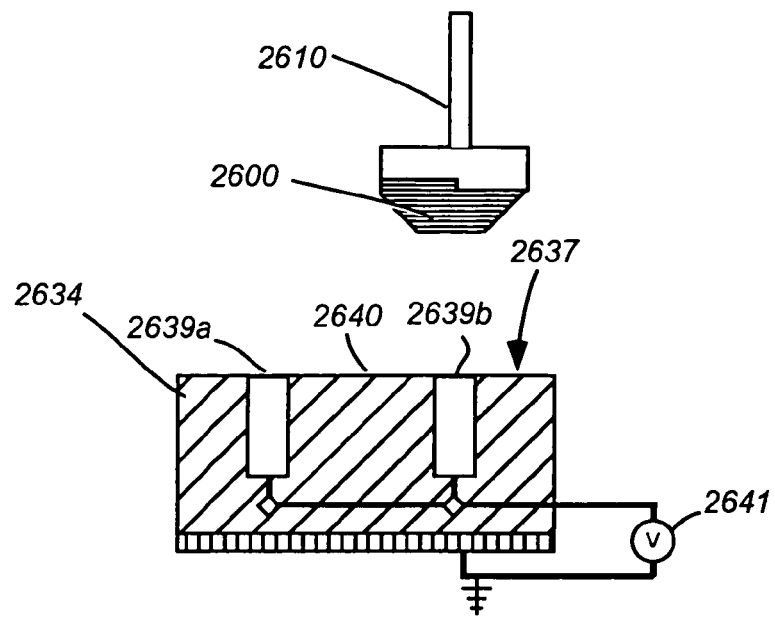
FIG. 38 shows schematically, a target having a generally flat surface with target regions defined by an electrode pattern that creates dielectrophoretic force attracting microelectronic parts to be deposited to selectable target regions.

FIG. 38 shows an apparatus that is similar to that shown above in FIG. 36, but that is adapted for depositing microelectronic parts 2600 on the surface 2637 of a target 2634. This apparatus and method also has the advantage that it will deposit microelectronic parts onto a target 2634 without the parts needing to be charged. It works essentially the same way as does the apparatus described in FIG. 36. A voltage bias is provided by voltage source 2641 to the selected target electrode 2639b, which gives rise to an electric field that has a non-zero gradient with converging field lines at the locus of the tip of the target electrode 2639b. The manipulating electrode 2610 is drawn near to it, and any power to it is removed. The dielectrophoretic force generated by the field on the microelectronic part 2600 draws the part to the target electrode 2639b. Typically, with microelectronic parts, the target 2639b is a circuit element used to electrically control the device deposited on the target region. The circuits can be designed to provide appropriate voltages selectively to one or more of a plurality of target electrodes 2639a, 2639b, etc., to attract and deposit the part where desired. Thus, as discussed above, the circuit elements are used in both the primary function of the deposited microelectronic part, and also for fabrication of the device.

Figure 39:
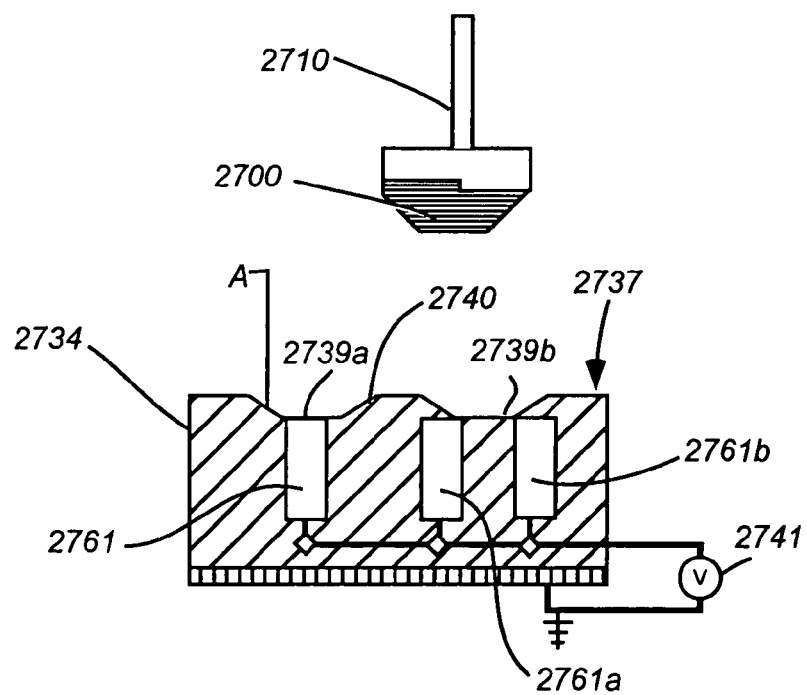
FIG. 39 shows schematically, a target having a surface with shaped recesses, and an electrode pattern that creates dielectrophoretic force attracting microelectronic parts to selectable recesses of the target.

FIG. 39 shows a similar apparatus to that shown in FIG. 38, except that the surface 2737 of the chip is shaped with recesses 2739a, 2739b, which are shaped to mate with the shape of the microelectronic part 2700, as described above in connection with FIG. 31. Each recess is provided with at least one target electrode 2761, either singly, or, a plurality, as shown by 2761a and 2761b. Only two are shown, but any convenient number can be used. The target electrodes 2761 are selectively energized, to generate a field that establishes a dielectrophoretic force on the microelectronic part 2700, drawing it to the intended recess. The mating shape of the recess further helps to seat the component when it is nearly in place.

Figure 40A:
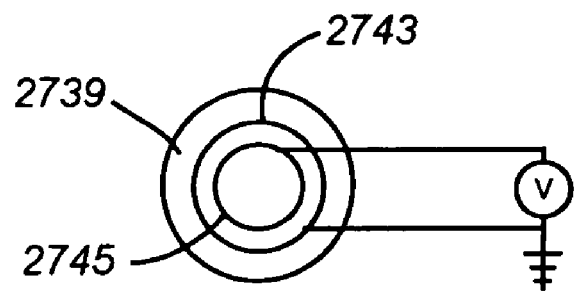
FIG. 40A shows schematically a target having a generic recess, such as an electronic chip, a well of a microtitre tray, or a microchip, with concentric electrodes arranged to produce a spatially non-uniform field.
Figure 40B:
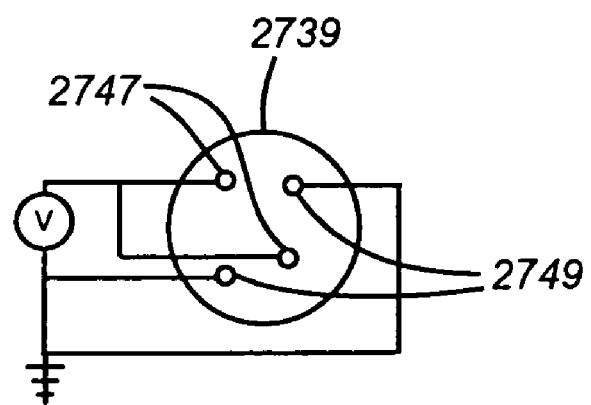
FIG. 40B shows schematically a target having a generic recess, such as an electronic chip, a well of a microtitre tray, or a microchip, with spaced-apart pin electrodes arranged to produce a spatially non-uniform field.

Rather than point type electrodes, any convenient configuration can be used. FIG. 40A is a schematic plan view of a circular recess 2739, having a pair of circular electrodes 2743 and 2745. FIG. 40B shows a plurality of separate electrodes 2747 and 2749, distributed around the circumference of the recess, provided with an appropriate bias voltage to generate a field that converges at the recess 2739.

In all of the cases shown in FIGS. 36, 37, 38 and 39, exploiting a dielectrophoretic force to deposit items, the bias voltage can be AC, or DC, either positive or negative. Also, in all of the cases shown in FIGS. 36, 37, 38 and 39, rather than using a bare manipulating electrode, such as 2610, an electrode that is covered with a dielectric, such as shown and discussed in connection with FIGS. 27, 28, 29, 34, 35, for the same reason. That reason is primarily to minimize uncertainty regarding the charge carried by the manipulated item.

Manipulation and Calibration Techniques

Many techniques and aspects of the inventions have been described herein. The person skilled in the art will understand that many of these techniques can be used with other disclosed techniques, even if they have not been described as being used together. Thus, the fact that a sub-combination of features that are described separately, may not be described in sub-combination, does not mean that the inventors do not regard any such sub-combination as an invention that is disclosed herein.

For instance, any of the following techniques and features can be used with any of the others: unitary manipulating electrode; multiple element electrode; elongated electrode; non-elongated electrode that gives rise to spatially non-uniform field; dielectric sheathing on any electrode, including target and manipulating electrodes; particles to be collected supported in a volume; particles to be collected dispersed in a gas; manipulating electrodes used singly, or in a multi-electrode array; charged particles to be collected; uncharged particles to be collected; particles whose charge is not known to be collected; AC or DC bias of manipulating electrode, of either polarity; particles are micron scale, generally spherical, or threads or sheets, with at least one micron scale dimension; manipulating electrode being part of a pharmaceutical-delivery device, implantable or not; manipulating single items or large numbers of particles; flat targets; shaped targets, with recesses, such as microtitre trays and implantable drug-delivery devices and electronic circuit chip elements; charged targets; uncharged targets; targets with patterned electrodes thereon; targets carrying electrodes that give rise to spatially non-uniform field; manipulating powders, particles, microelectronic parts, medicaments, and other pharmaceutical agents. Any collection method can be used with any compatible deposition method and apparatus.

Some of the inventions disclosed herein are methods of manipulating micron scale items. However, other inventions disclosed herein are methods of designing processes for manipulating micron scale items. In other words, the process design inventions are methods for designing manufacturing processes. For instance, it is disclosed how a designer, challenged with the task of manipulating micron scale items of a specified size, dielectric constant, etc., will proceed to design the process to manipulate the part. The disclosure herein teaches how the designer shall select an electrode configuration, geometry and size, as well as appropriate process parameters, such as separation and voltage. The designer is also informed by this disclosure of the effects of static surface charge, and myriad other factors that can be considered in the selection of collection and deposition techniques. Thus, the designer is taught how to manipulate micron scale items using spatially non-uniform electric fields.

For instance, if the designer wants to dispense microgram quantities of powder, the designer might use the disc and plate (FIG. 11) or disc and ring (FIG. 9A) configuration. (This is just an example. Depending on the sizes and geometries, the decisions might be made differently). Several routine experiments can then be done to determine whether +DC, −DC, or AC would be best to collect and retain particles on the electrode. The designer would then do a simple experiment to determine if the particles were subsequently deposited as soon as the power is turned off. If so, no other steps would be necessary except to adjust the height H above the powder bed and/or the size of the electrode to fine-tune the amount collected, and thus, dispensed. If the particles did not fall off of the electrode by removing the potential, then an additional force would be necessary to remove the particles. If appropriate to the process, the electrodes with their collected particles would be dipped into liquid in wells (FIG. 24). If it were necessary to maintain a completely dry process, the target regions would be charged to remove the particles (FIGS. 23, 25, 26, 28, 29, etc.) In practice, the designer could easily try each polarity (positive, negative) to determine which was most effective.

Alternatively, if it were feasible to place an electrode in or near the target region, the electrode could be designed to create a spatially non-uniform field and dielectrophoretic force on the particles to direct them towards the target (FIGS. 30, 31, 32, 33, 36, 37, 38, 39).

If milligram quantities were required (again, just as an example, based on the parameters that have been examined and shown in the above experiments), the designer would use one of the two-electrode configurations (such as, parallel pins (FIG. 1A, parallel loops, FIG. 7A, disc and ring FIG. 9A) and an AC potential. The particles in such a case are suspended between the two electrodes by a dielectrophoretic force, which will typically be removed when the voltage is removed. Thus, essentially regardless of any charges on the particle surfaces, or a few particles that adhere to the electrodes themselves, the designed process will consistently deposit a very reproducible amount.

All of these tools relate to the inventions of designing a process for manipulating micron scale items.

As discussed previously, for high throughput materials development and synthesis, it is necessary to deposit small quantities of particulate materials into the wells of a microtitre tray with some degree of precision. A typical procedure for such an application would be to select an appropriate electrode configuration and set of process parameters (such as the voltage and height above the powder bed), then to maintain constant conditions for collection and dispensing into each well. At least one well, and possibly multiple wells on each filled tray will be reserved for calibration, while the rest of the wells will be used for testing. The amount of powder in each calibration well will then be measured to determine the statistical variation in the amount dispensed, which can then be factored into the experimental results acquired from the test wells. This allows for a rapid, yet accurate method for testing and developing materials on a small scale.

Partial Summary

Thus, numerous embodiments of numerous inventions have been described. The following is a partial summary of the foregoing and of some of the embodiments of some of the inventions.

One invention is a method of manipulating micron scale items having a dielectric constant greater than that of an environment in which they are to be manipulated, comprising the steps of: providing a quantity of the items in a region within the environment and providing a manipulating electrode at a point near to the region. The manipulating electrode comprises: a first electrode conducting element; and, spaced from the first electrode conducting element, a second, counter electrode conducting element, the first and second conducting elements having surfaces, such that any two that face each other, are shaped, sized and spaced such that the spacing between them is large relative to the extent of either facing surface, in any one dimension. A voltage is applied to the electrode, thereby attracting the plurality of items to the electrode, upon which they become retained. In some cases, it is helpful if at least one dimension of the first electrode conducting element is small relative to at least one dimension of the second electrode conducting element. By small, regarding the relative size of the two electrodes, it is meant less than on-half, and preferably, less than one eighth. By large, regarding the spacing between electrodes, it is meant at least twice, preferably four times, and most preferably at least eight times.

Variations of this invention include a first, elongated electrode. In some cases, the second electrode is also elongated. In others, it is extended in two dimensions, substantially perpendicular to the elongation of the first, such as a plate. In such a case, items to be manipulated are typically provided between the elongated and the plate like electrode, for instance in a recess of the plate. Inventions that incorporate two elongated electrodes may have them parallel to each other, for instance a pair of pins, or loops. If loops, they may also extend along a dimension perpendicular to that of the initial elongation, which extending dimension may actually be greater than the first. Using inventions that are elongated, it is typical to provide items to be manipulated adjacent a terminal free end of elongated electrodes. Another inventive method uses an elongated electrode, terminated with a disc, circumscribed by a ring, which disc and ring act as an electrode pair.

Method inventions disclosed herein provide a voltage between the electrodes. The voltage can be applied between an elongated electrode and a plate like electrode, or between two elongated electrode conducting elements. In either case, the voltage can be either DC, or AC, with AC being somewhat favored if parallel electrodes are used, and DC if an elongated and a plate like electrode pair are used, although this preference is not absolute, and the opposite combinations can be used.

In the case of parallel conducting elements, items are typically attracted to the conducting elements and to the spaces between them.

According to various inventions disclosed here, once items are attracted to and retained on the manipulating electrode, it is moved, relative to the item support, either by moving the electrode, or the support, thereby disengaging the items from the source, and any non-attracted items.

Other inventions disclosed are methods for depositing such retained items on a target. The target can be one with discrete target regions, such as a microtitre tray, a microchip, or a semiconductor chip, or one with a unitary target region, or a plurality of planar regions. If a recess, it may contain a fluid, and the items retained on the electrode can be removed by immersing the electrode end into the fluid. Alternatively, in some cases items can be released by removing the applied voltage. If the target has multiple receptacles, the collection method can be calibrated by measuring the amount deposited into a selected plurality of recesses. If there are no recesses, then calibration can be conducted by measuring the results of one or more discrete deposition events.

The conducting electrodes can be provided with a dielectric cover. The amount collected can be selectably varied by changing the separation between the manipulating electrode and the items to be collected at the time voltage is applied to the electrode, or by changing the voltage applied, its frequency, or the size of the electrode, or, the spacing between any conducting elements of electrodes made up of a plurality of conducting elements.

The inventions include manipulating granular, threadlike and sheet materials, including such selected from the group consisting of excipients, proteins, salts, ceramic powder, pigments, catalysts, adhesives and phosphors.

The collecting electrode can be a membrane of a microchip, in which case the recess is sealed after it is filled.

Yet another invention is also a method of manipulating items, comprising the steps of providing a quantity of the items in a region within an environment; providing a manipulating electrode at a point near to the region, the manipulating electrode configured such that when positioned at the point near to the region, and a voltage is applied to the electrode, an electric field is generated whose square has a non-zero gradient, sufficiently large that a force is generated to lift a plurality of the items against gravity, regardless of the surface charge condition of the items. A voltage is applied to the electrode, thereby attracting the plurality of items to the electrode, upon which they are retained.

Another invention is similar. The electrode is shaped and sized to generate a spatially non-uniform field in the region in which the items reside, thereby attracting them to the electrode. This may be characterized as a dielectrophoretic force.

In some of the inventions disclosed herein, items will be attracted and retained without regard to their surface charge, or the polarity of the voltage applied, or the relation thereto. They will be attracted and retained whether they are neutral, or charged, positively, or negatively. Thus, the practitioner need not worry about the precise surface charge of the items, and need take no special steps to impart or measure any such charge.

Another invention is to provide a manipulating electrode that gives rise to a field having a gradient that is sufficiently large to attract such dielectric particles to it, even against the force of gravity. Such an electrode may be elongated, and may include a single conducting element, or a plurality, which may be parallel, such as pins or loops.

Yet another invention is a method of manipulating dielectric items by using an elongated manipulating electrode, applying a voltage thereto, attracting the particles to it from a region in which they reside, and then moving the electrode relative to the region, thereby collecting the items. Again, the electrode can be single or double, pins, loops or plates. In connection with this invention, the items are located in a region having a spatially non-uniform field, which will arise near the free terminal end of the elongated electrode. The items may be dispersed in a fluid cloud, in which the electrode is inserted, such as an aerosol cloud.

Still another invention is a method of collecting micron scale items having a dielectric constant greater than that of an environment in which they are to be manipulated, comprising the steps of: providing a quantity of the items in a region within the environment, and providing a pharmaceutical delivery microchip having a conductive membrane within a recess, at a point where the recess is near to the region, the conductive membrane configured such that when positioned at the point near to the region and a voltage is applied to the membrane, an electric field is generated that is sufficient to generate a force that is large enough to lift a plurality of the items against gravity, away from the region. A voltage is applied to the conductive membrane, thereby attracting the plurality of items to the membrane and into the recess, in which the membrane is located. In one version, the conductive membrane is located at a closed end of a recess, above the region in which the items are retained, and the recess having an opening that is arranged facing the region, such that the items are attracted against the force of gravity into the recess of the pharmaceutical delivery microchip. The microchip may have one or a plurality of the conductive membranes, each located within a respective recess. If a plurality, one, all, or a selected plurality may be simultaneously filled. Typically, a counter electrode is provided, near to the quantity of items, and a voltage is provided between the membrane and the counter electrode.

The foregoing summary description has focused on the method aspects of the inventions described. Related apparatus inventions also are disclosed. For instance, the apparatus may include an electrode that generates a spatially non-uniform field. Alternatively, an electrode may be provided that generates a non-zero gradient, which gives rise to a force that attracts dielectric particles. Alternatively, an electrode may be provided that generates a dielectrophoretic force that attracts dielectric particles. Or, the electrode generates a force that attracts particles without regard to their charge polarity. These may be alternate formulations of the same apparatus, but, in some cases, there may be differences.

An apparatus invention has an elongated electrode, in the various configurations described: single, double, multiple, parallel, extending and perpendicular, pins, loops, disc and circumscribing ring, plates. The items to be collected may be supported on a support that is adjacent the terminal end of an elongated electrode component, or that is near to a counter electrode that is spatially extended in two dimensions perpendicular to the elongated electrode.

Another invention also includes an x-y-z transport stage for one or all of the item supply module and the electrode support module, for collecting items, and for the target module, for depositing items. The invention may include a target, with whatever target is appropriate for the items to be collected. It may be a multi recess target, such as a microtitre tray, or a microchip, or a semiconductor chip for a surface mount device. The recesses may be sized so that an elongated electrode may be advanced into them. The target may include conductive elements to direct deposited items away from certain regions and toward other regions, such as the wells of a microtitre tray, or the connector pads for a surface mount microelectronic device.

According to another invention, the target includes target electrodes that give rise to an electric field that attracts items to it, without regard to the surface charge condition of the items. This field may be considered to be spatially non-uniform, and thus, giving rise to a dielectrophoretic force. It may also be considered to be one that has a significantly non-zero gradient, which also gives rise to such a force.

An apparatus invention includes a couple to a voltage supply, and a switch to disconnect the supply. Another invention includes the supply itself, which may be AC or DC.

Another invention includes a manipulating electrode having two parallel elements, such as pins or loops, with a spacing adjuster, for adjusting the distance therebetween.

Another invention disclosed is a target apparatus itself, for receiving deposited micron scale items. It has a plurality of target regions; an interconnected surface portion between the target regions; and a conducting element substantially covering the interconnected surface potion, such that substantially all of it is commonly conductively coupled. The target regions can be recesses, such as the wells of a microtitre tray, or a microchip.

Still another invention is a method for depositing micron scale items on a target comprising the steps of: providing a target, generally as described immediately above, and then providing a substantially uniform surface charge to the entire surface of the target, including the target regions and the interconnected surface portion. Next, a common voltage is provided to the interconnected surface portion through the conducting element, such that the target regions retain the uniform surface charge, and the interconnected surface portion does not. At least one item retained on a manipulating electrode is provided adjacent a target region of the target, such that it is drawn from the manipulating electrode to the target region and directed away from the interconnected surface portion. The target regions can be wells, as described above, and the step of providing the item can be accomplished by inserting the electrode into the well.

Another invention disclosed is also a target apparatus for receiving deposited items, having at least one target region. Adjacent the at least one target region, is a target electrode, configured to establish, when a voltage is provided thereto, a surrounding electric field that gives rise to a dielectrophoretic force upon an item retained upon the manipulating electrode, when the manipulating electrode is positioned adjacent the target region, sufficient to dislodge the item from the manipulating electrode, without regard to the surface charge condition of the item and to attract the item into the target region. The target electrode may be elongated, single, or a pair. It might also be concentric conducting elements. It may include these conducting elements in a microtitre tray or microchip, adjacent a recess thereof, or a component connector of a semiconductor chip. The target may include a shaped recess, for instance shaped to mate with a microelectronic part, if the target is a circuit element. The invention also may include components for selectably coupling the target electrode, or electrodes, to a voltage source, for energization of selected electrodes, for filling of selected recesses or locations.

Another invention hereof is a method of using a target, as described immediately above. A manipulating electrode upon which such an item is retained, is provided adjacent the target region. Such a target is provided, and a manipulating electrode upon which such an item is retained, is brought to be adjacent the target region. A voltage is provided to the target electrode, such that the retained item is drawn from the manipulating electrode to the target electrode.

Still another invention is an apparatus for removing micron scale items having a dielectric constant greater than that of a fluid in which they are dispersed, from the fluid. The apparatus comprises: an array of collecting electrodes, each comprising: a first electrode conducting element; and spaced from the first electrode conducting element, a second, counter electrode conducting element, the first and second conducting elements having surfaces that face each other, the facing surfaces being shaped, sized and spaced such that the spacing between them is large relative to the extent of either facing surface, in any one dimension. The invention also includes a means for coupling a voltage source to the electrodes of the array to establish a voltage between the first and second electrode conducting elements; and a fluid conduction module arranged relative to the array such that it conducts the fluid past the array such that the micron scale items pass near to the collecting electrodes of the array.

Of course, another invention is a method of cleaning a fluid, by using such an apparatus, including the steps of providing such an apparatus, providing such a voltage, and conducting such fluid past the array such that the micron scale items pass near to the collecting electrodes of the array while the voltage is provided, to attract the dielectric items to the collecting electrodes, thereby removing the micron scale items from the fluid.

Another invention is an apparatus for collecting micron scale items having a dielectric constant greater than that of a fluid in which they are dispersed, from the fluid. It comprises: a collecting electrode, comprising: a first electrode conducting element; and spaced from the first electrode conducting element, a second, counter electrode conducting element, the first and second conducting elements having surfaces that face each other, the facing surfaces being shaped, sized and spaced such that the spacing between them is large relative to the extent of either facing surface, in any one dimension. There is also a means for a coupling a voltage source to the electrodes of the array to establish a voltage between the first and second electrode conducting elements.

Another invention is a method of using the apparatus described immediately above, which includes the steps of providing such an apparatus with a voltage between the first and second electrode conducting elements and providing the conducting elements within the fluid adjacent a region in which the items are dispersed, while the voltage is established, thereby attracting the items to the conducting elements.

Yet another invention is a method of manipulating micron scale microelectronic parts, having a dielectric constant greater than that of an environment in which they are to be manipulated. The method comprises the steps of: providing a microelectronic part on a support within the environment; providing an elongated manipulating electrode that is elongated along a dimension of elongation, terminating in a terminal end, with the terminal end adjacent the supported microelectronic part; and applying a voltage to the electrode, thereby attracting the microelectronic part to the terminal end of the electrode, upon which it becomes retained. If the microelectronic part has a shaped profile, the method further comprises the step of providing the manipulating electrode having a terminal end that is shaped to mate with the shaped profile of the microelectronic part. If the part has a shaped perimeter, the step of providing an elongated manipulating electrode comprises the step of providing a manipulating electrode having a terminal end that is shaped to mate with the shaped perimeter. Even if the electrode is provided with the terminal end misaligned relative to the perimeter of the microelectronic part, the step of applying a voltage to the electrode, will result in attracting the microelectronic part to the terminal end of the electrode, and aligning the perimeter of the microelectronic part with the terminal end of the electrode, upon which it becomes retained.

Finally, an invention is an apparatus for manipulating microelectronic parts having a shaped perimeter and surface contour. The apparatus comprises: a support, for support of the microelectronic part; an elongated manipulating electrode that is elongated along a dimension of elongation, terminating in a terminal end, the terminal end shaped to mate with the surface contour of the microelectronic part; and a couple for coupling the electrode to a voltage supply. The terminal end of the elongated manipulating electrode may further bee shaped to register with the perimeter of the microelectronic part.

This disclosure describes and discloses more than one invention. The inventions are set forth in the claims of this and related documents, not only as filed, but also as developed during prosecution of any patent application based on this disclosure. The inventors intend to claim all of the various inventions to the limits permitted by the prior art, as it is subsequently determined to be. No feature described herein is essential to each invention disclosed herein. Thus, the inventors intend that no features described herein, but not claimed in any particular claim of any patent based on this disclosure, should be incorporated into any such claim.

Some assemblies of hardware, or groups of steps, are referred to herein as an invention. However, this is not an admission that any such assemblies or groups are necessarily patentably distinct inventions, particularly as contemplated by laws and regulations regarding the number of inventions that will be examined in one patent application, or unity of invention. It is intended to be a short way of saying an embodiment of an invention.

An abstract is submitted herewith. It is emphasized that this abstract is being provided to comply with the rule requiring an abstract that will allow examiners and other searchers to quickly ascertain the subject matter of the technical disclosure. It is submitted with the understanding that it will not be used to interpret or limit the scope or meaning of the claims, as promised by the Patent Office's rule.

The foregoing discussion should be understood as illustrative and should not be considered to be limiting in any sense. While the inventions have been particularly shown and described with references to preferred embodiments thereof, it will be understood by those skilled in the art that various changes in form and details may be made therein without departing from the spirit and scope of the inventions as defined by the claims.

The corresponding structures, materials, acts and equivalents of all means or step plus function elements in the claims below are intended to include any structure, material, or acts for performing the functions in combination with other claimed elements as specifically claimed.

Having described the inventions, what is claimed is:

1. An apparatus for manipulating micron scale items having a dielectric constant greater than that of an environment in which they are to be manipulated, said items being provided in a region upon a support, said apparatus comprising:
   a. a manipulating electrode comprising:
      i. a first electrode conducting element comprising an elongated electrode, elongated along a first dimension; and
      ii. spaced from said first electrode conducting element, a second, counter electrode conducting element comprising a plate that is extended in two dimensions that are substantially perpendicular to said first dimension, said first and second conducting elements having surfaces such that any two that face each other, are shaped, sized and spaced such that the spacing between them is large relative to the extent of either facing surface, in any one dimension; and
   b. a means for a coupling a voltage source to said electrode, to establish a voltage between said first and second electrode conducting elements.

2. The apparatus of claim 1, further comprising a stage configured to position said first electrode conducting element and said support such that said first electrode is at a selectable point relative to and adjacent a surface of said region of items.

3. The apparatus of claim 1, further wherein there exists at least one dimension of said first conducting electrode that is small relative to at least one dimension of said second conducting electrode.

4. The apparatus of claim 1, said items being supported by said plate.

5. The apparatus of claim 4, said support and said items being located between said first and second conducting electrodes.

6. The apparatus of claim 1, said plate comprising a recess, said region in which said items reside being said recess.

7. The apparatus of claim 1, said means for coupling a voltage source comprising means for providing a voltage between said plate and said first electrode conducting element.

8. The apparatus of claim 1, further comprising a DC voltage source coupled to said first electrode conducting element.

9. An apparatus for manipulating micron scale items having a dielectric constant greater than that of an environment in which they are to be manipulated, said items being provided in a region upon a support, said apparatus comprising:
 a. a manipulating electrode comprising:
  i. a first electrode conducting element comprising an elongated electrode, elongated along a first dimension; and
  ii. spaced from said first electrode conducting element, a second electrode conducting element comprising an elongated electrode, also elongated along said first dimension, and substantially parallel to said first electrode conducting element said first and second conducting elements having surfaces such that any two that face each other, are shaped, sized and spaced such that the spacing between them is large relative to the extent of either facing surface, in any one dimension; and
 b. a means for a coupling a voltage source to said electrode, to establish a voltage between said first and second electrode conducting elements.

10. The apparatus of claim 9, said first and second electrode conducting elements comprising substantially parallel pins.

11. The apparatus of claim 9, said first and second electrode conducting elements comprising substantially parallel and congruent loops.

12. The apparatus of claim 11, said loops also extending in a second dimension that is substantially perpendicular to said first dimension.

13. The apparatus of claim 9, said first and second conducting elements being substantially parallel, and both having terminal ends, said terminal ends being positioned so that said region in which said items reside is located adjacent said terminal ends.

14. The apparatus of claim 9, said means for coupling a voltage source comprising means for providing a voltage between said first and second electrode conducting elements.

15. The apparatus of claim 14, further comprising an AC voltage source, coupled to said first electrode conducting element.

16. An apparatus for manipulating micron scale items having a dielectric constant greater than that of an environment in which they are to be manipulated, said items being provided in a region upon a support, said apparatus comprising:
 a. a manipulating electrode comprising:
  i. a said first electrode conducting element comprising a disc, having a center and a perimeter; and
  ii. spaced from said first electrode conducting element, a second, counter electrode conducting element comprising a ring that is substantially concentric with and circumscribes said disc, said ring having an inner boundary that is spaced from said perimeter of said disc, said first and second conducting elements having surfaces such that any two that face each other, are shaped, sized and spaced such that the spacing between them is large relative to the extent of either facing surface, in any one dimension; and
 b. a means for a coupling a voltage source to said electrode, to establish a voltage between said first and second electrode conducting elements.

17. An apparatus for manipulating micron scale items having a dielectric constant greater than that of an environment in which they are to be manipulated, said items being provided in a region upon a support, said apparatus comprising:
 a. a manipulating electrode comprising:
  i. a first electrode conducting element comprising an array of elongated manipulating electrodes; and
  ii. spaced from said first electrode conducting element, a second, counter electrode conducting element, said first and second conducting elements having surfaces such that any two that face each other, are shaped, sized and spaced such that the spacing between them is large relative to the extent of either facing surface, in any one dimension; and
 b. a means for a coupling a voltage source to said electrode, to establish a voltage between said first and second electrode conducting elements;
 further comprising a transport device coupled between said array of electrodes with said retained items and a target comprising an array of receptacle target regions, to provide relative motion such that the array of electrodes and said target regions become closer and such that each electrode of said array enters into a respective receptacle of said array of receptacle target regions.

18. The apparatus of claim 17, further comprising a measuring module configured to measure the amount of items released within each of a selected plurality of said receptacles.

19. An apparatus for manipulating micron scale items having a dielectric constant greater than that of an environment in which they are to be manipulated, said items being provided in a region upon a support, said apparatus comprising:
 a. a manipulating electrode comprising:
  i. a first electrode conducting element; and
  ii. spaced from said first electrode conducting element, a second, counter electrode conducting element, said first and second conducting elements having surfaces such that any two that face each other, are shaped, sized and spaced such that the spacing between them is large relative to the extent of either facing surface, in any one dimension; and
 b. a means for a coupling a voltage source to said electrode, to establish a voltage between said first and second electrode conducting elements; and
 a humidity control module configured to maintain an atmosphere of less than approximately 80% relative humidity.

20. An apparatus for manipulating micron scale items having a dielectric constant greater than that of an environment in which they are to be manipulated, said items being provided in a region upon a support, said apparatus comprising:

a. a manipulating electrode comprising:
  i. a first electrode conducting element; and
  ii. spaced from said first electrode conducting element, a second, counter electrode conducting element, said first and second conducting elements having surfaces such that any two that face each other, are shaped, sized and spaced such that the spacing between them is large relative to the extent of either facing surface, in any one dimension; and
b. a means for a coupling a voltage source to said electrode, to establish a voltage between said first and second electrode conducting elements and a transport mechanism coupled to provide relative motion between said manipulating electrode and a target comprising a well of a microtitre tray, such that they become closer.

21. An apparatus for manipulating micron scale items having a dielectric constant greater than that of an environment in which they are to be manipulated, said items being provided in a region upon a support, said apparatus comprising:
a. a manipulating electrode comprising:
  i. a first electrode conducting element; and
  ii. spaced from said first electrode conducting element, a second, counter electrode conducting element, said first and second conducting elements having surfaces such that any two that face each other, are shaped, sized and spaced such that the spacing between them is large relative to the extent of either facing surface, in any one dimension; and
b. a means for a coupling a voltage source to said electrode, to establish a voltage between said first and second electrode conducting elements and a transport mechanism coupled to provide relative motion between said manipulating electrode and a target comprising a recess of a pharmaceutical delivery microchip.

22. An apparatus for manipulating micron scale items having a dielectric constant greater than that of an environment in which they are to be manipulated, said items being provided in a region upon a support, said apparatus comprising:
a. a manipulating electrode comprising:
  i. a first electrode conducting element comprising a conductive membrane of a recess of a pharmaceutical delivery microchip; and
  ii. spaced from said first electrode conducting element, a second, counter electrode conducting element, said first and second conducting elements having surfaces such that any two that face each other, are shaped, sized and spaced such that the spacing between them is large relative to the extent of either facing surface, in any one dimension; and
b. a means for a coupling a voltage source to said electrode, to establish a voltage between said first and second electrode conducting elements.

23. The apparatus of claim 22, said microchip arranged such that to collect items, said conductive membrane, and said recess are located above said support, with said recess having an opening that faces downward.

* * * * *